(12) United States Patent
Kyle et al.

(10) Patent No.: US 11,096,344 B2
(45) Date of Patent: Aug. 24, 2021

(54) GENETIC LOCI ASSOCIATED WITH BROWN STEM ROT RESISTANCE IN SOYBEAN AND METHODS OF USE

(71) Applicant: PIONEER HI-BRED INTERNATIONAL, INC., Johnston, IA (US)

(72) Inventors: Donald Earl Kyle, Princeton, IL (US); Joshua Michael Shendelman, Ankeny, IA (US); John Bryan Woodward, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 0 days.

(21) Appl. No.: 15/777,243

(22) PCT Filed: Jan. 25, 2017

(86) PCT No.: PCT/US2017/014947
§ 371 (c)(1),
(2) Date: May 18, 2018

(87) PCT Pub. No.: WO2017/136204
PCT Pub. Date: Aug. 10, 2017

(65) Prior Publication Data
US 2018/0334728 A1  Nov. 22, 2018

Related U.S. Application Data

(60) Provisional application No. 62/292,001, filed on Feb. 5, 2016.

(51) Int. Cl.
*A01H 1/04* (2006.01)
*C12Q 1/6895* (2018.01)
*A01H 6/54* (2018.01)
*A01H 5/10* (2018.01)

(52) U.S. Cl.
CPC ............. *A01H 1/045* (2021.01); *A01H 5/10* (2013.01); *A01H 6/542* (2018.05); *C12Q 1/6895* (2013.01); *C12Q 2600/156* (2013.01); *C12Q 2600/172* (2013.01)

(58) Field of Classification Search
None
See application file for complete search history.

(56) References Cited

FOREIGN PATENT DOCUMENTS

WO        2014/150226 A1    9/2014
WO    WO 2014/150226    *    9/2014

OTHER PUBLICATIONS

Joshi et al, 2013, BMC Genomics 14 (Suppl 1):55.*
Song et al (2010, Crop Sci. 1950-1960, plus relevant section of BARCSOYSSR_1.0 markers available in SoyBase the USDA-ARS Soybean Genome Database, http://soybase.org).*
Lee et al 2015, Plant J. 81:625-636, published online Dec. 30, 2014).*
Lewers, K.S., et al.: "Detection of linked QTL for soybean brown stem rot resistance in 'BSR 101' as expressed in a growth chamber environment", Molecular Breeding, Jan. 1, 1999 (Jan. 1, 1999), pp. 33-42.
International Search Report and Written Opinion, International Application No. PCT/US2017/014947 dated Apr. 7, 2017.
Hughes et. al. "Influence of Soybean Monoculture on *Phialophora gregata* f. sp. sojae IGS-Genotype B Isolate Aggressiveness" Plant Disease 94(1): 69-74 (2010).
Perez et al. "Genetic Analysis of New Sources of Soybean Resistance to Brown Stem Rot" Crop Science 50: 2431-2439 (2010).

* cited by examiner

*Primary Examiner* — Anne Kubelik

(57) ABSTRACT

Various methods and compositions are provided for identifying and/or selecting a soybean plant or soybean germplasm with improved resistance to Brown Stem Rot infection. In certain embodiments, the method comprises detecting at least one allele of one or more marker locus within or linked to a QTL associated with Brown Stem Rot resistance. In further embodiments, the method comprises crossing a selected soybean plant with a recurrent soybean parent plant. Further provided herein are marker loci, marker alleles, primers, probes, and kits suitable for identifying and/or selecting soybean plants or soybean germplasms with improved resistance to Brown Stem Rot infection.

22 Claims, 4 Drawing Sheets
Specification includes a Sequence Listing.

| Marker Locus Name | Marker Type | Chromosome (Linkage Group) | Map Position (cM) |
|---|---|---|---|
| BARC-023719-03461 | SNP | 16 (J) | 50.469 |
| BARC-048421-10588 | SNP | 16 (J) | 51.413 |
| BARC-029037-06053 | SNP | 16 (J) | 51.571 |
| BARC-047927-10430 | SNP | 16 (J) | 53.417 |
| BARC-038949-07404 | SNP | 16 (J) | 57.697 |
| Sat_366 | SSR | 16 (J) | 57.951 |
| BARC-059837-16121 | SNP | 16 (J) | 58.386 |
| BARC-018761-03242 | SNP | 16 (J) | 58.474 |
| Bng063_1 | RFLP | 16 (J) | 59.825 |
| B122_1 | RFLP | 16 (J) | 59.921 |
| RGA_3 | RFLP | 16 (J) | 60.554 |
| Sat_350 | SSR | 16 (J) | 60.717 |
| BARC-031917-07226 | SNP | 16 (J) | 60.927 |
| BARC-042193-08207 | SNP | 16 (J) | 62.957 |
| bac27T | RFLP | 16 (J) | 63.057 |
| BARC-012111-00333 | SNP | 16 (J) | 64.9 |
| BARC-032663-09006 | SNP | 16 (J) | 65.777 |
| BARC-043081-08519 | SNP | 16 (J) | 66.003 |
| BARC-022321-04314 | SNP | 16 (J) | 66.431 |
| BARC-017697-03107 | SNP | 16 (J) | 66.445 |
| BARC-024047-04716 | SNP | 16 (J) | 66.474 |
| BARC-059845-16134 | SNP | 16 (J) | 66.489 |
| BARC-022077-04282 | SNP | 16 (J) | 66.556 |
| BARC-014795-01662 | SNP | 16 (J) | 66.56 |
| BARC-059943-16234 | SNP | 16 (J) | 66.848 |
| BARC-042895-08450 | SNP | 16 (J) | 67.053 |
| BARC-041267-07957 | SNP | 16 (J) | 67.229 |
| RGA_2a | RFLP | 16 (J) | 67.465 |
| BARC-043111-08534 | SNP | 16 (J) | 67.482 |
| BARC-060179-16450 | SNP | 16 (J) | 67.74 |
| BARC-012111-00338 | SNP | 16 (J) | 67.757 |
| BARC-030499-06883 | SNP | 16 (J) | 67.758 |
| BARC-011645-00322 | SNP | 16 (J) | 67.895 |
| BARC-028339-05837 | SNP | 16 (J) | 67.97 |

Figure 1A

| | | | |
|---|---|---|---|
| BARC-011637-00315 | SNP | 16 (J) | 68.714 |
| Sctt011 | SSR | 16 (J) | 68.809 |
| pcr2_135 | other | 16 (J) | 68.948 |
| BARC-057313-14690 | SNP | 16 (J) | 69.326 |
| BARC-010297-00580 | SNP | 16 (J) | 69.895 |
| BARC-028369-05854 | SNP | 16 (J) | 69.97 |
| BARC-023637-03433 | SNP | 16 (J) | 70.404 |
| Satt244 | SSR | 16 (J) | 70.696 |
| BARC-049039-10794 | SNP | 16 (J) | 70.988 |
| BARC-039399-07318 | SNP | 16 (J) | 71.191 |
| BARC-017835-02393 | SNP | 16 (J) | 71.322 |
| BARC-010095-00512 | SNP | 16 (J) | 71.418 |
| BARC-012971-00414 | SNP | 16 (J) | 71.559 |
| BARC-064455-18689 | SNP | 16 (J) | 71.559 |
| BARC-024115-04764 | SNP | 16 (J) | 71.919 |
| BARC-046044-10204 | SNP | 16 (J) | 72.138 |
| K375_1 | RFLP | 16 (J) | 72.465 |
| BARC-042697-08373 | SNP | 16 (J) | 72.476 |
| BARC-039625-07523 | SNP | 16 (J) | 73.211 |
| BARC-040393-07727 | SNP | 16 (J) | 73.255 |
| BARC-027836-06689 | SNP | 16 (J) | 73.538 |
| R189_1 | RFLP | 16 (J) | 73.807 |
| BARC-025217-06463 | SNP | 16 (J) | 73.898 |
| BARC-042131-08181 | SNP | 16 (J) | 73.898 |
| BARC-012505-00912 | SNP | 16 (J) | 73.924 |
| BARC-042131-08182 | SNP | 16 (J) | 74.742 |
| Satt547 | SSR | 16 (J) | 74.895 |
| Sat_396 | SSR | 16 (J) | 75.804 |
| BARC-028589-05965 | SNP | 16 (J) | 76.141 |
| BARC-051887-11292 | SNP | 16 (J) | 76.212 |
| BARC-042413-08254 | SNP | 16 (J) | 76.216 |
| BARC-030433-06867 | SNP | 16 (J) | 76.614 |
| BARC-053847-12078 | SNP | 16 (J) | 77.269 |
| BARC-051715-11216 | SNP | 16 (J) | 77.398 |
| B032_1 | RFLP | 16 (J) | 77.598 |
| G815_1 | RFLP | 16 (J) | 77.992 |
| Sat_224 | SSR | 16 (J) | 78.828 |
| BARC-045099-08885 | SNP | 16 (J) | 78.968 |

Figure 1B

| | | | |
|---|---|---|---|
| BARC-025851-05117 | SNP | 16 (J) | 80.794 |
| BARC-021875-04228 | SNP | 16 (J) | 81.139 |
| L050_10 | RFLP | 16 (J) | 81.262 |
| BARC-044031-08587 | SNP | 16 (J) | 81.413 |
| Satt431 | SSR | 16 (J) | 82.025 |
| BARC-045133-08889 | SNP | 16 (J) | 84.071 |
| BARC-041173-07927 | SNP | 16 (J) | 84.469 |
| RGA_1a | RFLP | 16 (J) | 84.573 |
| BARC-015307-02272 | SNP | 16 (J) | 84.762 |
| BARC-011625-00310 | SNP | 16 (J) | 85.577 |
| BARC-019229-03401 | SNP | 16 (J) | 85.841 |
| BARC-060143-16410 | SNP | 16 (J) | 85.841 |
| BARC-048169-10506 | SNP | 16 (J) | 86.004 |
| BARC-024229-04809 | SNP | 16 (J) | 86.169 |
| A724_1 | RFLP | 16 (J) | 86.37 |
| A233_1 | RFLP | 16 (J) | 86.742 |
| BARC-019215-03395 | SNP | 16 (J) | 86.807 |
| BARC-048491-10612 | SNP | 16 (J) | 86.807 |
| BARC-048135-10500 | SNP | 16 (J) | 86.821 |
| Sat_144 | SSR | 16 (J) | 87.059 |
| BARC-019219-03397 | SNP | 16 (J) | 87.383 |
| BARC-030203-06832 | SNP | 16 (J) | 87.575 |
| BARC-031515-07105 | SNP | 16 (J) | 88.501 |
| BARC-029163-06102 | SNP | 16 (J) | 88.51 |
| BARC-030817-06946 | SNP | 16 (J) | 88.929 |
| BARC-028761-06008 | SNP | 16 (J) | 89.36 |
| Satt712 | SSR | 16 (J) | 89.908 |
| Sat_394 | SSR | 16 (J) | 89.913 |
| Sat_395 | SSR | 16 (J) | 89.926 |
| A199_2 | RFLP | 16 (J) | 90.101 |
| Sat_393 | SSR | 16 (J) | 90.458 |
| pcr2_176 | other | 16 (J) | 90.65 |
| RGA_1c | RFLP | 16 (J) | 90.825 |
| bac91f11U1 | RFLP | 16 (J) | 90.856 |
| bac91f11U2 | RFLP | 16 (J) | 91.956 |
| RGA_1b | RFLP | 16 (J) | 92.24 |
| A132_3 | RFLP | 16 (J) | 92.266 |

Figure 1C

GENETIC LOCI ASSOCIATED WITH BROWN STEM ROT RESISTANCE IN SOYBEAN AND METHODS OF USE

FIELD

This disclosure relates to methods of identifying and/or selecting soybean plants or soybean germplasm that display improved resistance to Brown Stem Rot infection.

BACKGROUND

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications.

Brown stem rot (BSR) is a disease in soybeans caused by the fungus *Phialophora gregata* and is widely established throughout the north-central U.S., where soybeans are its only host. BSR infection causes vascular and pith tissues to turn brown to reddish brown. It is observable by splitting stems longitudinally at and between nodes near the soil line to inspect for the characteristic brown growth. BSR severity can be measured by the height of the internal stem discoloration, with more severe infections continuous throughout the stems rather than only at the nodes. The fungus tends to infect roots early in the season, with the infection progressing from the roots to the vascular system, which is the water and food-conduction portion of plants.

As such, vascular system damage usually appears in midsummer during reproductive development. In addition, plants with severe infections can exhibit leaf necrosis and chlorosis. These foliar symptoms appear around reproductive growth stage R3-R4 as pods start to fill and may ultimately result in leaf death.

There are two known strains—strain A is highly aggressive and causes both stem and leaf symptoms, whereas strain B causes more mild symptoms usually occurring only in the stem. Plant damage is thought to occur due to the toxins produced by this fungus, which ultimately causes a disruption of the vascular system and may result in premature death of the entire plant (see Westphal et al., "Diseases of Soybean: Brown Stem Rot" *Purdue Extension* BP-41-W available from the Purdue University website (www.extension.dot.purdue.edu)). Plant death is of particular concern where heat and/or drought stress impact diseased plants. When severe, BSR strain A can reduce soy yields up to 40%. Thus, selection of plants with resistance or improved resistance to BSR infection and/or the production of soybean varieties with improved resistance to BSR infection may increase soybean yields in regions where BSR infection is widespread.

Through selective breeding for BSR resistance, soybean varieties are being developed that display resistance or improved resistance to BSR infection. Unfortunately, field testing for BSR resistance is laborious and challenging. However, the use of genetic markers associated with BSR resistant allows for the selection of BSR resistance traits without having to conduct field testing and expedite the introgression of these desired traits into elite cultivars.

Genetic markers have been used to selectively improve soybean crops through the use of marker assisted selection. Any detectible polymorphic trait can be used as a marker so long as it is inherited differentially and exhibits linkage disequilibrium with a phenotypic trait of interest. A number of soybean markers have been mapped and linkage groups created, as described in Cregan, P. B., et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96, and Hyten et al., "A High Density Integrated Linkage Map of Soybean and the Development of a 1536 Universal Soy Linkage Panel for Quantitative Trait Locus Mapping" (2010) Crop Sci. 50:960-968. Many soybean markers are publicly available at the USDA affiliated soybase website (http://www.soybase.org/).

Most plant traits of agronomic importance are polygenic, otherwise known as quantitative, traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicate greater linkage between the QTL and the molecular marker. The extent to which two features are linked is often referred to as the genetic distance. The genetic distance is also typically related to the physical distance between the marker and the QTL; however, certain biological phenomenon (including recombinational "hot spots") can affect the relationship between physical distance and genetic distance. Generally, the usefulness of a molecular marker is determined by the genetic and physical distance between the marker and the selectable trait of interest.

In some cases, multiple closely linked markers, such as Single Nucleotide Polymorphism (SNP) markers, can be found to exist in a certain region of a plant genome encompassing one or more QTL. In such cases, by determining the allele present at each of those marker loci, a haplotype for that region of the plant genome can be determined. Further, by determining alleles or haplotypes present at multiple regions of the plant genome related to the same phenotypic trait, a marker profile for that trait can be determined. Such haplotype and marker profile information can be useful in identifying and selecting plants with certain desired traits.

Multiple closely linked markers, such as SNPs, have been found in certain regions of the soybean plant genome encompassing one or more QTLs associated with resistance to BSR infection. BSR resistant traits are known to arise from different sources of soybean germplasm that are identifiable by detecting particular combinations of marker alleles referred to as haplotypes. The haplotypes can be used to track and/or detect various sources of BSR resistance and can be used to predict a particular type of BSR resistance trait that will be displayed by the soybean plant. For example, rbs3a haplotypes, including the rbs3a hidden haplotype, are associated with a BSR resistance trait that confers very high resistance to BSR infection, whereas the genetic haplotypes rbs3b and rbs3b hidden are associated with a more moderate or incomplete resistance to BSR infection. While marker loci have been found to be highly associated with one or more particular sources of BSR resistance, marker loci associated with all BSR resistance haplotypes and capable of distinguishing BSR-susceptible soybean plants from soybean plants displaying BSR resistance derived from any source have yet to be discovered.

Thus, there remains a need to identify genetic markers useful for the detection of BSR resistance in soybean plants to enable the selection of soybean plants displaying resistance to BSR infection. The molecular markers and methods provided herein provide important tools for use in plant breeding programs to identify BSR resistant plants and/or to develop soybean varieties with improved resistance to BSR infection.

SUMMARY

Various methods and compositions are provided for identifying and/or selecting a soybean plant or soybean germplasm with improved resistance to BSR infection. For example, a method of selecting a soybean plant or soybean germplasm having improved resistance to brown stem rot infection is provided that includes (a) detecting in a soybean plant or soybean germplasm at least one allele of one or more marker locus within or linked to a quantitative trait locus (QTL) associated with resistance to brown stem rot infection, wherein the allele positively correlates with resistance to brown stem rot infection, and wherein the one or more marker locus is selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof; and (b) selecting the soybean plant or soybean germplasm comprising the at least one allele from step (a), thereby selecting a soybean plant with improved resistance to brown stem rot infection.

Some methods further comprise detecting in the soybean plant or soybean germplasm at least one allele of one or more marker locus associated with an rbs3a haplotype, wherein the allele positively correlates with rbs3a-type resistance to brown stem rot infection, and wherein the one or more marker locus is selected from the group consisting of Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 and a combination thereof; and selecting the soybean plant or soybean germplasm comprising the allele of one or more marker locus associated with an rbs3a haplotype, thereby selecting a soybean plant with improved rbs3a-type resistance to brown stem rot infection.

In yet other embodiments, the method further comprises detecting in the soybean plant or soybean germplasm at least one allele of one or more marker locus associated with an rbs3b haplotype, wherein the allele positively correlates with rbs3b-type resistance to brown stem rot infection, and wherein the one or more marker locus is selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof; and selecting the soybean plant or soybean germplasm comprising the allele of one or more marker locus associated with an rbs3b haplotype, thereby selecting a soybean plant with improved rbs3b-type resistance to brown stem rot infection.

Some methods further include detecting in the soybean plant or soybean germplasm at least one allele of one or more marker locus associated with an rbs3b hidden haplotype, wherein the allele positively correlates with rbs3b-type resistance to brown stem rot infection, and wherein the one or more marker locus is selected from the group consisting of Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof, and selecting the soybean plant or soybean germplasm comprising the allele of one or more marker locus associated with an rbs3b hidden haplotype, thereby selecting a soybean plant with improved rbs3b-type resistance to brown stem rot infection.

In another aspect, a method of selecting soybean plants for improved resistance to brown stem rot infection is provided that includes providing a population of genetically diverse soybean plants; extracting genomic DNA samples from each of the soybean plants in the population; admixing a first isolated polynucleotide with each of the genomic DNA samples, wherein the first polynucleotide is capable of hybridizing with a favorable allele of a marker locus selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof; detecting the presence of a hybridized first polynucleotide in one or more of the genomic DNA samples, wherein the presence of the hybridized first polynucleotide indicates a soybean plant with improved resistance to brown stem rot infection; and selecting at least one soybean plant with improved resistance to brown stem rot infection. In other aspects, the method further comprises crossing a selected soybean plant to a recurrent parent soybean plant to produce a population of progeny soybean germplasm.

A kit for selecting at least one soybean plant or soybean germplasm by marker assisted selection of a QTL associated with resistance to brown stem rot infection is also provided that includes: (a) primers or probes for detecting polymorphism on chromosome 16 in the soybean genome, wherein the physical location of the polymorphism is selected from the group consisting of 32543279 bp, 32544128 bp, 32544169 bp, 32545642 bp, 32544181 bp, 32545680 bp, 32291307 bp, 32543387 bp, 32284137 bp, 32544094 bp, 32543360 bp, 32546349 bp, 32324276 bp, 32544455 bp, 32346680 bp, 32543724 bp, 32546343 bp, 32543241 bp, 32542545 bp, 32286588 bp, 32546309 bp, 32282532 bp, 32540234 bp, 32346259 bp, 32546697 bp, 32286461 bp, 32542834 bp, 32346754 bp, 32286518 bp, 32542809 bp, 32545807 bp, 32239934 bp, 32544481 bp, 32346987 bp, 32347808 bp, 32540201 bp, 32546282 bp, 32286403 bp, 32545360 bp, 32285402 bp, 32544988 bp, 32286428 bp, 32283215 bp, 32454541 bp and a combination thereof; and (b) instructions for using the primers or probes to detect the polymorphism and correlate the polymorphism with improved resistance to brown stem rot infection.

BRIEF DESCRIPTION OF THE DRAWINGS

FIG. 1A illustrates a genetic map comprising a portion of chromosome 16 of soybean and provides a list of marker loci in linkage group J between genetic map positions 50.469 and 67.97. Map positions are provided in centiMorgans (cM) using a genetic map based upon Hyten et al., "A High Density Integrated Linkage Map of Soybean and the Development of a 1536 Universal Soy Linkage Panel for Quantitative Trait Locus Mapping" (2010) Crop Sci. 50:960-968, and is also available at the USDA affiliated soybase website (http://www.soybase.org/).

FIG. 1B is a continuation of FIG. 1A and illustrates a genetic map comprising a portion of chromosome 16 of soybean and provides a list of marker loci in linkage group J between genetic map positions 68.714 cM and 78.968 cM.

FIG. 1C is a continuation of FIG. 1B and illustrates a genetic map comprising a portion of chromosome 16 of soybean and provides a list of marker loci in linkage group J between genetic map positions 80.794 cM and 92.266 cM.

SUMMARY OF BIOLOGICAL SEQUENCES

Figure 2:
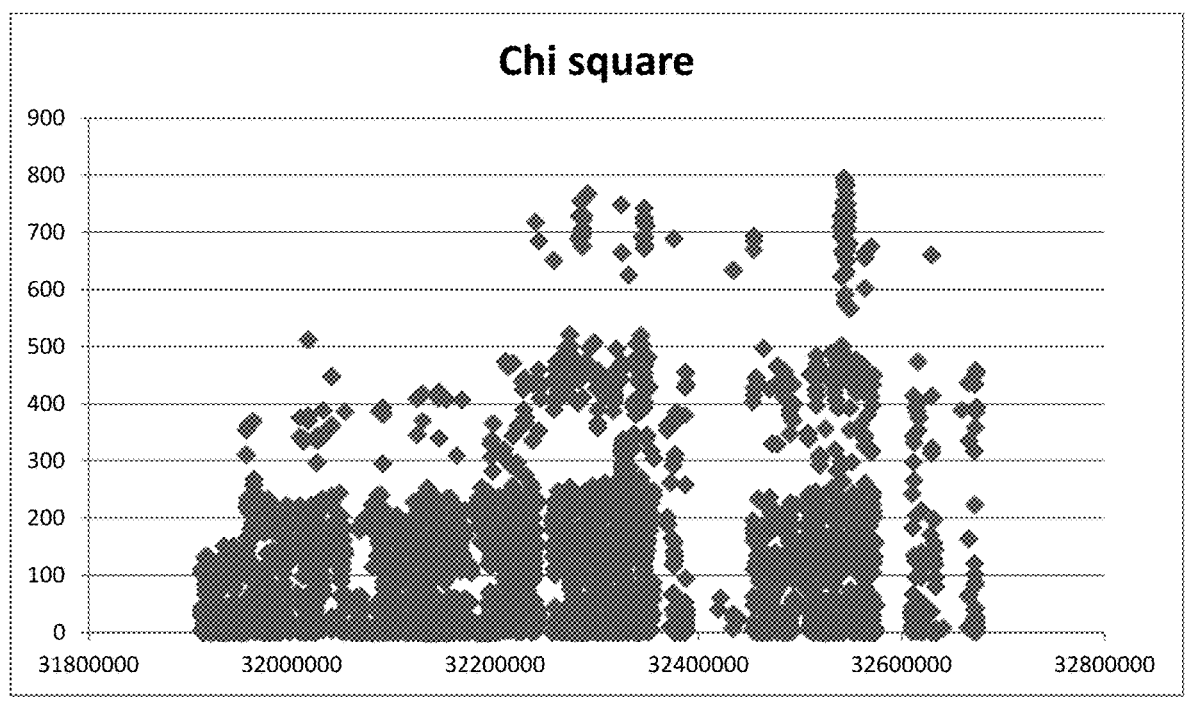
FIG. 2 is a graph revealing a locus conditioning BSR resistance between 32,239,934 bp and 32,546,697 bp on chromosome 16 of soybean. The y-axis depicts chi square values plotted against the physical position of the SNPs on chromosome 16 (x-axis). The physical position within the soybean genome provided is based on the *Glycine max* Williams 82 v1.1 genome sequence described in Schmutz et al. (2010) Nature 463:178-183, available from the Phytozome website (http://phytozome.jgi.doe.gov/pz/portal.html) or from the GenBank website (http://www.ncbi.nlm.nih.gov/).

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with the World Intellectual Property Organization (WIPO) Standard ST.25 (1998) and the sequence listing requirements of the European Patent Convention (EPC) and the Patent Cooperation Treaty (PCT) Rules 5.2 and 49.5 (a-bis), and Section 208 and Annex C of the Administrative Instructions. The symbols and format used for nucleotide and amino acid sequence data comply with the rules set forth in 37 C.F.R. § 1.822.

SEQ ID NOs: 1-44 are genomic DNA regions encompassing the marker loci described on Table 1.

SEQ ID NOs: 45-66 are genomic DNA regions encompassing the marker loci described on Table 2.

SEQ ID NOs: 67-110 are genomic DNA regions encompassing the marker loci described on Table 3.

SEQ ID NOs: 111-155 are genomic DNA regions encompassing the marker loci described on Table 4.

SEQ ID NOs: 156-159 comprise nucleotide sequences of regions of the soybean genome, each capable of being used as a probe or primer, either alone or in combination, for the detection of a marker locus Gm16:32544169 on chromosome 16 (LG-J). In certain methods, SEQ ID NOs: 156 and 157 are used as primers and SEQ ID NOs: 158 and 159 are used as allele specific probes.

SEQ ID NOs: 160-163 comprise nucleotide sequences of regions of the soybean genome, each capable of being used as a probe or primer, either alone or in combination, for the detection of a marker locus Gm16:32234335 on chromosome 16 (LG-J). In certain methods, SEQ ID NOs: 160 and 161 are used as primers and SEQ ID NOs: 162 and 163 are used as allele specific probes.

SEQ ID NOs: 164-167 comprise nucleotide sequences of regions of the soybean genome, each capable of being used as a probe or primer, either alone or in combination, for the detection of a marker locus Gm16:32296634 on chromosome 16 (LG-J). In certain methods, SEQ ID NOs: 164 and 165 are used as primers and SEQ ID NOs: 166 and 167 are used as allele specific probes.

SEQ ID NOs: 168-171 comprise nucleotide sequences of regions of the soybean genome, each capable of being used as a probe or primer, either alone or in combination, for the detection of a marker locus Gm16:32271574 on chromosome 16 (LG-J). In certain methods, SEQ ID NOs: 168 and 169 are used as primers and SEQ ID NOs: 170 and 171 are used as allele specific probes.

SEQ ID NO: 172 is the amplicon produced by amplifying genomic DNA using SEQ ID NO: 156 as a forward or reverse primer in conjunction with SEQ ID NO: 157 as the other primer in the pair. This amplicon encompasses marker locus Gm16:32544169 on chromosome 16 (LG-J).

SEQ ID NO: 173 is the amplicon produced by amplifying genomic DNA using SEQ ID NO: 160 as a forward or reverse primer in conjunction with SEQ ID NO: 161 as the other primer in the pair. This amplicon encompasses marker locus Gm16:32234335 on chromosome 16 (LG-J).

SEQ ID NO: 174 is the amplicon produced by amplifying genomic DNA using SEQ ID NO: 164 as a forward or reverse primer in conjunction with SEQ ID NO: 165 as the other primer in the pair. This amplicon encompasses marker locus Gm16:32296634 on chromosome 16 (LG-J).

SEQ ID NO: 175 is the amplicon produced by amplifying genomic DNA using SEQ ID NO: 168 as a forward or reverse primer in conjunction with SEQ ID NO: 169 as the other primer in the pair. This amplicon encompasses marker locus Gm16:32271574 on chromosome 16 (LG-J).

DETAILED DESCRIPTION

Provided herein are genetic marker loci associated with resistance to brown stem rot (BSR) infection in soybean. In particular, provided herein are genetic markers loci within or linked to a QTL associated with resistance to BSR infection and are capable of distinguishing a soybean plant or soybean germplasm with a BSR resistance trait from soybean plants or germplasms displaying susceptibility to BSR infection. Thus, in certain aspects of this disclosure, marker loci and marker alleles within or linked to a QTL associated with BSR resistance and methods of their use are provided. Also provided are genetic marker loci associated with a particular source of BSR resistance. In particular, these genetic marker loci are associated with an rbs3a haplotype, rbs3b haplotype, or rbs3b hidden haplotype and are useful for identifying and/or selecting a soybean plant or soybean germplasm displaying a particular type of BSR resistance, such as rbs3a-type or rbs3b-type. The marker loci provided herein and methods of using these marker loci alleviate the need to screen multiple alleles and haplotypes to identify BSR resistance across heterogeneous populations of soybean and thus represent an improvement in simplicity and efficiency over known methods.

It is to be understood that this disclosure is not limited to particular embodiments, which can, of course, vary. It is also to be understood that the terminology used herein is for the purpose of describing particular embodiments only, and is not intended to be limiting.

In this disclosure, a number of terms and abbreviations are used. Certain definitions used in this disclosure and claims are provided below. In order to provide a clear and consistent understanding of the disclosure and claims, including the scope to be given such terms, the following definitions apply unless specifically stated otherwise.

In addition, the disclosure of each reference set forth herein is hereby incorporated by reference in its entirety.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include embodiments encompassed by the terms "consisting essentially of" and "consisting of." Similarly, the term "consisting essentially of" is intended to include embodiments encompassed by the term "consisting of."

"Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant. An allele is "favorable" for a certain phenotypic trait if that allele positively correlates with that phenotypic trait. An allele is "unfavorable" for a certain phenotypic trait if that allele negatively correlates with that phenotypic trait.

The term "amplifying" in the context of nucleic acid amplification is any process whereby an additional copy or copies of a selected nucleic acid (or a transcribed form thereof) are produced. An "amplicon" is an amplified nucleic acid, e.g., a nucleic acid that is produced by amplifying a template nucleic acid by any available amplification.

The term "associated" or "association" when used in reference to a marker, marker allele, and/or polymorphism and a phenotypic trait and/or haplotype refers to any statistically significant correlation between the presence of a given allele of a marker locus and the phenotypic trait and/or haplotype, which may be qualitative or quantitative.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "recurrent" plant or "recurrent parent" plant refers to a plant typically having a genetic background with favorable agronomic traits that is crossed with a soybean plant comprising a desired trait or allele, which is sometimes referred to as a "donor" plant or "donor parent" plant. Backcrossing then enables the breeder to transfer the desired trait or allele from the donor plant into the favored genetic background of the recurrent plant.

A "genetic map" is a description of genetic association or linkage relationships among loci on one or more chromosomes (or linkage groups) within a given species, generally depicted in a diagrammatic or tabular form.

"Genotype" is a description of the allelic state at one or more loci.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, haplotype, marker profile, marker locus, marker allele, trait, or trait locus from the genome of one plant into the genome of another plant.

The terms "label" or "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seeds sharing a common genotype at the specified locus (or loci) are bulked providing a subline that is genetically homogenous at identified loci important for a trait of interest (e.g., yield, BSR resistance, etc.).

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a genetic map distance of 1.0 centiMorgan (1.0 cM).

The genetic elements or genes located on a single chromosome segment are physically linked. In some embodiments, the two loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosomal segment are also "genetically linked", typically within a genetic recombination distance of less than or equal to 50 cM, e.g., about 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.75, 0.5, 0.25 cM or less. That is, two genetic elements within a single chromosomal segment undergo recombination during meiosis with each other at a frequency of less than or equal to about 50%, e.g., about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 166%, 15%, 14%, 13%, 12%, 11%, 10%, 9%, 8%, 7%, 6%, 5%, 4%, 3%, 2%, 1%, 0.75%, 0.5%, 0.25% or less. "Closely linked" markers display a cross over frequency with a given marker of about 10% or less, e.g., 9%, 8%, 7%, 6%, 5%, 4%, 3%, 2%, 1%, 0.75%, 0.5%, 0.25% or less (the given marker locus is within about 10 cM of a closely linked marker locus, e.g., 9, 8, 7, 6, 5, 4, 3, 2, 1, 0.75, 0.5, 0.25 cM or less of a closely linked marker locus). Put another way, closely linked marker loci co-segregate at least about 90% the time, e.g., 91%, 92%, 93%, 94%, 95%, 96%, 97%, 98%, 99%, 99.5%, 99.75%, or more of the time.

When referring to the relationship between two genetic elements, such as a genetic element contributing to BSR resistance and a proximal marker, "coupling" phase linkage indicates the state where the favorable allele at the BSR resistance is physically associated on the same chromosome strand as the favorable allele of the respective lined marker locus. In the coupling phase, both favorable alleles are inherited together by progeny that inherit the chromosome strand. In "repulsion" phase linkage, the favorable allele at the locus of interest (e.g., a QTL or haplotype associated with resistance to BSR infection) is physically linked with an unfavorable allele at the proximal marker locus, and the two favorable alleles are not inherited together (i.e., the two loci are "out of phase" with each other).

"Linkage disequilibrium" is a non-random association of alleles at two or more loci wherein the two or more alleles occur together at a greater frequency than expected from their individual frequencies. "Linkage disequilibrium" can also occur between unlinked markers. It is based on allele frequencies within a population and is influenced by but not dependent on linkage.

"Linkage group" (LG) refers to traits or markers that generally co-segregate. A linkage group generally corresponds to a chromosomal region containing genetic material that encodes the traits or markers.

"Locus" is a defined segment of DNA.

A "map location" or "map position" is an assigned location on a genetic map relative to linked genetic markers where a specified marker can be found within a given species. Map positions are generally provided in centimorgans (cM), unless otherwise indicated, genetic positions provided are based on the *Glycine max* consensus map v 4.0 as provided by Hyten et al. (2010) Crop Sci 50:960-968, and is also available at the USDA affiliated soybase website (http://www.soybase.org/). A "physical position" or "physical location" or "physical map location" is the position, typically in nucleotides bases, of a particular nucleotide, such as a SNP nucleotide, on a chromosome. Unless otherwise indicated, the physical position within the soybean genome provided is based on the *Glycine max* Williams 82 v1.1 genome sequence described in Schmutz et al. (2010) Nature 463:178-183, available from the Phytozome website (http://phytozome.jgi.doe.gov/pz/portal.html) or from the GenBank website (http://www.ncbi.nlm.nih.gov/). With regard to physical position on a chromosome, closely linked markers can be separated, e.g., by about 1 megabase (MB; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

"Mapping" is the process of defining the association and relationships of loci through the use of genetic markers, populations segregating for the markers, and/or standard genetic principles of recombination frequency.

"Marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest.

"Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

A "mixed defined plant population" refers to a plant population containing many different families and lines of plants. Typically, the defined plant population exhibits a quantitative variability for a phenotype that is of interest. "Multiple plant families" refers to different families of related plants within a population.

"Haplotype" refers to a combination of particular alleles present within a particular plant's genome at two or more linked marker loci, for instance at two or more loci on a particular linkage group. For instance, in one embodiment, two specific marker loci on chromosome 16 (LG-J) are used to define a haplotype for a particular plant. In still further embodiments, 3, 4, 5, 6, 7, 8, 9, 10, 11, 12, 13, 14, 15, 16, 17, 18, 19, 20, or more linked marker loci are used to define a haplotype for a particular plant.

An "rbs3a haplotype" or an "rbs3a hidden haplotype", collectively referred to herein as "rbs3a haplotypes" or an "rbs3a haplotype", refer to a combination of particular alleles that identifies a particular source of resistance to BSR infection. An "rbs3a haplotype" tracks a BSR resistance trait that is characterized as a high level of resistance, which is referred to herein as "rbs3a-type resistance".

An "rbs3b haplotype" refers to a combination of particular alleles that identifies a particular source of resistance to BSR infection, which is characterized as a moderate or incomplete resistance to BSR infection referred to herein as "rbs3b-type resistance". In some soybean plants and germplasms, an rbs3b haplotype is associated with or genetically linked to a frogeye leaf spot resistance trait.

An "rbs3b hidden haplotype" refers to a combination of particular alleles that identifies a particular source of resistance to BSR infection, which is characterized as a moderate or incomplete resistance to BSR infection referred to herein as "rbs3b-type resistance".

The term "rbs3 haplotype" is used herein to refer to any "rbs3a haplotype", "rbs3b haplotype", or "rbs3b hidden haplotype."

The term "rbs3 source" is used herein to refer to any source of BSR resistance that is associated with an rbs3 haplotype.

When describing an association or relationship between a marker loci or an allele thereof and a particular haplotype, the term "offtype" is used herein to refer to any other haplotype, group of haplotypes, and/or phenotypic trait included in the analysis. For example, in a case control study to determine the level of association between a marker locus and an rbs3a haplotype compared to susceptibility, rbs3b haplotypes, and rbs3b hidden haplotypes, the "offtype" group may include susceptibility, rbs3b haplotypes, and rbs3b hidden haplotypes. On the other hand, in a case control study to determine the level of association between a marker locus and an rbs3b haplotype compared to susceptibility, rbs3a haplotypes, and rbs3b hidden haplotypes, the "offtype" group may include susceptibility, rbs3a haplotypes, and rbs3b hidden haplotypes.

As used herein, a "marker profile" means a combination of particular alleles present within a particular plant's genome at two or more marker loci which are not linked, for instance two or more loci on two or more different linkage groups or two or more chromosomes. For instance, in one embodiment, a particular combination of marker loci or a particular combination of haplotypes define the marker profile of a particular plant. For instance, in one embodiment, one marker locus on chromosome 16 (LG-J) and a marker locus on another linkage group are used to define a marker profile for a particular plant. In certain other embodiments, a plant's marker profile comprises one or more haplotypes. In some embodiments, the marker profile encompasses two or more loci for the same trait, such as improved resistance or improved tolerance to BSR infection. In other embodiments, the marker profile encompasses two or more loci associated with two or more traits of interest, such as BSR resistance and a second trait of interest.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid," "nucleic acid molecule," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Resistance" and "improved resistance" are used interchangeably herein and refer to any type of increase in resistance or resistance to, or any type of decrease in susceptibility. A "resistant plant" or "resistant plant variety" need not possess absolute or complete resistance. Instead, a "resistant plant," "resistant plant variety," or a plant or plant variety with "improved resistance" will have a level of resistance or tolerance which is higher than that of a comparable susceptible plant or variety.

"Tolerance" and "improved tolerance" are used interchangeably herein and refer to any type of tolerance to, or any type of decrease in susceptibility. A "Tolerant plant" or "tolerant plant variety" need not possess absolute or complete tolerance. Instead, a "tolerant plant," "tolerant plant variety," or a plant or plant variety with "improved tolerance" will have a level of tolerance which is higher than that of a comparable susceptible plant or variety.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media or other chemical components. Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Genetic Loci Associated with BSR Resistance

Methods are provided for identifying and/or selecting a soybean plant or soybean germplasm having improved resistance to BSR infection. In particular, marker loci have been identified within or linked to a QTL associated with resistance to BSR infection and are capable of detecting BSR resistant traits derived from any rbs3 source of BSR resistance. In other words, in a heterogeneous population, these marker loci are highly associated with all sources of BSR resistance tracked by the rbs3a haplotype, rbs3b haplotype, or the rbs3b hidden haplotype. Previously in the art, multiple marker loci had to be used to accomplish this task. The advantage of using these marker loci for the identification and/or selection of a soybean plant or soybean germplasm displaying resistance or improved resistance to BSR infection is that a single marker can be used to distinguish most, or even all. BSR resistant plants in a heterogeneous population from susceptible material, thus enabling the breeder to eliminate BSR-susceptible soybean plants and soybean germplasms from the breeding program.

It may also be desirable to identify a particular source of BSR resistance in a BSR-resistant soybean plant or germplasm. The BSR resistance phenotype can be classified into two main categories, rbs3a-type and rbs3b-type. Rbs3a-type resistance confers a high level of resistance to BSR infection, whereas rbs3b-type resistance typically confers an incomplete or moderate level of resistance to BSR infection. The source of rbs3a-type resistance can be tracked by the rbs3a haplotype or the rbs3a hidden haplotype (collectively referred to herein as "rbs3a haplotypes") as described in WO2014/150226, the contents of which are hereby incorporated by reference. Thus, the ability to identify a particular source of resistance in a soybean plant allows the breeder to predict the level of BSR resistance that will be exhibited by the soybean plant. On the other hand, the source of rbs3b- type resistance can be tracked by the rbs3b haplotype and the rbs3b hidden haplotype. While the rbs3b-type resistance phenotype cannot readily be distinguished among plants containing the rbs3b haplotype from plants containing the rbs3b hidden haplotype, it has been discovered that the rbs3b haplotype is closely linked to the frogeye resistance trait in some soybean varieties. As such, it may be desirable to distinguish soybean plants or soybean germplasms containing the rbs3b haplotype from soybean plants or soybean germplasms containing the rbs3b hidden haplotype. Thus, provided herein are marker loci that are highly associated with a particular haplotype of BSR resistance. In some embodiments, marker loci are provided that are highly associated with an rbs3a haplotype, and can be used to identify and/or select a soybean plant or soybean germplasm displaying rbs3a-type resistance to BSR infection. In other embodiments, marker loci are provided that are highly associated with an rbs3b haplotype, and can be used to identify and/or select a soybean plant or soybean germplasm displaying rbs3b-type resistance to BSR infection. In yet other embodiments, marker loci are provided that are highly associated with an rbs3b hidden haplotype, and can be used to identify and/or select a soybean plant or soybean germplasm displaying rbs3b-type resistance to BSR infection. It being understood that such marker loci can be used in combination with marker loci associated with BSR resistance derived from any rbs3 source.

A marker locus is said to be associated with a particular haplotype and/or phenotypic trait when contrasting alleles of that marker locus demarcate particular haplotypes and/or phenotypic traits. The relationship between bi-allelic markers and binary phenotypes can be evaluated using the frequency with which the alleles and phenotypes occur together. A marker that has a perfect association with a phenotypic trait, or that is 100% associated, will have one allele that always occurs in an individual with a particular trait and has an opposite allele that always occurs with the contrasting phenotype within a specified population. A marker locus has decreased association across a specific population when alleles at a locus do not perfectly correlate with a phenotype.

In some embodiments, a marker locus has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association with a particular haplotype and/or phenotypic trait. In a preferred embodiment, a marker locus has at least 80%, 81%, 82%, 83%, 84%, 85%, 86%, 87%, 88%, 89%, 90%, 91%, 92%, 93%, 94%, 95%, 96%, 97%, 98%, 99%, or more association with a particular haplotype and/or phenotypic trait. In a more preferred embodiment, a marker locus has at least 90%, 91%, 92%, 93%, 94%, 95%, 96%, 97%, 98%, 99%, or more association with a particular haplotype and/or phenotypic trait, most preferably, the marker locus has at least 95%, 96%, 97%, 98%, 99%, or more association with a particular haplotype and/or phenotypic trait. A marker locus in high association with a particular haplotype and/or phenotypic trait is found in at least 90%, preferably at least 95%, of a population analyzed for that particular haplotype and/or phenotypic trait. A marker locus in perfect association with a particular haplotype and/or phenotypic trait is found in 100% of a population analyzed for that particular haplotype and/or phenotypic trait. In other embodiments, a marker locus is said to have association between two phenotypic traits or haplotypes, it being understood that the percent association with one of the phenotypic traits can be the same percent association or a different percent association with the other phenotypic trait. For example, a marker locus may have at least 70% association between soybean plants with resistance to BSR infection and soybean plants with susceptibility to BSR infection, it being understood that one given allele of such marker locus has at least 70% association with the BSR resistance phenotype and a different allele of such marker locus has at least 70% association with the BSR susceptibility phenotype. In some embodiments, a marker locus has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association with BSR resistance and at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association with BSR susceptibility. In other embodiments, a marker locus has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association between BSR resistant soybean plants and BSR susceptible plants. Likewise, in some embodiments, a marker locus has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association with particular haplotype of interest, e.g., an rbs3a haplotype, an rbs3b haplotype, or an rbs3b hidden haplotype, and at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association with an offtype, i.e., a haplotype or phenotype that is different from such particular haplotype of interest. In other embodiments, a marker locus has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more association between a particular haplotype of interest e.g., an rbs3a haplotype, an rbs3b haplotype, or an rbs3b hidden haplotype, and an offtype.

Also provided are methods for selecting soybean plants for improved resistance to BSR infection comprising extracting genomic DNA samples from a population of genetically diverse plants and admixing the genomic DNA with a polynucleotide, such as a probe, capable of hybridizing to a favorable allele of a marker locus associated with BSR resistance. In certain embodiments, the method comprises detecting the presence of the hybridized polynucleotide in one or more DNA samples as an indication that the soybean plant from which the DNA sample was extracted contains the allele associated with BSR resistance. In other embodiments, soybean plants that are selected as containing a favorable allele of one or more marker locus associated with BSR resistance are crossed to soybean plants to produce progeny soybean germplasm with improved resistance to BSR infection.

Also provided are isolated polynucleotides and kits for use in identifying and/or detecting a soybean plant or soybean germplasm that displays improved resistance to BSR infection.

In certain embodiments, soybean plants or germplasm are identified that have at least one favorable allele, marker locus, haplotype or marker profile that positively correlates with resistance to BSR infection. However, in other embodiments, it is useful for exclusionary purposes during breeding to identify alleles, marker loci, haplotypes, or marker profiles that negatively correlate with resistance to BSR infection, for example, to eliminate such plants or germplasm from subsequent rounds of breeding. In some aspects, a method of selecting a soybean plant or soybean germplasm having improved resistance to BSR infection is provided that includes detecting at least one allele of one or more marker locus within or linked to a QTL associated with resistance to BSR infection, whereby the selected soybean plant or soybean germplasm has improved resistance to BSR infection.

These findings have important implications for soybean production, as identifying markers that can be used for screening soybean plants or soybean germplasms for BSR resistance derived from any rbs3 source will greatly expedite the development of such resistance into elite cultivars.

Marker loci suitable for use in the present methods are described herein.

Marker Loci Useful for the Detection of BSR Resistance Derived from any Rbs3 Source In a particular embodiment, a method for selecting a soybean plant or soybean germplasm having improved resistance to BSR infection is provided that includes the detection of at least one allele of one or more marker locus linked to a QTL associated with resistance to BSR infection. In such an embodiment, the allele positively correlates with resistance to BSR infection and enables the identification and/or selection of a soybean plant or soybean germplasm with improved resistance to BSR infection.

In some embodiments, the marker locus is associated with resistance to BSR infection in a soybean plant or soybean germplasm comprising any of the rbs3 haplotypes, e.g., an rbs3a haplotype, an rbs3b haplotype or an rbs3b hidden haplotype. In other aspects, the marker locus is associated with resistance to BSR infection in a soybean plant or soybean germplasm having either rbs3a-type resistance or rbs3b-type resistance. In yet other embodiments, the marker locus is associated with resistance to BSR infection derived from any rbs3 source. In some embodiments, the marker locus comprises an allele in linkage disequilibrium with and has at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% association with a resistance to BSR infection phenotype. In a preferred embodiment, the marker locus has at least 90%, more preferably at least 95%, association between a BSR resistance phenotype and a BSR susceptible phenotype. Thus, the detection of an allele of one or more of these marker loci, wherein the allele positively correlates with BSR resistance, enables the identification and/or selection of soybean plants that display BSR resistance derived from any rbs3 source without the need to analyze multiple marker loci and/or haplotypes.

In some embodiments, at least one allele of one or more marker locus linked to a QTL associated with resistance to BSR infection is provided, wherein the maker locus is localized on chromosome 16 (LG-J), such as one or more of the marker loci provided in FIGS. 1A-1C. In addition, a non-limiting list of additional marker loci localized on chromosome 16 and that are particularly suitable for use in the present methods is provided in Table 1.

TABLE 1

Non-Limiting Embodiments of Marker Loci localized on chromosome 16 of soybean and suitable for detecting BSR resistance derived from any rbs3 source.

| Marker Locus | Map position (cM)* | Physical position (bp)* | Allele (Res/Sus) | Reference Sequence [Res/Sus] | SEQ ID NO |
|---|---|---|---|---|---|
| Gm16: 32543279 | 83.99 | 32543279 | C/A | CCATATACATACCCAAGTGTGGTACTATGATA ATATTGGATAATMAAAAAATAGTAATAGAAW AATGATAGTTCTTTGGGCAGCACAAAGTAAAT GCTAA[C/A]ATAAATCAGACACCAGGTGAATA TACTAAAGTTTAGCAAATAATGGTACGGCAG AGTAATTGAATACATGAACYAAAAATYCTTTT TTGCTAATTGAAAT | 1 |
| Gm16: 32544128 | 83.99 | 32544128 | T/A | TGGTGCATTCTGAAAATAAACAGAACAAGAA ATGAGTTTGAAATTCAGTTCCATTAAAATGCA TAARTTTTGGTTTCACTAAAAGGGGATGGAAC AAATG[T/A]GAATAGAGCAAAATGTTTCCCAT TTGGTTCTATTTGCACAMCAAATGCTGCCMAA AAGTCTTCTTTCTCTATTTCATAACAATCATCA CCATTTTATCTC | 2 |
| Gm16: 32544169 | 83.99 | 32544169 | A/C | AATTCAGTTCCATTAAAATGCATAARTTTTGG TTTCACTAAAAGGGGATGGAACAAATGWGAA TAGAGCAAAATGTTTCCCATTTGGTTCTATTT GCACA[A/C]CAAATGCTGCCMAAAAGTCTTCT TTCTCTATTTCATAACAATCATCACCATTTTAT CTCATTTTGAAGTGATGCAGTCATGTGATTTA CAGAACCAAAAC | 3 |
| Gm16: 32545642 | 84.01 | 32545642 | A/T | AGTAAAAAAATTTAAAAATAAAATCTACTGCT AGGAAATTAAAATTAAAATAGAAAACAAAAA CAATGTTTGGAAATCAAACAGATTCTGAGTCA TCACC[A/T]CATCTCCATTTGGGATACCCATGT AATTGAGTTTTGCYCTCTATGCAACTAAGGTT CACTATAAAGATATTAACCACACTCTGCTGAC CTAATTAAAGCT | 4 |
| Gm16: 32544181 | 83.99 | 32544181 | A/C | TTAAAATGCATAARTTTTGGTTTCACTAAAAG GGGATGGAACAAATGWGAATAGAGCAAAAT GTTTCCCATTTGGTTCTATTTGCACAMCAAAT | 5 |

TABLE 1-continued

Non-Limiting Embodiments of Marker Loci localized on chromosome 16 of soybean and suitable for detecting BSR resistance derived from any rbs3 source.

| Marker Locus | Map position (cM)* | Physical position (bp)* | Allele (Res/Sus) | Reference Sequence [Res/Sus] | SEQ ID NO |
|---|---|---|---|---|---|
| | | | | GCTGCC[A/C]AAAAGTCTTCTTTCTCTATTTCA TAACAATCATCACCATTTTATCTCATTTTGAA GTGATGCAGTCATGTGATTTACAGAACCAAAA CAGAATTAATTTT | |
| Gm16: 32545680 | 84.01 | 32545680 | T/C | TTAAAATTAAAATAGAAAACAAAAACAATGT TTGGAAATCAAACAGATTCTGAGTCATCACC WCATCTCCATTTGGGATACCCATGTAATTGAG TTTTGC[T/C]CTCTATGCAACTAAGGTTCACTA TAAAGATATTAACCACACTCTGCTGACCTAAT TAAAGCTAACAAGACCCAAACAGCATGAKGT AGAAAGTCAAGCCC | 6 |
| Gm16: 32291307 | 82.94 | 32291307 | A/G | TAACTCTAATCAATATTTCATTCTTAGTCAGC ATGAATCATTTTTTYTTCTTCTTCTTATATTTA AGACCAGAATAATATATTTGAATAGAGTGAA ATAA[A/G]TACATGATAACGAGATATAAGATT AGTCTAATGACGAAAAGAGAASAAAAGAAAA AGGATTAATAATACTAACAATTAATATTTGTC GATAAAAACACA | 7 |
| Gm16: 32543387 | 83.99 | 32543387 | T/C | AGACACCAGGTGAATATACTAAAGTTTAGCA AATAATGGTACGGCAGAGTAATTGAATACAT GAACYAAAAATYCTTTTTTGCTAATTGAAATT GTACTT[T/C]GATCTCGGCCTGTTAATAATTTA TGCATTTCAAGGGCTCTAATAAGGATTGTGTC CAGAGGGGTGAATAAAATTGCATGTGGAGTA TCGCCCCCAAAACG | 8 |
| Gm16: 32284137 | 82.9 | 32284137 | T/C | TTTCAATTTGTTAGAAAGTTCCTTAAACGGAT TAAAGTTGGGTCTGAATAGCACTCAACATAGC CTTCCCTTAAAAATTTGTTAAAGGATTTGTATT TAT[T/C]ATCTTATTACACAGGAAATAATTGTC TTTCTTTCTCCTGAATTACTTGATATAAATCTT TCATAAAATTATTATTTGTCCTGGTAATAAAC TTCTATTTC | 9 |
| Gm16: 32544094 | 83.99 | 32544094 | A/G | ATAGAACAGGATAAAATATAACATGGGTAGT CTTTGGTGCATTCTGAAAATAAACAGAACAAG AAATGAGTTTGAAATTCAGTTCCATTAAAATG CATAA[A/G]TTTTGGTTTCACTAAAAGGGGAT GGAACAAATGWGAATAGAGCAAAATGTTTCC CATTTGGTTCTATTTGCACAMCAAATGCTGCC MAAAAGTCTTCTTT | 10 |
| Gm16: 32543360 | 83.99 | 32543360 | C/T | AGCACAAAGTAAATGCTAAMATAAATCAGAC ACCAGGTGAATATACTAAAGTTTAGCAAATA ATGGTACGGCAGAGTAATTGAATACATGAAC YAAAAAT[C/T]CTTTTTTGCTAATTGAAATTGT ACTTYGATCTCGGCCTGTTAATAATTTATGCA TTTCAAGGGCTCTAATAAGGATTGTGTCCAGA GGGGTGAATAAAAT | 11 |
| Gm16: 32546349 | 84.02 | 32546349 | C/T | TGCAGATGTCAGACAAACATGGCACACCAAT GARGCCCAATATCAATTTAGTAATTAAGAYAA TAAAATCYAACAAACCTAACATGAATCCCTA WCTTTG[C/T]AAGGCCAAATAATCAGCTCCCT TAAGTTTAACCCATAAATCCATTGGAAATTCA ACTCCATCAACATGGCATCACAATAACCCCAC CAAATACATTGCAG | 12 |
| Gm16: 32324276 | 83.09 | 32324276 | T/C | TYGGATAAAGAGAAAAGAAATAAWGGATAA ACACAGACAAGAGGATGAAGAATAAAATTGT ACATACAACATCTTATATATTTGTGTAGATAT TATATTC[T/C]ACTCATGKAATTAAAGAAATA GAAGTAAAAAACTAGCAAAGTATTTW*RGTC ACAAGTGTTGTGCTCTCCAGTCCACGGCAAAA TTCTCTTCAYTTTCAT | 13 |
| Gm16: 32544455 | 84 | 32544455 | C/G | GCAAAGTCCACAAAACAAAGGTAATGAGGAT CTCCACCACGCTGCAATGAACAAGCATTTCAG CATAAAGTGGACACTGCAACTTTTGACAACTA AATAA[C/G]CAAAAGAGGAGAAGCAGGCATC | 14 |

TABLE 1-continued

Non-Limiting Embodiments of Marker Loci localized on chromosome 16 of soybean and suitable for detecting BSR resistance derived from any rbs3 source.

| Marker Locus | Map position (cM)* | Physical position (bp)* | Allele (Res/Sus) | Reference Sequence [Res/Sus] | SEQ ID NO |
|---|---|---|---|---|---|
| | | | | TGTYACAAACATTAAACTTACATGTTTCGATT CTTTGCTCACAAGTCTAACTTCTCTATAYCCA ACAAAAGGGCGGAA | |
| Gm16: 32346680 | 83.17 | 32346680 | G/A | AAGCTYYGAAACACTATATTTTTT*TTTTTCAT CCTTAATCAYGYATAACTTTCTTTTAAATTGT ATCTCACTCCTTAAAGACACTAAATTTTCACG CAC[G/A]ATGGAATGTTAATTGTGTTTCTTTTG AATGAATTGAAGAAGGACACCAACCCTTTTG ATACTATAATTG*TGTYCAAATGTCTTAAAAA GGAAGATGCAT | 15 |
| Gm16: 32543724 | 83.99 | 32543724 | G/A | ATTGAGTTCATCAACTTTATAACCTGCACACC ACCCCAACAATGTCAGAAAACACCAAGAAGT TTGGATAGTAAATRTGTGT*AAAATCGTCAAA CATAA[G/A]AAACTGTTAGGTTTGCCAACCAC GGGAGCACAGCTGACCACAATAAGCATACAC ATAGCAATGCATTATAGTTTATTGAACACTTA TTTTTGGTTCTTGT | 16 |
| Gm16: 32546343 | 84.02 | 32546343 | T/A | CACATATGCAGATGTCAGACAAACATGGCAC ACCAATGARGCCCAATATCAATTTAGTAATTA AGAYAATAAAATCYAACAAACCTAACATGAA TCCCTA[T/A]CTTTGYAAGGCCAAATAATCAG CTCCCTTAAGTTTAACCCATAAATCCATTGGA AATTCAACTCCATCAACATGGCATCACAATAA CCCCACCAAATACA | 17 |
| Gm16: 32543241 | 83.98 | 32543241 | A/T | CTATTTTAAGCAATTGGAATAATAACYTGTTA GATATCCCATATACATACCCAAGTGTGGTAGT ATGATAATATTGGATAATMAAAAAATAGTAA TAGAA[A/T]AATGATAGTTCTTTGGGCAGCAC AAAGTAAATGCTAAMATAAATCAGACACCAG GTGAATATACTAAAGTTTAGCAAATAATGGTA CGGCAGAGTAATTG | 18 |
| Gm16: 32542545 | 83.98 | 32542545 | A/G | CTTATAATATAACTTTTTTTACTATCTATTCAA TGCAATTTTTGTTTTTATTGTCTGTTTTATGCT CTTCATTGTATTGTATGGTGATTCTAAAGAAA TG[A/G]AAAATAACATTTAAACAACTYATTAT TAGGGATAGAATGATCTTATTTTGTCCATGCA TACATCTTCAAACTTCATGCAATTTACTGTTTT ATCTTAAAG | 19 |
| Gm16: 32286588 | 82.91 | 32286588 | A/G | TCATAATTATAACAATTTATGTAACASAACRA AATTATARTTTTGTTAGTTTACCAAAAAGGAT GGGTGMGTGCCAATATGGGAGGAAAGAAGCA AAATG[A/G]CTTGTATTTATGCATTTCATGCTA GGGACCAAAAGCAATTTTGGAGGAGTCAATA TCAATTCCGTTATTATTATTTGAAATGAAGGT AATATAAGATATA | 20 |
| Gm16: 32546309 | 84.02 | 32546309 | T/C | AAAATCTTGAAAACACCAGGAAATTGAATAA GGCCACATATGCAGATGTCAGACAAACATGG CACACCAATGARGCCCAATATCAATTTAGTAA TTAAGA[T/C]AATAAAATCYAACAAACCTAAC ATGAATCCCTAWCTTTGYAAGGCCAAATAAT CAGCTCCCTTAAGTTTAACCCATAAATCCATT GGAAATTCAACTCCA | 21 |
| Gm16: 32282532 | 82.89 | 32282532 | A/T | ATATCTAAAATTTTGATCRAAATCCAAATTAA ATTACTACCCAAATTAATTTTGATTTAAAATTT ACTCAAATTAATTAATTAATTAATCTACAAAC TTA[A/T]GATATGGACCCTAAAACACCTGTCCT AGGCCCAGGATCCAACAAACTACAAATACTTT GACCCAAGGGGAAAGAAAAAATTGACTCAAA AAGAGGGTTAA | 22 |
| Gm16: 32540234 | 83.95 | 32540234 | G/T | ACAAAATATGGCAGTTTTAAATTGCACTCAAG TCAATATTTGTCTACTATTAATAGTTATGTAAT TTKTATTTATTGAATTTAATTAAAATGCACTTA TA[G/T]TATAAAGATTATTATAATCATCTCAT CATGTATTATCTCCTATAGCTTTTCTAATAATT | 23 |

TABLE 1-continued

Non-Limiting Embodiments of Marker Loci localized on chromosome 16 of soybean and suitable for detecting BSR resistance derived from any rbs3 source.

| Marker Locus | Map position (cM)* | Physical position (bp)* | Allele (Res/Sus) | Reference Sequence [Res/Sus] | SEQ ID NO |
|---|---|---|---|---|---|
| | | | | ACATTAGAAAAACATATATGAAGTTATTTCTA ATAGAATG | |
| Gm16: 32346259 | 83.17 | 32346259 | T/C | TTTGGGAAAGTTTGGTTTGAACCCTAACTTGG TAAATTTGGGAATTTTATTTGGGTTGCATGAT TTATGAGTTATTAGATGTTTGTTTGGTGTATTA ATG[T/C]TTGATGGACCATTCATGTGTCTTTTA TGATGTTTAGAACTGGTTGGGAAGTCATTAAT GGCCTWGAAATTTCTAAAATTGAAACTCCCTA CATTTTRCCC | 24 |
| Gm16: 32546697 | 84.02 | 32546697 | G/C | AGAACTAGTAAAATGGAATTCAAAATGGAAC TAATTCAATGAGAAAAAATTGATTACATTAAA CCATCTAGGTGGCTGTTATATACAATATGAGA AGTAA[G/C]TAACTTGCAAATAAATTTGTAAC TAACTATACCTTTAATATAAGGTTCATTTTATT TGACAAATTCTTTTTCCAAATGAGATTATCAT GCAACCTAAGTT | 25 |
| Gm16: 32286461 | 82.91 | 32286461 | C/G | CAATAGAATCATAGGTGATATACAATAAAAW TATGATTTTGTWGTATTCTTTTTATACCCTCAC AGCMGAATAACATACAATGAAATTTGTGATT CTGTT[C/G]CAGGGTGAATTTGTAATACAAAA GAATCATAATTATAACAATTTATGTAACASAA CRAAATTATARTTTTGTTAGTTTACCAAAAAG GATGGGTGMGTGC | 26 |
| Gm16: 32542834 | 83.98 | 32542834 | G/A | AACATTAAA*AAAAAAHATGTTGACATTACAT YAAAGATAATTAAGCATGTTAAGTYCCAACA TATTTAAATTCTRAAGTTATCAATTGCATTTAA TCTT[G/A]TTATTTTACCTGTCTTTTATTCTTTC TTTCTTTCATTTCAATTTCTTATCTCTTGCTTAC AAATTAGATATATATCAACTCAAATATAAAAA GTCCTTGT | 27 |
| Gm16: 32346754 | 83.17 | 32346754 | T/C | CTTAAAGACACTAAATTTTCAGGCACRATGGA ATGTTAATTGTGTTTCTTTTGAATGAATTGAA GAAGGACACCAACCCTTTTGATACTATAATTG *TGT[T/C]CAAATGTCTTAAAAAGGAAGATGC ATGCAATAAGATTTGAGATGCYTTCTTTGGAT GATYGGTGRGGTTCTGYCACTTCTCATCCCAA AAAATGTGGTAA | 28 |
| Gm16: 32286518 | 82.91 | 32286518 | G/A | CCCTCACAGCMGAATAACATACAATGAAATT TGTGATTCTGTTSCAGGGTGAATTTGTAATAC AAAAGAATCATAATTATAACAATTTATGTAAC ASAAC[G/A]AAATTATARTTTTGTTAGTTTACC AAAAAGGATGGGTGMGTGCCAATATGGGAGG AAAGAAGCAAAATGRCTTGTATTTATGCATTT CATGCTAGGGACC | 29 |
| Gm16: 32542809 | 83.98 | 32542809 | A/G | AATAGATGTGAATGAAAATTAAAACAACATT AAA*AAAAAAHATGTTGACATTACATYAAAG ATAATTAAGCATGTTAAGTYCCAACATATTTA AATTCT[A/G]AAGTTATCAATTGCATTTAATCT TRTTATTTTACCTGTCTTTTATTCTTTCTTTCTT TCATTTCAATTTCTTATCTCTTGCTTACAAATT AGATATATAT | 30 |
| Gm16: 32545807 | 84.01 | 32545807 | A/C | AGATATTAACCACACTCTGCTGACCTAATTAA AGCTAACAAGACCCAAACAGCATGAKGTAGA AAGTCAAGCCCAAAAATAAATACAAGCCACA ATAAAA[A/C]AGAAACACTGTAAAGGCAGCAT GGAATTCCAGGAGCAGAATCTCTTATTGTTGC TGTCACTCAGTCATTGTTGCATCTATYTGAAA ATTACAGCTTAGAA | 31 |

TABLE 1-continued

Non-Limiting Embodiments of Marker Loci localized on chromosome 16 of soybean and suitable for detecting BSR resistance derived from any rbs3 source.

| Marker Locus | Map position (cM)* | Physical position (bp)* | Allele (Res/Sus) | Reference Sequence [Res/Sus] | SEQ ID NO |
|---|---|---|---|---|---|
| Gm16: 32239934 | 82.63 | 32239934 | T/A | GGTTCTAGTCTTCCGGGAAAAAAAATGTGGG AATGGGGAGGTGAGATGGRAAGAACTTTTCG TACAATWAAATTTCTCTAAGGAATACAACCA GTAACAA[T/A]TTTTCATTTTTCTCTCTTTGATA GG*TTGTGTCAAGGTTTGTGTTTGTGCCACTGG CTCACTTTGTATTTAGCATAAGAAAAGTGGAA ACGGTAAAAACT | 32 |
| Gm16: 32544481 | 84 | 32544481 | C/T | AGGATCTCCACCACGCTGCAATGAACAAGCA TTTCAGCATAAAGTGGACACTGCAACTTTTGA CAACTAAATAASCAAAAGAGGAGAAGCAGGC ATCTGT[C/T]ACAAACATTAAACTTACATGTTT CGATTCTTTGCTCACAAGTCTAACTTCTCTATA YCCAACAAAAGGGCGGAAAATATCTAAGGTG AGGTTAAGGAATA | 33 |
| Gm16: 32346987 | 83.17 | 32346987 | G/A | AAGGTCATGRTATGAGAACAAGGGGGGAYAC TACTTGGAAGTTTAAGTTCAATACTTGTCATA GGACAAAAAAGACAAAGAAAGAAATKATGTT AAGCAT[G/A]CAAAACTTGATGTCTAASTTTAT GTTTATGCTTTTGYCAATGTTGAAGTGAAGCT ACMTGTAAGGATGTTCACGAGTATGAGCCAC TMRAATTGACCCAA | 34 |
| Gm16: 32347808 | 83.17 | 32347808 | T/A | TGTTGCTTCCATGGATTTTATAAGTATATGGG GTCATGTCTAGCACTTKCTTAGACCGTGTCCC ATTAGTTTAGATTTCATGTTCTAGATTGAGTA GATT[T/A]TGGAGAATGAAGACTCTGGTCATG CAGATGYTATGTTTTTGTGAATTAATGTCTTTG GCTTATTACTTTTTAGACACTTAGTTATGTAAT TATTCTTTTA | 35 |
| Gm16: 32540201 | 83.95 | 32540201 | G/T | TTGTCACTAGTTGTTATGTATTAAATAAACTCT ACAAAATATGGCAGTTTTAAATTGCACTCAAG TCAATATTTGTCTACTATTAATAGTTATGTAAT TT[G/T]TATTTATTGAATTTAATTAAAATGCAC TTATAKTATAAAGATTTATTATAATCATCTCA TCATGTATTATCTCCTATAGCTTTTCTAATAAT TACATTAG | 36 |
| Gm16: 32546282 | 84.02 | 32546282 | A/G | CAATCCATCACATTATATTCAACCCATAAAAT CTTGAAAACACCAGGAAATTGAATAAGGCCA CATATGCAGATGTCAGACAAACATGGCACAC CAATGA[A/G]GCCCAATATCAATTTAGTAATT AAGAYAATAAAATCYAACAAACCTAACATGA ATCCCTAWCTTTGYAAGGCCAAATAATCAGC TCCCTTAAGTTTAACC | 37 |
| Gm16: 32286403 | 82.91 | 32286403 | A/T | TGTTTATACATCATTACATTCATAATCTTCKTG GTATGGGAATGCGAAAAATGTTATACAATAG AATCATAGGTGATATACAATAAAAWTATGAT TTTGT[A/T]GTATTCTTTTTATACCCTCACAGC MGAATAACATACAATGAAATTTGTGATTCTGT TSCAGGGTGAATTTGTAATACAAAAGAATCAT AATTATAACAAT | 38 |
| Gm16: 32545360 | 84.01 | 32545360 | T/C | ATTATTAGTAGAGTTATTAGTACWTTCCAGGT TAATTAAATTTTCATTTCCATAAACAATAACA AAATACTTTWAAAGAATAGGAAATTAAGGCT GTTCA[T/C]GGTTCATGTATTTTCTGTTTTTATT GGGGRAAAAAACACATTTGAAAAWGTGCTCA GTGARTTTTAATAATAATATCAGATG*AAAAA AAAATATGTTTC | 39 |
| Gm16: 32285402 | 82.9 | 32285402 | A/T | CTCAATTGGCMTGTGTGCTAGAGATTTCTGTT AAACAGTCAGTTTTCAATTATCTTTGTAGCAT GAGAGAATCATGGTATGCACATAAACGATTA GCTGC[A/T]GTGTGGAGCTGACATTATATATTA GTGGCTCCATAAAAAGTGTTTCATGATTCCTG ATTTTATGTCTTCTTCATGTTTTACTTTTAGTTC CAATAGAAGA | 40 |

TABLE 1-continued

Non-Limiting Embodiments of Marker Loci localized on chromosome 16 of soybean and suitable for detecting BSR resistance derived from any rbs3 source.

| Marker Locus | Map position (cM)* | Physical position (bp)* | Allele (Res/Sus) | Reference Sequence [Res/Sus] | SEQ ID NO |
|---|---|---|---|---|---|
| Gm16: 32544988 | 84 | 32544988 | A/G | ATAATCCACCACCACCACCCCTAGCCAACCCA AGACCACCAACTGYACTGAYTTCCCCAGAAG TAAATGAAGAAAGTTGCTGCATAAATAAACA GGATGC[A/G]TGTTTTCAAAATCAAGCAGTGA AAATGAAAGTGCCCAAAATAACCAACAGTGA AATATTTAAGACATAAGAAGATGAAGTGTTA CCCCACTCTGAAGGTA | 41 |
| Gm16: 32286428 | 82.91 | 32286428 | A/C | TCTTCKTGGTATGGGAATGCGAAAAATGTTAT ACAATAGAATCATAGGTGATATACAATAAAA WTATGATTTTGTWGTATTCTTTTTATACCCTC ACAGC[A/C]GAATAACATACAATGAAATTTGT GATTCTGTTSCAGGGTGAATTTGTAATACAAA AGAATCATAATTATAACAATTTATGTAACASA ACRAAATTATART | 42 |
| Gm16: 32283215 | 82.89 | 32283215 | T/C | AATTGAGTCTTTGGTGGTTCCAAATTTTGCGC TTTGGAAGAAAGTTGTTTTTTGTTGCTGAATG GAAATTTGAGTGTTTTGAACTATAATTTAGAA TAAG[T/C]AGGTTTGGGATGAGGAATGATAAG TATGAGTTGTTTATTTTTTTGCAAAATATAAG TACAACTTGTTAGTTATTTTTCTTCACTGCTAT TAACTGATGT | 43 |
| Gm16: 32454541 | 83.52 | 32454541 | C/T | AGATTAAATTTCTTATGTATCGACGAGCRCAT CTGTTGCATTTGTTTTATCATCTTGATATAGGT CTTCTTGTATTAGRAAGACTTTTG*TTTTTAAC TG[C/T]SGGGTATGCCCCGTTTATTATTGTATC RTTTTGRGTTTAATATCATTTACRTTTTCTCCA AAACATGTTAGTTTTTGTGCCCATTCTACCTTA AGCGCTA | 44 |

*The map position and physical location on chromosome 16 (LG-J) for each of these marker loci is indicated.
Res, allele positively correlating with BSR resistance.

Sus, allele positively correlating with BSR susceptibility.

In such embodiments, the method comprises detecting at least one marker allele that positively correlates with resistance to BSR infection and enables the identification and selection of a soybean plant or soybean germplasm with improved resistance to BSR infection. In some embodiments, the one or more marker is localized within a chromosomal interval on chromosome 16 (LG-J) and has at least 90%, 91%, 92%, 93%, 94%, 95%, 96%, 97%, 98%, 99% or more association between BSR resistance and BSR susceptibility. In other embodiments, the one or more marker locus is localized within a chromosomal interval flanked by and including marker loci Sat_366 and A132_3 on chromosome 16 (LG-J) and has at least 90%, 91%, 92%, 93%, 94%, 95%, 96%, 97%, 98%, 99% or more association between BSR resistance and BSR susceptibility. In another embodiment, the one or more marker locus is localized within a chromosomal interval flanked by and including marker loci Satt244 and Satt712 on chromosome 16 (LG-J) and has at least 90%, 91%, 92%, 93%, 94%, 95%, 96%, 97%, 98%, 99% or more association between BSR resistance and BSR susceptibility. In yet another embodiment, the one or more marker locus is localized within a chromosomal interval flanked by and including marker loci Sat_224 and Sat_144 on chromosome 16 (LG-J) and has at least 90%, 91%, 92%, 93%, 94%, 95%, 96%, 97%, 98%, 99% or more association between BSR resistance and BSR susceptibility. In a preferred embodiment, the at least one allele detected is of one or more marker locus selected from the group consisting of Gm16: 32543279, Gm16:32544128, Gm16:32544169, Gm16: 32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof. In certain aspects the one or more marker locus is selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259 and a combination thereof. In a preferred embodiment, the marker locus is selected from the group consisting of Gm16:32543279, Gm16:32544128, Gm16: 32544169, Gm16:32545642, Gm16:32545680, Gm16:32291307, Gm16:32543387, Gm16:32284137, Gm16:32544094, Gm16:32543360, Gm16:32546349, Gm16:32324276, Gm16:32544455, Gm16:

32346680, Gm16:32543724, Gm16:32546343 and a combination thereof. In a more preferred embodiment, the marker locus is Gm16:32544169.

In some embodiments, the method comprises detecting one or more polymorphisms of and/or linked to one or more marker locus selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof. In certain aspects the one or more marker locus is selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259 and a combination thereof. In a preferred embodiment, the marker locus is selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343 and a combination thereof. In a more preferred embodiment, the marker locus is Gm16:32544169.

It will be appreciated that additional markers that are closely linked to a QTL associated with BSR resistance and/or closely linked to the various marker loci provided herein are also suitable for use in the present methods. Markers that map closer to the markers of the present disclosure and/or a QTL associated with BSR resistance are generally preferred over markers that map farther from the markers of the present disclosure and/or a QTL associated with BSR resistance. Thus, in one embodiment, a marker locus displays an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less with the marker locus and/or QTL to which it is linked. Thus, the marker locus is separated from the marker locus or QTL to which it is linked by about 10 cM, 9 cM, 8 cM, 7 cM, 6 cM, 5 cM, 4 cM, 3 cM, 2 cM, 1 cM, 0.75 cM, 0.5 cM, or 0.25 cM or less. Thus, in some embodiments, markers closely linked to a QTL associated with BSR resistance, and markers that are genetically linked to markers provided herein, are useful for identifying a soybean plant or soybean germplasm that displays improved resistance to BSR infection.

In further embodiments, the one or more allele detected is of one or more marker locus localizing within one or more of the genomic DNA regions of SEQ ID NOs: 1-44. In some embodiments, the one or more allele detected is of one or more marker locus localizing within 1 cM, 2 cM, 3 cM, 4 cM, 5 cM, 6 cM, 7 cM, 8 cM, 9 cM, 10 cM, 11 cM, 12 cM, 13 cM, 14 cM, 15 cM, or 30 cM of marker locus Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from marker locus Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 or a combination thereof. In yet other embodiments, the one or more marker locus is localized within a genetic recombination distance of less than or equal to 30 cM, e.g., about 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.75, 0.5, or 0.25 cM or less, from a favorable allele of marker locus Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 or a combination thereof.

In some embodiments, the method comprises detecting a haplotype or a marker profile comprising two or more polymorphisms of and/or linked to marker loci selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof.

In some aspects, the method comprises detecting one or more polymorphisms having a physical position on chromosome 16 of the soybean genome based on the *Glycine max* Williams 82 V1.1 genome sequence (Schmutz et al. 2010) (see Table 1). In such aspects, the physical position is on chromosome 16 of the soybean genome and selected from the group consisting of 32,543,279 bp, 32,544,128 bp, 32,544,169 bp, 32,545,642 bp, 32,544,181 bp, 32,545,680 bp, 32,291,307 bp, 32,543,387 bp, 32,284,137 bp, 32,544,094 bp, 32,543,360 bp, 32,546,349 bp, 32,324,276 bp, 32,544.455 bp, 32,346,680 bp, 32,543,724 bp, 32,546,343 bp, 32,543,241 bp, 32,542,545 bp, 32,286,588 bp, 32,546,309 bp, 32,282,532 bp, 32,540,234 bp, 32,346,259 bp, 32,546,697 bp, 32,286,461 bp, 32,542,834 bp, 32,346,754 bp, 32,286,518 bp, 32,542,809 bp, 32,545,807 bp, 32,239,934 bp, 32,544,481 bp, 32,346,987 bp, 32,347,808 bp, 32,540,201 bp, 32,546,282 bp, 32,286,403 bp, 32,545,360 bp, 32,285,402 bp, 32,544,988 bp, 32,286,428 bp, 32,283,215 bp, 32,454,541 bp and a combination thereof. One skilled in the art will recognize that the physical positions of the polymorphisms (i.e., SNPs) may vary when additional versions of the soybean genomic sequence are published. One skilled in the art will also appreciate that the approximate physical positions of the SNPs in Table 1 are based on a publically available genomic sequence, which may be the same or different as compared to genomic sequence for a particular soybean variety. In either case, the skilled artisan can easily determine the approximate physical positions of the SNPs provided herein on any genomic sequence using sequencing and sequence analysis techniques, such as sequence alignments, BLAST searching, and the like.

Provided herein are alleles that are favorable for, positively correlate with and/or are associated with resistance to BSR infection. In some embodiments, at least one allele of one or more marker locus positively correlates with BSR resistance and is selected from the group consisting of a BSR resistance allele of a marker locus provided in Table 1 and any combination thereof. In other embodiments, at least one allele of one or more marker loci negatively correlates with BSR resistance and is selected from the group consisting of a BSR susceptibility allele of a marker locus provided in Table 1 and any combination thereof. In yet other embodiments, an allele that positively correlates with BSR resistance and an allele that negatively correlates with BSR resistance is detected in a soybean plant or soybean germplasm (i.e., the soybean plant or soybean germplasm is heterozygous).

In some embodiments, alleles that positively correlate with BSR resistance are provided. In one embodiment, the at least one allele that positively correlates with BSR resistance comprises allele C of marker locus Gm16:32543279, allele T of marker locus Gm16:32544128, allele A of marker locus Gm16:32544169, allele A of marker locus Gm16:32545642, allele A of marker locus Gm16:32544181, allele T of marker locus Gm16:32545680, allele A of marker locus Gm16:32291307, allele T of marker locus Gm16:32543387, allele T of marker locus Gm16:32284137, allele A of marker locus Gm16:32544094, allele C of marker locus Gm16:32543360, allele C of marker locus Gm16:32546349, allele T of marker locus Gm16:32324276, allele C of marker locus Gm16:32544455, allele G of marker locus Gm16:32346680, allele G of marker locus Gm16:32543724, allele T of marker locus Gm16:32546343, allele A of marker locus Gm16:32543241, allele A of marker locus Gm16:32542545, allele A of marker locus Gm16:32286588, allele T of marker locus Gm16:32546309, allele A of marker locus Gm16:32282532, allele G of marker locus Gm16:32540234, allele T of marker locus Gm16:32346259, allele G of marker locus Gm16:32546697, allele C of marker locus Gm16:32286461, allele G of marker locus Gm16:32542834, allele T of marker locus Gm16:32346754, allele G of marker locus Gm16:32286518, allele A of marker locus Gm16:32542809, allele A of marker locus Gm16:32545807, allele T of marker locus Gm16:32239934, allele C of marker locus Gm16:32544481, allele G of marker locus Gm16:32346987, allele T of marker locus Gm16:32347808, allele G of marker locus Gm16:32540201, allele A of marker locus Gm16:32546282, allele A of marker locus Gm16:32286403, allele T of marker locus Gm16:32545360, allele A of marker locus Gm16:32285402, allele A of marker locus Gm16:32544988, allele A of marker locus Gm16:32286428, allele T of marker locus Gm16:32283215, allele C of marker locus Gm16:32454541 or any combination thereof. In a preferred embodiment, a soybean plant or germplasm comprises alleles A and A of marker locus Gm16:32544169 on chromosome 16 (i.e., the soybean plant or soybean germplasm is homozygous for an allele that positively correlates with BSR resistance at marker locus Gm16:32544169 on chromosome 16).

In some embodiments, the method comprises isolating a polynucleotide from the soybean plant or soybean germplasm. For example, a method of selecting a soybean plant or soybean germplasm having improved resistance to BSR infection is provided and comprises isolating a polynucleotide from the soybean plant or soybean germplasm. In such a method, the isolated polynucleotide comprises at least one of the alleles, marker loci, haplotypes, and/or marker profiles discussed herein. The isolation of the polynucleotide can be done using any standard DNA isolation technique known in the art.

Thus, marker loci of the present disclosure have been found to be associated with BSR resistance derived from any rbs3 source and/or tracked by any rbs3 haplotype, e.g., an rbs3a haplotype, rbs3b haplotype or an rbs3b hidden haplotype, and can be used to identify a soybean plant or soybean germplasm with improved resistance to BSR infection. The ability to use a single marker to identify and select a soybean plant or soybean germplasm having resistance or improved resistance to BSR infection regardless of the particular rbs3 source from which the resistance is derived increases the efficiency of MAS methods utilized in soybean breeding programs.

Marker Loci Associated with an rbs3a Haplotype

In some embodiments, it may be desirable to identify the particular type or source of BSR resistance in a soybean plant or soybean germplasm. WO 2014/150226 A1, the disclosure of which is hereby incorporated by reference in its entirety, demonstrates the use of multiple genetic markers to identify haplotypes corresponding to rbs3a, rbs3b, and rbs3b hidden haplotypes and the assignment of rbs3a-type or rbs3b-type resistance to various soybean varieties. However, provided herein are marker loci that are highly associated with particular BSR resistance haplotypes and enable the identification of a particular type of BSR resistance with the use of fewer markers or even a single marker. For example, in addition to selecting a soybean plant or soybean germplasm having improved resistance to BSR infection using the marker loci discussed above for the detection of a BSR resistance trait derived from any rbs3 source, provided herein are one or more marker locus associated with a particular haplotype that tracks the source from which the BSR resistance trait is derived.

In a particular embodiment, a method for selecting a soybean plant or soybean germplasm having improved resistance to BSR infection is provided that includes the detection of at least one allele of one or more marker locus associated with an rbs3a haplotype, wherein the allele positively correlates with rbs3a-type resistance to BSR infection. A non-limiting list of marker loci associated with an rbs3a haplotype and suitable for use in the present methods is provided in Table 2.

TABLE 2

Non-limiting list of marker loci associated with an rbs3a haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32297214 | 82.97 | 32297214 | G/C | *CTCACATTGCTAGAATCCCTGAGTTTCTGTA AGGTTGGTCAGAATTTGAAATGCCGAAAGT GGCCTATATGGGTTGTTGGCAGTGAATCCCA TTACACA[G/C]TACTGTTCTGGACACCAGTGT TCAAAATGAGAATGAGCTGGAACAAAGGGA ATCRCAGATTCGCAAAGCTTTYGATGCTCAA TATCAGAGCGGCGGGGGT | 45 |
| Gm16: 32340207 | 83.15 | 32340207 | T/A | TATTTAGGCAAAAAAATAGTGTTCTGTAAGA TGATGACCTTGTCAATGATTAAACCTGTGAC TGCTATATCACAAATACATTATAGGCTTCAT TTTGATT[T/A]TGAAAAGATAAGCATGAAAT GTCTCTTGATGCATTGGTTCCAGTCATATGA GAAGTAATAACTGATAATTCAATGCTGGGTT TGTAAATTGAACTGAGTA | 46 |
| Gm16: 32273397 | 82.83 | 32273397 | A/T | TTCTCTCCCCCAAGGCTTTCTTAATTCCAACC CTCTCCTTTGGCTAAAGCATAGCTTTTAGCT CCAAGGGGGATTCTCTATGTTGTAGCATTAT GATGGA[A/T]TTGGAAGTGGCGCAACAACAA ATTTTTTTATGTGGACAAGTGGGTTRCTCAA CAAGTCATTTGTTGGATTTATGCTTTGCACA ATGATATTGTTTTGGCT | 47 |
| Gm16: 32284255 | 82.9 | 32284255 | C/T | ATAATTGTCTTTCTTTCTCCTGAATTACTTGA TATAAATCTTTCATAAAATTATTATTTGTCCT GGTAATAAACTTCTATTTCGAATGAAAGTGA TCATA[C/T]ATGGAAAATATGCATTGCTTTAT ATTTAGGTTGCCTAAGTAAAACTTTTGTAAG GGGAAAATTCTTTTAGAATTTTTGTATCTGC TTCCTTTCCTGTCTC | 48 |
| Gm16: 32296634 | 82.97 | 32296634 | T/C | ACATAAACATAAATTTTATAACAGTTACATA ATTATACTATTCATAATATCCCTAATTACAA ATAAATTGGGAGATTTCTAATGTTAAGCTTG TTGACTT[T/C]AGAGTGAGCTAAATCTTGAAT TTGTGTCCATTTCTTGACCTCTTAAATTTTAA GCTAATGACA*ATCGAATGCCTTGTTTTGTC CCAAGATGTGTATAGC | 49 |
| Gm16: 32297269 | 82.97 | 32297269 | A/G | CGAAAGTGGCCTATATGGGTTGTTGGCAGTG AATCCCATTACACASTACTGTTCTGGACACC AGTGTTCAAAATGAGAATGAGCTGGAACAA AGGGAATC[A/G]CAGATTCGCAAAGCTTTYG ATGCTCAATATCAGAGCGGCGGGGGTGG*TT CGTTAGTGTAGAAGGGCTCCATCAAGTTCAT AGAGAAACAMATATCAAAC | 50 |
| Gm16: 32543353 | 83.99 | 32543353 | C/T | TTTGGGCAGCACAAAGTAAATGCTAAMATA AATCAGACACCAGGTGAATATACTAAAGTTT AGCAAATAATGGTACGGCAGAGTAATTGAA TACATGAAC[C/T]AAAAATYCTTTTTTGCTAA TTGAAATTGTACTTYGATCTCGGCCTGTTAA TAATTTATGCATTTCAAGGGCTCTAATAAGG ATTGTGTCCAGAGGGGTGA | 51 |

TABLE 2-continued

Non-limiting list of marker loci associated with an rbs3a haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32287149 | 82.91 | 32287149 | G/C | ATGGGAGATCGCTCGTGCAACTTCGTTGGAA CTAAATCAAGTGCCTGATAACAGAGAAGAT TTATCAATTTGATTCACAAATGATGCTTTTG AAACTATA[G/C]CAGCATGTATGSGTGATTCC AATTTCAAGTGGAAAGAAAAATAAGAGAAA AATTGTCAGTGTCAGTTAAAAGAAATGTAA ATTACCCGTTCCTTGCCCGT | 52 |
| Gm16: 32278942 | 82.86 | 32278942 | A/G | ATGATTTTTGCAGACAAAAGGTTAGTATCCT TGAGTCCTTTTGCTTCCATGAACAYGTTGAA CATTTGGGAAAATGTGAGGGTTGCTTATAGT ATTCTAC[A/G]CTGACGTTAATTTGATGAAGS CAACTTGCTAGTTTCTAGTTTTGATTCAAAA AGCACAATGCACTCTTCTCTTTGTAACTTTAT GGAATTTGTCCTGAAA | 53 |
| Gm16: 32297835 | 82.98 | 32297835 | G/A | TTGGTATGTAAGTTTTAAATTTGWTGGTTCT GAATTGTTGTGATGCTAATACTAAATTTATT GTGCTCTGGTTCTCAAAAGGGAAAATTGAAT ATTAATC[G/A]TATCACCACCCCATCTAACCT GGAACATGATCGATTTATCAATTGCTAATGA YAATCATCATAAAACAGGGTCCGTATGGTTG TCAAAACA*AAAAAATA | 54 |
| Gm16: 32552252 | 84.08 | 32552252 | A/C | GTTAGGAATAAAATATATTAACCGAGCA*AA AAAATCATTTAGAATTTTCTTAACAAAGTAT TATATGACTGCCTTTTATTTTTATTCCTTATT ACATGT[A/C]CTTGGATWATTTATTCATAAA ATCCTTTTAT*ATCAACAGTTTTAGTAGTAY CATTATCATGTGTGRACATTAAGAGGTCTAG CATGATCAGYGTTAAT | 55 |
| Gm16: 32297287 | 82.98 | 32297287 | C/T | GTTGTTGGCAGTGAATCCCATTACACASTAC TGTTCTGGACACCAGTGTTCAAAATGAGAAT GAGCTGGAACAAAGGGAATCRCAGATTCGC AAAGCTTT[C/T]GATGCTCAATATCAGAGCG GCGGGGGTGG*TTCGTTAGTGTAGAAGGGCT CCATCAAGTTCATAGAGAAACAMATATCAA ACTTCCACAAGAGAAGCTTG | 56 |
| Gm16: 32570539 | 84.26 | 32570539 | C/T | AAACAAAAACAAGAAAACAAAAAYAAAAA CTTGCAGACATCGAAATTAATCTGATAATAA TTGCAAAATAGTATCGCATGTATCAATGCAT TTTATATGG[C/T]CGTTATTGGAGAACTTAAA TCCAAATTTGGAAGACTTATATGTCAAGGGA AGCTAATTTAATTGGCTGAATAAAAGTGGA GAAATTATTATAAATTCCTT | 57 |
| Gm16: 32459125 | 83.54 | 32459125 | T/A | TCTTTGACGACTTTAGATCTATCGGGAAACC AGTTCACAGGGCTGCCAGTGCATCTAAGTAC AATCTCATCATATTCCTTGGGGATTCTATATT TGTCCT[T/A]CAATAAGCTGCAGGGAAACAT TCCAGAATCAATTTTCAGCCTTGTAAACCTT ACTCTCTTAGATCTATCATCAAATAATTTCA GTGGGTCTGTCCACTWT | 58 |
| Gm16: 32296468 | 82.97 | 32296468 | C/A | ATCCACACTAAGATTATTGGAAATTGCAACA ACACTGAGATCTTGAGGTCTTCCATTCAGTT CAGGTTGTTTGGATTGAAAATACTAAACCTG ATACCCA[C/A]ACCGAACAAGGCAGGGTTGA CTTTGTGGAAATCGTACGGAACCATCAACCC AAACCAACCCACATACATAAACATAAATTTT ATAACAGTTACATAATTA | 59 |
| Gm16: 32109926 | 81.71 | 32109926 | A/C | AAAAGACACTACAAGAAAGYGAAGATGTCA GAGAAGCAATGGTCAAAAGAGAAAGAAAA GAGATTARATATGTTATGGATAATAGTGAAG GTGAAAAGTG[A/C]AAAAGGATGCAGATGG AAGCAAAGAAAGACTTGRCAAAAGAGACAA CACAAGAAGGTAAAGATTTGAAAGAAGCAA TGGTCAAAAGAGAAGGCAAAGAGA | 60 |

TABLE 2-continued

Non-limiting list of marker loci associated with an rbs3a haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32562910 | 84.18 | 32562910 | A/C | TCCTTAAATTTTTAACATCCCATCTTATCCTT CTTCCTTCTCCCATCRCTCACCCTCTTTTTCT CTCCATCTTGCTCTTCCTATCTCCCCCCATTC CTTG[A/C]ATCCTGCCACAACTTCTTCCACTT CCKTCATCGCTCATCCTCCTTCTGTCACTCTC CATGAATGTTGTTTTCCAAATTTCCTATTTTG TAA*TTTTTTTT | 61 |
| Gm16: 32339979 | 83.14 | 32339979 | T/G | TTTTATATTCTTTATGGTTACATGTCAAAGA AAAGAAGAAGGTTGTTTCTTTAATTTTATAA AACATGGAGGTGGTTTGCAGAAATTTACTGT TGCATTT[T/G]CTCTTATGACACAAATCTCTT ATCTGATAAAGGACCAAATAACCAGAGAGT AGACCTCAACACTGGATAGCCATTGCTTGAT ATATATCTTTGAATGTCR | 62 |
| Gm16: 32296941 | 82.97 | 32296941 | A/T | TACAATAGCCACTTAAGTGTCATCAATGCAA AAGCATGCCTCTCAGGTATATACCAACAGA ATGTAARAATATTGCTATCATTTCAAGTGCT TCACATTT[A/T]AAAATCTGCCAGAGCATGTC TGAGTTTTTCTTCCTGCTGGATATTTTGTTG CTGGATATTGTAAACTTGCTGCTCTGTGGGC AGGCCGTCTCTAATGTC | 63 |
| Gm16: 32464136 | 83.55 | 32464136 | A/G | AATGTAATTGATTTTATAAAATTGATTTTGA AGTGATTTATGTTGGTATGTTTTATTATAAA ATTACTGGAAGTGACAAAGATGAGACCGAT ACCGAAGG[A/G]TGAAGACCAAAGATGGCC ATATGCACTACTTAGTATAATGGTTGGTGTA ATAGCAACTTCCACGAATATGTGCAATTGTG CATGTTTGGTTTTAAGATTA | 64 |
| Gm16: 32298201 | 82.98 | 32298201 | A/T | GAAAAGAAGAACCAAGTTCTGGGAGAAATT TCGGCAATAAGATGCAAAGAATAGATTGAT CTTGAATTATTAAATTTTCATTAACCACTTTT CCTAAGAG[A/T]GCTTATGTAAAATTAAAGA ATTTGTCTGAGTATGCCCATGCCTTGCYGTT GACAATGGCATAGTTGCGTTCCAATGAGAA GCTATTGAAATGTTTAATGA | 65 |
| Gm16: 32300241 | 82.99 | 32300241 | T/A | GGATAAAAATATTTCTTCATAGTGGTAAATG AGAACCGAGAGAAGAAAAATAATGAACGCA TACCTTTTATTAACCTTCTTG*TTWTTTGTAA AATCGTG[T/A]GAACTCAGCGTTAAAATATA AATGAAGAAAAG*AAAAAGGGATATRAA CTATGAAGGAAACAAATTGTGGGAAATAAA ACAGAAGCATCCTACTAGAT | 66 |

*The map position and physical location on chromosome 16 (LG-J) for each of these marker loci is indicated.
Type, allele associated with an rbs3a haplotype.
Off, allele associated with an offtype.

In some embodiments, the marker locus comprises an allele in linkage disequilibrium with and has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.75%, 99.9%, or 100% association with an rbs3a haplotype. In a preferred embodiment, the marker locus has at least 90%, more preferably at least 95%, association between an rbs3a haplotype and an offtype. Thus, the detection of an allele one of these marker loci, wherein the allele positively correlates with rbs3a-type resistance, enables the identification and/or selection of soybean plants with improved rbs3a-type resistance to BSR infection without the need to analyze multiple marker loci and/or haplotypes.

In some embodiments, at least one allele of one or more marker locus associated with an rbs3a haplotype and/or rbs3a-type resistance to BSR infection is provided, wherein the maker locus is localized on chromosome 16 (LG-J), such as one or more of the marker loci provided in FIGS. 1A-1C or Table 2. In such embodiments, the method comprises detecting at least one allele of one or more marker locus associated with an rbs3a haplotype, wherein the allele positively correlates with rbs3a-type resistance. In some embodiments, the one or more marker is localized within a chromosomal interval on chromosome 16 (LG-J) and has at least 90%, 91%, 92%, 93%, 94%, 95%, 96%, 97%, 98%, 99%, or more association between an rbs3a haplotype and an offtype. In other embodiments, the one or more marker locus is localized within a chromosomal interval flanked by and including marker loci Sat_366 and A132_3 on chromosome 16 (LG-J) and has at least 90%, 91%, 92%, 93%, 94%, 95%, 96%, 97%, 98%, 99% or more association between an rbs3a haplotype and an offtype. In another embodiment, the one or more marker locus is localized within a chromosomal interval flanked by and including marker loci Satt244 and Satt712 on chromosome 16 (LG-J) and has at least 90%, 91%, 92%, 93%, 94%, 95%, 96%, 97%, 98%, 99% or more association between an rbs3a haplotype and an offtype. In yet another embodiment, the one or more marker locus is localized within a chromosomal interval flanked by and including marker loci Sat_224 and Sat 144 on chromosome 16 (LG-J) and has at least 90%, 91%, 92%, 93%, 94%, 95%, 96%, 97%, 98%, 99% or more association between an rbs3a haplotype and an offtype. In a preferred embodiment, the at least one allele detected is of one or more marker locus selected from the group consisting of Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 and a combination thereof. In a more preferred embodiment, the at least one allele detected is of marker locus Gm16:32296634 on chromosome 16 (LG-J).

In some embodiments, the method comprises detecting one or more polymorphisms of and/or linked to one or more marker locus selected from the group consisting of Gm16: 32297214, Gm16:32340207, Gm16:32273397, Gm16: 32284255, Gm16:32296634, Gm16:32297269, Gm16: 32543353, Gm16:32287149, Gm16:32278942, Gm16: 32297835, Gm16:32552252, Gm16:32297287, Gm16: 32570539, Gm16:32459125, Gm16:32296468, Gm16: 32109926, Gm16:32562910, Gm16:32339979, Gm16: 32296941, Gm16:32464136, Gm16:32298201, Gm16: 32300241 and a combination thereof.

In further embodiments, the at least one allele detected is of one or more marker locus localizing within one or more of the genomic DNA regions of SEQ ID NOs: 45-66. In some embodiments, the one or more allele detected is of one or more marker locus localizing within 1 cM, 5 cM, 10 cM, 15 cM, or 30 cM of marker locus Gm16:32297214, Gm16: 32340207, Gm16:32273397, Gm16:32284255, Gm16: 32296634, Gm16:32297269, Gm16:32543353, Gm16: 32287149, Gm16:32278942, Gm16:32297835, Gm16: 32552252, Gm16:32297287, Gm16:32570539, Gm16: 32459125, Gm16:32296468, Gm16:32109926, Gm16: 32562910, Gm16:32339979, Gm16:32296941, Gm16: 32464136, Gm16:32298201, Gm16:32300241 or a combination thereof. In yet other embodiments, the one or more marker locus is localized within a genetic recombination distance of less than or equal to 20 cM. e.g., about 19, 18, 17, 16, 15, 14, 13, 12, 11, 10, 9, 8, 7, 6, 5, 4, 3, 2, 1, 0.75, 0.5, or 0.25 cM or less, from marker locus Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 or a combination thereof. In yet other embodiments, the one or more marker locus is localized within a genetic recombination distance of less than or equal to 30 cM, e.g., about 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.75, 0.5, or 0.25 cM or less, from a favorable allele of marker locus Gm16: 32297214, Gm16:32340207, Gm16:32273397, Gm16: 32284255, Gm16:32296634, Gm16:32297269, Gm16: 32543353, Gm16:32287149, Gm16:32278942, Gm16: 32297835, Gm16:32552252, Gm16:32297287, Gm16: 32570539, Gm16:32459125, Gm16:32296468, Gm16: 32109926, Gm16:32562910, Gm16:32339979, Gm16: 32296941, Gm16:32464136, Gm16:32298201, Gm16: 32300241 or a combination thereof.

In some embodiments, the method comprises detecting a haplotype or a marker profile comprising two or more of the polymorphisms of and/or linked to marker loci selected from the group consisting of Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 and a combination thereof.

In some aspects, the method comprises detecting one or more polymorphisms having a physical position on chromosome 16 of the soybean genome based on the *Glycine max* Williams 82 V1.1 genome sequence (Schmutz et al. 2010) (see Table 2). In such aspects, the physical position is on chromosome 16 of the soybean genome and selected from the group consisting of 32,297,214 bp, 32,340,207 bp, 32,273,397 bp, 32,284,255 bp, 32,296,634 bp, 32,297,269 bp, 32,543,353 bp, 32,287.149 bp, 32,278,942 bp, 32,297, 835 bp, 32,552,252 bp, 32,297,287 bp, 32,570,539 bp, 32,459,125 bp, 32,296,468 bp, 32,109,926 bp, 32,562,910 bp, 32,339,979 bp, 32,296,941 bp, 32,464,136 bp, 32,298, 201 bp, 32,300,241 bp and a combination thereof.

Provided herein are alleles that are favorable for, positively correlate with and/or are associated with an rbs3a haplotype and/or rbs3a-type resistance to BSR infection. In some embodiments, at least one allele of one or more marker locus positively correlates with rbs3a-type resistance to BSR infection and is selected from the group consisting of an rbs3a haplotype-associated allele of a marker provided in Table 2 and any combination thereof. In other embodiments, at least one allele of one or more marker loci negatively correlates with rbs3a-type resistance and is selected from the group consisting of an offtype allele of a marker provided in Table 2 and any combination thereof. In yet other embodiments, an allele that is associated with an rbs3a haplotype and an allele that is associated with an offtype is detected in a soybean plant or soybean germplasm (i.e., the soybean plant or soybean germplasm is heterozygous).

In some embodiments, alleles that positively correlate with rbs3a-type resistance are provided. In one embodiment, the at least one allele that positively correlates with rbs3a-type resistance comprises allele G of marker locus Gm16: 32297214, allele T of marker locus Gm16:32340207, allele A of marker locus Gm16:32273397, allele C of marker locus Gm16:32284255, allele T of marker locus Gm16:32296634, allele A of marker locus Gm16:32297269, allele C of marker locus Gm16:32543353, allele G of marker locus Gm16: 32287149, allele A of marker locus Gm16:32278942, allele G of marker locus Gm16:32297835, allele A of marker locus Gm16:32552252, allele C of marker locus Gm16:32297287, allele C of marker locus Gm16:32570539, allele T of marker locus Gm16:32459125, allele C of marker locus Gm16: 32296468, allele A of marker locus Gm16:32109926, allele A of marker locus Gm16:32562910, allele T of marker locus Gm16:32339979, allele A of marker locus Gm16:32296941, allele A of marker locus Gm16:32464136, allele A of marker locus Gm16:32298201, allele T of marker locus Gm16: 32300241 or any combination thereof. In a preferred embodiment, a soybean plant or germplasm comprises allele T of marker locus Gm16:32296634 on chromosome 16.

Thus, marker loci of the present disclosure have been found to be associated with an rbs3a haplotype and/or rbs3a-type resistance to BSR infection and can be used to identify a soybean plant or soybean germplasm with improved rbs3a-type resistance to BSR infection. The ability to use a single marker to identify and select a soybean plant or soybean germplasm having rbs3a-type resistance or improved rbs3a-type resistance to BSR infection and/or comprises an rbs3a haplotype increases the efficiency of MAS methods utilized in soybean breeding programs.

Marker Loci Associated with an rbs3b Haplotype

In some aspects, it may be desirable to distinguish rbs3b-type resistant soybean from rbs3a-type resistant soybean and/or distinguish a soybean comprising an rbs3b haplotype from a soybean comprising an rbs3b hidden haplotype. Thus, provided herein are marker loci that are associated with an rbs3b haplotype In a particular embodiment, a method for selecting a soybean plant or soybean germplasm having improved resistance to BSR infection is provided that includes the detection of at least one allele of one or more marker locus associated with an rbs3b haplotype is provided, wherein the allele positively correlates with rbs3b-type resistance to BSR infection. A non-limiting list of marker loci associated with an rbs3b haplotype and suitable for use in the present methods is provided in Table 3.

TABLE 3

Non-limiting list of marker loci associated with an rbs3b haplotype.

| Marker Locus | Map position (cM)* | Physical position (bp)* | Allele (Type/ Off) | Reference Sequence [Type/Off] | SEQ ID NO |
|---|---|---|---|---|---|
| Gm16: 32271645 | 82.82 | 32271645 | G/C | AAAGATTGAAACTTTKTCTCAAAATCAAGYTG AGAACCCTGAAACAAAGACAAACAACTAAAA AGAACACATCCTCAGTCACCAAGGAGTGAAG AAGTGY[G/C]GTAAGAAAACAAGGGAAAAAG AGAAGAAAAAGAGCGAAATCACTAAAGACAA GGATTAGTTTGTGATGWGAACTAGTTACTATG TAACSAGGCTATATAT | 67 |
| Gm16: 32271574 | 82.82 | 32271574 | T/C | AGGCTCACCGGCGAAGAAGCTCAACAACTTC TCTGATCAAAATCTTCACAAAATCTGACACCC TTAGAAGCAAAGATTGAAACTTTKTCTCAAAA TCAAG[T/C]TGAGAACCCTGAAACAAAGACAA ACAACTAAAAGAACACATCCTCAGTCACCA AGGAGTGAAGAAGTGYSGTAAGAAAACAAGG GAAAAAGAGAAGAAA | 68 |
| Gm16: 32346412 | 83.17 | 32346412 | A/C | ATTAATGGCCTWGAAATTTCTAAAATTGAAA CTCCCTACATTTTRCCCAAAAATTAAGCTCTA CACTAAGCYTGGGATTTGTGAGGCTTAGCTTA AGAAG[A/C]ACAAATTGAAGATTTAGCTCTAG GGACTTAAGGCTAAGCGWGAAATTTTCTCAA TCTTAGCATGGRCTTCRRGCTAAGTGTAGAAC TTCTCAAGCTAAGT | 69 |
| Gm16: 32339865 | 83.14 | 32339865 | T/C | ATAGAATTGTCCTTGGTTTGWCAAAAGTTAGA TTAAATTACTCTCTATCTCATTCCTWGCATTTT GTTCATATTACAGAAGGCCCTTTGAAAATTAT ACC[T/C]TCCTCATCTG*TTTTTTATATTCTTTA TGGTTACATGTCAAAGAAAAGAAGAAGGTTG TTTCTTTAATTTTATAAAACATGGAGGTGGTTT GCAGAAATT | 70 |
| Gm16: 32275584 | 82.84 | 32275584 | T/G | ATCTTTTATAAGTTTAAGTGTGTATTTGATTAT GGGTTGGGAATGTTTAGATGCACATCATTATC ATTTTTGGACAAAATAAGTAGCTTTCACGTAG TGA[T/G]GGGTGYTTACGGTTAAGTTTGGATAT TTAGTGTGAT*GATTGAGAAGTTCAATTTTGG TCAGTTTTGGAAGTTCCCTACTGTTAATGTTT GATTTTGTT | 71 |
| Gm16: 32287898 | 82.92 | 32287898 | C/T | TTATCAGTTTAACAATTGCATCTGTGGATTAT ATCACATATCTATTTATCTCCTATTTTATCAGT CATCCTTTATTCTCTGGTAAATTTTAATTCAGC AA[C/T]TGCATCCTTTATGTATGCTCCGGTAAA TTTCAACCAGAAAATAAGTCCACCGTTCAGAG TAAATTAATATGATTCAGATTCAAGAAGCTGA AACCAGAAA | 72 |
| Gm16: 32455251 | 83.52 | 32455251 | A/C | ATTAAAAAGAACCAATAGAAACAAAAGTAAG AGAAATAAAAGTCAACAACAGCCTAGGTACC TCTCCAAATACTTGCAAGCTTAATAAAATAAT GAAAAT[A/C]TAATAAAAAAAATGGAGGAAA TAGCCAACACACCTTCTATATATGACCATGCA TTGTTACATCTCTACCACAAAATATGAATATC TAATCTTATTGGAAA | 73 |

TABLE 3-continued

Non-limiting list of marker loci associated with an rbs3b haplotype.

| Marker Locus | Map position (cM)* | Physical position (bp)* | Allele (Type/ Off) | Reference Sequence [Type/Off] | SEQ ID NO |
|---|---|---|---|---|---|
| Gm16: 32346356 | 83.17 | 32346356 | A/G | ATGYTTGATGGACCATTCATGTGTCTTTTATG ATGTTTAGAACTGGTTGGGAAGTCATTAATGG CCTWGAAATTTCTAAAATTGAAACTCCCTACA TTTT[A/G]CCCAAAAATTAAGCTCTACACTAAG CYTGGGATTTGTGAGGCTTAGCTTAAGAAGM ACAAATTGAAGATTTAGCTCTAGGGACTTAAG GCTAAGCGWGAA | 74 |
| Gm16: 32570462 | 84.25 | 32570462 | T/C | GTGAAGTCATTCCTACGTAGTTATACTTATAT GTAGCTAGTTCCAAATAAGGTCAATAAAAATT TGGATGTTAGTAAAAACAAAAACAAGAAAAC AAAAA[T/C]AAAAACTTGCAGACATCGAAATT AATCTGATAATAATTGCAAAATAGTATCGCAT GTATCAATGCATTTTATATGGYCGTTATTGGA GAACTTAAATCCA | 75 |
| Gm16: 32665882 | 84.99 | 32665882 | G/C | AAAAAAAAACAACCTTGGAYCACGTAAAAGT TGTAACCCAAAAAGAAAATAGTTGGACATAG CCCAAAACGACGACGTTGCGATTCATCACTTG TGAACA[G/C]CCCCATTTCCCCACCGCAAAGT CTCATTCTGCAAAWTGGAGGCCRGTGTCTCAT CCTCTCTYGGYSTYATGAGGGAAGATCGAATT AGCTGGTTTTGAGG | 76 |
| Gm16: 32563711 | 84.19 | 32563711 | A/T | ATTGTCTTAATTGTTTCCRKGGGATTCAGGAA GCAATAGCCTTAACTTGTTCTTGAAGAGTCYA AAAARTATATTACAAAGAAATTGGGCTTTGCT TTGC[A/T]ATTGGGCTGAAAGAGGGTCTTTTCG ATCGAARCACTAATAATGAGGCATTCAGAAG GARCTGAAGACAACTAGAATATTATTAGAATT TTWGTCAATAGC | 77 |
| Gm16: 32267736 | 82.8 | 32267736 | C/T | AA*AAAAAAAACAAWTGTTTAAAAAATAAGC ACATAAAAGTAAATGCAACTCCTCCTAAGCTA GACTATTGTGGCATTGTGTTTSCTACACTTTGT TGGA[C/T]GAAGGTTAACTCCAACAATATTTTT GGGATATCTATTCAATTAAGCCATTGCCTTGG CCTTAGCTTAAGGGTTTGGCTTCCATATGGTG CAAAGCACATG | 78 |
| Gm16: 32269647 | 82.81 | 32269647 | G/T | AATCAATAAATCTCTATCCATCATCCACTRGA TTTTTCAACTTCTCAAATCTGAATAGCGCTAG GGGGTTTCATTCTTTCATAAGTTTTCCCATAAA AAT[G/T]TATACTTTCAACTACATAAACACAAC TTATCAAACATAGTTGGAAAAAAAAGGGCCAT TGTGCATCAAATGCYTTTG*AAAAAAAAAAAG TAATACRACCA | 79 |
| Gm16: 32525289 | 83.8 | 32525289 | A/G | AAAATTTATASGTTTAATTATGAAATGACGAA TATACAACATAAAAAAAC*AAAAAAAATAGC CTGTACTATGAACACTACAAGAATTTCACTCA ATAGT[A/G]AGGGAAATTAGAGAGATTTTTTT TCACTAATCGCTCAAAAATTAGCGATAGGTTT ATGAGAAACACACTTTATTTCACATTCCATTT CATATAATTTTTG | 80 |
| Gm16: 32211313 | 82.35 | 32211313 | A/T | ATGCTTTGATAAGGATAAGGACAAGTCTAGA AACCAAGTATCAAGAGAATGGACCAAAAGCT CCATTGTGGGAAGATATCTCAATTGCAATGCA AAGGCT[A/T]GGGTACAACCGGAGTGCAAAGA GATGCAAGGAAAAATGGGAGAACATCAACAA GTACTTCAAGAGAGTGAGGGAGAGTAGCAAA GAAAGGCGTGAAGATA | 81 |
| Gm16: 32347756 | 83.17 | 32347756 | T/G | CCAAATCTAACTCAACCTCGCTTGTGAACTCC CCTAGCTAGCTATATGTTTATGTTGCTTCCATG GATTTTATAAGTATATGGGTCATGTCTAGCA CTT[T/G]CTTAGACCGTGTCCCATTAGTTTAGA TTTCATGTTCTAGATTGAGTAGAATTWTGGAGA ATGAAGACTCTGGTCATGCAGATGYTATGTTT TTGTGAATTA | 82 |

TABLE 3-continued

Non-limiting list of marker loci associated with an rbs3b haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32271714 | 82.82 | 32271714 | A/T | CATCCTCAGTCACCAAGGAGTGAAGAAGTGY SGTAAGAAAACAAGGGAAAAAGAGAAGAAA AAGAGCGAAATCACTAAAGACAAGGATTAGT TTGTGATG[A/T]GAACTAGTTACTATGTAACSA GGCTATATATAGGATACTAAGGAAAATAWCG AAAGAACCTTAATGGTTCAATGTATGATGAAA TTAGTGTAGACCAACC | 83 |
| Gm16: 32550454 | 84.06 | 32550454 | A/G | ACCTTCGCGGAGTGAGTAACCGAAACGACGC CGAGCARCGACAAAACGGCGTCGTTTAKCTCC TCTCCGCCGTCCTTTAAAAAACTCGMRAGCAA CGACA[A/G]CAATCCGCATGCTTCGCTGATCG ATTTGGAAGATTGAAAATCGMACGCGAGAAA CTCCAAAACCTTAACMGTTTCAATCTTTGATT TCAGAGATCCGTTT | 84 |
| Gm16: 32550524 | 84.06 | 32550524 | A/C | CGTCCTTTAAAAAACTCGMRAGCAACGACAR CAATCCGCATGCTTCGCTGATCGATTTGGAAG ATTGAAAATCGMACGCGAGAAACTCCAAAAC CTTAAC[A/C]GTTTCAATCTTTGATTTCAGAGA TCCGTTTCTGAGAACAAATATCATCGCATCWA AGCATTGTTCSCGAGCGTCAAGAATCAGCTTT CGAATTCTCTCTC | 85 |
| Gm16: 32517555 | 83.73 | 32517555 | G/A | AGGAAAGAAAGACAAAGGTT*AAAAAAAGTA TAAGATAAATGTAAAATTTAGAATA*AAAA AAYTAATTAGGATTCTTATTAGATCTTCTTAG CAGAAC[G/A]ATATTTAAGTATCGATTTATAA GTCTCACTTTGACTTTSTATATGCTATTTTTAC ACTTCTACAAAAGAGGGAGGAAGAGAAAAAA CAAAATGTGAGTTT | 86 |
| Gm16: 32464778 | 83.56 | 32464778 | G/C | CTAGTTGTTCGGTAATTTGCACTCTTACGATG GTGGGTTATTATTGTACAAATTTCTGAAACCA ATTAATAGAAACTCGGGCTTAACCATATGTGC CGGT[G/C]AATAYATAACATCCATTTMTTTAA TTGATTAAGAAATCATTGACATAAACACGATA TGGCTAGGAACCTTCAATATGCATGACGCAAT GTATGACAGGGA | 87 |
| Gm16: 32315350 | 83.06 | 32315350 | A/G | CACCATTTCTACCAGAATTCATACAATTCATT AACAAATGTTTCTCATACCAAGCATGCATGAT TTCATAAATTTTAAGAAACTAAACGATTTAGA GTTT[A/G]GAAATTACGATATTACATGTGTTCA AATATAACTGCATTACCTGAAGTGAAACAACC ACTAATAAAGAAATAAAGTAATTATATATGA GATAAGATATTC | 88 |
| Gm16: 32263188 | 82.77 | 32263188 | A/C | TTTTTGTACCAATGTGCTACAAAACAATGTGA TTGTATGCCACTGGTTAAACCCAATAATATGT TCCCAGACAGATTAAGATAATCTGATACAACA ACCT[A/C]CAATATCAATTGATAAATTTCCTTA TAAGAACAATAAAGGATTTTAGTTTTCGTGCA AGGTAGAAGAACATTGCAGTTGCTGTCAAAC ATGAAGAGGAAR | 89 |
| Gm16: 32550442 | 84.06 | 32550442 | A/C | CTAACGAGTTCCACCTTCGCGGAGTGAGTAAC CGAAACGACGCCGAGCARCGACAAAACGGCG TCGTTTAKCTCCTCTCCGCCGTCCTTTAAAAA ACTCG[A/C]RAGCAACGACARCAATCCGCATG CTTCGCTGATCGATTTGGAAGATTGAAAATCG MACGCGAGAAACTCCAAAACCTTAACMGTTT CAATCTTTGATTTC | 90 |
| Gm16: 32217702 | 82.42 | 32217702 | T/C | TTCTCCCAARCCTCCATGACCAACATTGCACC TTCATGTCRCACCACCATGACCCACGAAACCC TCCTGCATCATC*AATCCACCAYTGCCTTACAT CAT[T/C]CACAAATKTATTATGAATTGAATAAT CCGTAAYATATTTATATTACAWATKGYTTAAT TCGTAATAAACAAAATGATTTATRACTTTCTY ACTCTTCATT | 91 |

TABLE 3-continued

Non-limiting list of marker loci associated with an rbs3b haplotype.

| Marker Locus | Map position (cM)* | Physical position (bp)* | Allele (Type/ Off) | Reference Sequence [Type/Off] | SEQ ID NO |
|---|---|---|---|---|---|
| Gm16: 32225387 | 82.51 | 32225387 | G/C | GATGTTTCTTTGCTTMCATTTGTGTGGTTGTAA TAAGATATTTTGATGGTATATGAAAAACACAG GAAAGCAATAAGAGCTAGCTAGGGTCTTTGG AAGT[G/C]CAAATTAAGCTCAGATTTGAGAGC ATCAGCATGGCATGGACCATCGACAGCATCA ATATTCTGTTCTGCTCTGCTTCAATCGCACCCA CTTTTTCAGATG | 92 |
| Gm16: 32552305 | 84.08 | 32552305 | C/T | ACAAAGTATTATATGACTGCCTTTTATTTTTAT TCCTTATTACATGTMCTTGGATWATTTATTCA TAAAATCCTTTTAT*ATCAACAGTTTTTAGTAG TA[C/T]CATTATCATGTGTGRACATTAAGAGGT CTAGCATGATCAGYCTTAATTAG*AAAAAATC CTTATGCTTCATTACCTCAAAAAAGCTTGAAC AACAAAGAA | 93 |
| Gm16: 32344193 | 83.16 | 32344193 | A/C | CTAGCTTAATTTCCAGAAGCTTATGACCAGCT TCCTCYAAATCAACACTAGACATAATTGCTGA GTATTTTGTCTTTCGAAGATTGACAAGATTTG TCTC[A/C]ATTTCATCTTTTATCTGCATATGTTC TTCTTCCTCTTYGTTGYCATTGTCTGACTCATC AGCATCCAAGCCTTCCTCATCATCATCCTCAG ATTCCTCAC | 94 |
| Gm16: 32349746 | 83.18 | 32349746 | A/C | TGAGGAACCCTAATGCACATTTTTCAAAAM*A AAAAAAAAAATTAAGTCTAGGGAAATTATTATT GCTTKAAATTTGTGAAGTTGCAGATTTTTTCA TTTG[A/C]GTGTTTCAAATTTAACGCATGAATA TAAACATGGCTACAATATGTAATTGCAGAGGT CRGTAAGGCGCAACGGGAAGAATTAAAGCGC CTTAGGGCAAGA | 95 |
| Gm16: 32550443 | 84.06 | 32550443 | A/G | TAACGAGTTCCACCTTCGCGGAGTGAGTAACC GAAACGACGCCGAGCARCGACAAAACGGCGT CGTTTAKCTCCTCTCCGCCGTCCTTTAAAAAA CTCGM[A/G]AGCAACGACARCAATCCGCATGC TTCGCTGATCGATTTGGAAGATTGAAAATCGM ACGCGAGAAACTCCAAAACCTTAACMGTTTC AATCTTTGATTTCA | 96 |
| Gm16: 32271035 | 82.82 | 32271035 | T/C | AGACCTTTGGCAATGATGAATATGTTGTTGGT TCATGGAATGAGGATGCTTCTCTTTTYGACGA ACTCGCATTGATCTAGGCAAATCAGAACCACC AAAA[T/C]GACCCCTACCTTGAAGCATACCTCT CTTTGACAACTTGCCTTCCATTGCTTCTCACAA TCAACAAAAACATATCAAACCAATGAACCCA TTTCACATCCA | 97 |
| Gm16: 32342403 | 83.15 | 32342403 | G/A | GATCAAAACCTTTCTTTTTTAATCATTTAGCAT GATGAGAATGTCAACGTTGATTTTTAAGATTT TCATTTAAAACCACTGTTTAGGGAAACAAAAT TAT[G/A]TAAAATGCATAAATTGATTTAATTAG TTTGGTGCTATTTCAAAATACAAGTACACTGA ACCGAAATGTCAGGCTAATGGGGCCTATGGG CTATGGGCAGT | 98 |
| Gm16: 32541245 | 83.96 | 32541245 | C/T | TACAAATTTTATACACAAACTT*AAAAATTAT AATAAAAAAATTYAATAATCACAAAAATTTA RCCATTGATCAATTGGAAAAAAA*GGTACATT TCTCT[C/T]AAAATAGGTACCCTAAAACATAA AAAATAGAATCAACTAAAATACTTGTAAACA AATGAAAGGTCTAACAATTTTCAAACAATCAK TTATTATTTACACA | 99 |
| Gm16: 32268012 | 82.8 | 32268012 | T/C | TCCCATTACCCAAAAGGTCCTTGCTAGCAAAA GTATGAGTGAGGATCATTRTATGTAATCTTAT TCTTGCATATRCAAAAAGGTTGTTTCCAAATT CAAA[T/C]TGATGACCAACCGGTTACCAAAAT ACAACTTTAARGTTGTGCTAGAGCTCASAATC ATTGATGTCTATTAGATAAAACAAGAAAAGTT GAGAAACAAAAT | 100 |

TABLE 3-continued

Non-limiting list of marker loci associated with an rbs3b haplotype.

| Marker Locus | Map position (cM)* | Physical position (bp)* | Allele (Type/ Off) | Reference Sequence [Type/Off] | SEQ ID NO |
|---|---|---|---|---|---|
| Gm16: 32516254 | 83.72 | 32516254 | A/G | GTTATAATGTTTTTATATTGGGCAACAATGAT TTGCCTTTTTTGGTGATTTTATTTTCATCTTTCA TGGAGAATTAYGATTTGAGRTGGGGCAATTA GAT[A/G]GWGAATTTTMAATCSCATATGRTAA TGTACGTAGCTCAAAGCCAAGTTCGAATTGGT CAACTAAGATGGAAGGGTGTCAGATGAATAA TTTGGAGAAGGA | 101 |
| Gm16: 32269873 | 82.81 | 32269873 | A/C | CMTGGCGCTTCAATTTTAAAGCAATACGTTCA TTCTCAATCTTCATTCTTTCATTCTCTAGCTTC AACTTTTCTAACTCVAGATCTTTTTTCCTACTA AA[A/C]TTCTGCCACTTGAATCTTTGTTTCTTC AGCTCCAACATCTCGTYTTGAATTTGTAGCTT CTGCTCTTCTAAYTGAAGTGAACGAGATTCAA CCSATTGCT | 102 |
| Gm16: 32344231 | 83.16 | 32344231 | T/C | AAATCAACACTAGACATAATTGCTGAGTATTT TGTCTTTCGAAGATTGACAAGATTTGTCTCMA TTTCATCTTTTATCTGCATATGTTCTTCTTCCTC TT[T/C]GTTGYCATTGTCTGACTCATCAGCATC CAAGCCTTCCTCATCATCATCCTCAGATTCCTC ACCCAGCATTGATTTCTTCAACTCTTTATAAC GCTTTTCT | 103 |
| Gm16: 32550578 | 84.06 | 32550578 | T/A | ATTTGGAAGATTGAAAATCGMACGCGAGAAA CTCCAAAACCTTAACMGTTTCAATCTTTGATT TCAGAGATCCGTTTCTGAGAACAAATATCATC GCATC[T/A]AAGCATTGTTCSCGAGCGTCAAG AATCAGCTTTCGAATTCTCTCTCCAGTTGACTT TCCGTTTTCTCGGAAAACTGAACCGAGAAGAT AGATCGCGTTTT | 104 |
| Gm16: 32346483 | 83.17 | 32346483 | G/A | YTGGGATTTGTGAGGCTTAGCTTAAGAAGMA CAAATTGAAGATTTAGCTCTAGGGACTTAAGG CTAAGCGWGAAATTTTCTCAATCTTAGCATGG RCTTC[G/A]RGCTAAGTGTAGAACTTCTCAAGC TAAGTGTGAGAGAGGAAGTAAAGGGCTTGAG CATTCTAAGCTTRAAGCTAAACGTGAGAACAT TCTAGTTGGAAGC | 105 |
| Gm16: 32573101 | 84.28 | 32573101 | T/C | GGAAATGGAAGGTTAAATGGGTAGGGGTGGT TCCTTGACCAAAATTATCAGAACTGATGATTT TATATACACTAAACTACAACATGTAAAGGGC ATATGC[T/C]CAAATTAAATGGAAGACAGATA ATTTAAGAGAAAAAGAGGAAAGGGGAAAAA AGAAGAGTGAGAAGAGAATAAGGATGGACAT AAGAACCACCAACAAAC | 106 |
| Gm16: 32217820 | 82.42 | 32217820 | T/C | TTGAATAATCCGTAAYATATTTATATTACAWA TKGYTTAATTCGTAATAAACAAAATGATTTAT RACTTTCTYACTCTTCATTTTAAGTTGTCTTTC ATT[T/C]CATTTTAAATTCCTACAAAATAARCC ATCAAATAAGCACATATAACCTATCAAAATG ATAAACTAAAGAGAAAAATAACATATTTATA AATTTATAAGTA | 107 |
| Gm16: 32324084 | 83.09 | 32324084 | T/C | TTCTACACCTTTTWGTTATATTCTTTCCATACA CCTACTTTATGGTCATTGATGATGATACTTTA GCCTT*AAAAAACATCAAATGACACCCCTGAC TTA[T/C]GAATAAAGTTTAGGTTCSGTAAGGAG TCTTGGCAACCACCAAATCAAGGACCAAAGA GAAACACCTTGTCTGTCCAAAGCTCTAAGCAA ATTYGGATAAA | 108 |
| Gm16: 32346915 | 83.17 | 32346915 | T/C | GGTGRGGTTCTGYCACTTCTCATCCCAAAAAA TGTGGTAAAGRCTSCTCGAGTCRGAGGGTGAA ATAAATGCAAGGTCATGRTATGAGAACAAGG GGGGA[T/C]ACTACTTGGAAGTTTAAGTTCAA TACTTGTCATAGGACAAAAAGACAAAGAAA GAAATKATGTTAAGCATRCAAAACTTGATGTC TAASTTTATGTTTA | 109 |

TABLE 3-continued

Non-limiting list of marker loci associated with an rbs3b haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32324102 | 83.09 | 32324102 | C/G | TATTCTTTCCATACACCTACTTTATGGTCATTG ATGATGATACTTTAGCCTT*AAAAAACATCAA ATGACACCCCTGACTTAYGAATAAAGTTTAGG TTC[C/G]GTAAGGAGTCTTGGCAACCACCAAA TCAAGGACCAAAGAGAAACACCTTGTCTGTCC AAAGCTCTAAGCAAATTYGGATAAAGAGAAA AGAAATAAWGGA | 110 |

*The map position and physical location on chromosome 16 (LG-J) for each of these marker loci is indicated.
Type, allele associated with an rbs3b haplotype.
Off, allele associated with an offtype.

In some embodiments, the marker locus comprises an allele in linkage disequilibrium with and has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.75%, 99.9%, or 100% association with an rbs3b haplotype. In a preferred embodiment, the marker locus has at least 90%, more preferably at least 95%, association between an rbs3b haplotype and an offtype. Thus, the detection of an allele of one of these marker loci, wherein the allele positively correlates with rbs3b-type resistance, enables the identification and/or selection of soybean plants with improved rbs3b-type resistance to BSR infection without the need to analyze multiple marker loci and/or haplotypes.

In some embodiments, at least one allele of one or more marker locus associated with an rbs3b haplotype and/or rbs3b-type resistance to BSR infection is provided, wherein the maker locus is localized on chromosome 16 (LG-J), such as one or more of the marker loci provided in FIGS. 1A-1C or Table 3. In such embodiments, the method comprises detecting at least one allele of one or more marker locus associated with an rbs3b haplotype, wherein the allele positively correlates with rbs3b-type resistance. In some embodiments, the one or more marker is localized within a chromosomal interval on chromosome 16 (LG-J) and has at least 90%, 91%, 92%, 93%, 94%, 95%, 96%, 97%, 98%, 99% or more association between an rbs3b haplotype and an offtype. In other embodiments, the one or more marker locus is localized within a chromosomal interval flanked by and including marker loci Sat_366 and A132_3 on chromosome 16 (LG-J) and has at least 90%, 91%, 92%, 93%, 94%, 95%, 96%, 97%, 98%, 99% or more association between an rbs3b haplotype and an offtype. In another embodiment, the one or more marker locus is localized within a chromosomal interval flanked by and including marker loci Satt244 and Satt712 on chromosome 16 (LG-J) and has at least 90%, 91%, 92%, 93%, 94%, 95%, 96%, 97%, 98%, 99% or more association between an rbs3b haplotype and an offtype. In yet another embodiment, the one or more marker locus is localized within a chromosomal interval flanked by and including marker loci Sat_224 and Sat_144 on chromosome 16 (LG-J) and has at least 90%, 91%, 92%, 93%, 94%, 95%, 96%, 97%, 98%, 99% or more association between an rbs3b haplotype and an offtype. In a preferred embodiment, the at least one allele detected is of one or more marker locus selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof. In a more preferred embodiment, the at least one allele detected is of marker locus Gm16:32271574 on chromosome 16 (LG-J).

In some embodiments, the method comprises detecting one or more polymorphisms of and/or linked to one or more marker locus selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof.

In further embodiments, the at least one allele detected is of one or more marker locus localizing within one or more of the genomic DNA regions of SEQ ID NOs: 67-110. In some embodiments, the one or more allele detected is of one or more marker locus localizing within 1 cM, 5 cM, 10 cM, 15 cM, or 30 cM of marker locus Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:

32516254, Gm16:32269873, Gm16:32344231, Gm16:32550578, Gm16:32346483, Gm16:32573101, Gm16:32217820, Gm16:32324084, Gm16:32346915, Gm16:32324102 or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from marker locus Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 or a combination thereof. In yet other embodiments, the one or more marker locus is localized within a genetic recombination distance of less than or equal to 30 cM, e.g., about 29, 28, 27, 26, 25, 24, 23, 22, 21, 20, 19, 18, 17, 16, 15, 14, 13, 12, 1, 10, 9, 8, 7, 6, 5, 4, 3, 2, 1, 0.75, 0.5, or 0.25 cM or less, from a favorable allele of marker locus Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 or a combination thereof.

In some embodiments, the method comprises detecting a haplotype or a marker profile comprising two or more polymorphisms of and/or linked to marker loci selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof.

In some aspects, the method comprises detecting one or more polymorphisms having a physical position on chromosome 16 of the soybean genome based on the *Glycine max* Williams 82 V1.1 genome sequence (Schmutz et al. 2010) (see Table 3). In such aspects, the physical position is on chromosome 16 of the soybean genome and selected from the group consisting of 32,271,645 bp, 32,271,574 bp, 32,346,412 bp, 32,339,865 bp, 32,275,584 bp, 32,287,898 bp, 32,455,251 bp, 32,346,356 bp, 32,570,462 bp, 32,665,882 bp, 32,563,711 bp, 32,267,736 bp, 32,269,647 bp, 32,525,289 bp, 32,211,313 bp, 32,347,756 bp, 32,271,714 bp, 32,550,454 bp, 32,550,524 bp, 32,517,555 bp, 32,464,778 bp, 32,315,350 bp, 32,263,188 bp, 32,550.442 bp, 32,217,702 bp, 32,225,387 bp, 32,552,305 bp, 32,344,193 bp, 32,349,746 bp, 32,550,443 bp, 32,271,035 bp, 32,342,403 bp, 32,541,245 bp, 32,268,012 bp, 32,516,254 bp, 32,269,873 bp, 32,344,231 bp, 32,550,578 bp, 32,346,483 bp, 32,573,101 bp, 32,217,820 bp, 32,324,084 bp, 32,346,915 bp, 32,324,102 bp and a combination thereof.

Provided herein are alleles that are favorable for, positively correlate with and/or are associated with an rbs3b haplotype and/or rbs3b-type resistance to BSR infection. In some embodiments, at least one allele of one or more marker locus positively correlates with rbs3b-type resistance to BSR infection and is selected from the group consisting of an rbs3b haplotype-associated allele of a marker locus provided in Table 3 and any combination thereof. In other embodiments, at least one allele of one or more marker loci negatively correlates with rbs3b-type resistance to BSR infection and/or is not associated with an rbs3b haplotype and is selected from the group consisting of an offtype allele of a marker locus provided in Table 3 and any combination thereof. In yet other embodiments, an allele that is associated with an rbs3b haplotype and an allele that is associated with an offtype is detected in a soybean plant or soybean germplasm (i.e., the soybean plant or soybean germplasm is heterozygous).

In some embodiments, alleles that positively correlate with rbs3b-type resistance are provided. In one embodiment, the at least one allele that positively correlates with rbs3b-type resistance comprises allele G of marker locus Gm16:32271645, allele T of marker locus Gm16:32271574, allele A of marker locus Gm16:32346412, allele T of marker locus Gm16:32339865, allele T of marker locus Gm16:32275584, allele C of marker locus Gm16:32287898, allele A of marker locus Gm16:32455251, allele A of marker locus Gm16:32346356, allele T of marker locus Gm16:32570462, allele G of marker locus Gm16:32665882, allele A of marker locus Gm16:32563711, allele C of marker locus Gm16:32267736, allele G of marker locus Gm16:32269647, allele A of marker locus Gm16:32525289, allele A of marker locus Gm16:32211313, allele T of marker locus Gm16:32347756, allele A of marker locus Gm16:32271714, allele A of marker locus Gm16:32550454, allele A of marker locus Gm16:32550524, allele G of marker locus Gm16:32517555, allele G of marker locus Gm16:32464778, allele A of marker locus Gm16:32315350, allele A of marker locus Gm16:32263188, allele A of marker locus Gm16:32550442, allele T of marker locus Gm16:32217702, allele G of marker locus Gm16:32225387, allele C of marker locus Gm16:32552305, allele A of marker locus Gm16:32344193, allele A of marker locus Gm16:32349746, allele A of marker locus Gm16:32550443, allele T of marker locus Gm16:32271035, allele G of marker locus Gm16:32342403, allele C of marker locus Gm16:32541245, allele T of marker locus Gm16:32268012, allele A of marker locus Gm16:32516254, allele A of marker locus Gm16:32269873, allele T of marker locus Gm16:32344231, allele T of marker locus Gm16:32550578, allele G of marker locus Gm16:32346483, allele T of marker locus Gm16:32573101, allele T of marker locus Gm16:32217820, allele T of marker locus Gm16:32324084, allele T of marker locus Gm16:32346915, allele C of marker locus Gm16:32324102 or any combination thereof. In a preferred embodiment, a soybean plant or germplasm comprises allele T of marker locus Gm16:32271574 on chromosome 16.

Thus, marker loci of the present disclosure have been found to be associated with an rbs3b haplotype and/or rbs3b-type resistance to BSR infection and can be used to identify a soybean plant or soybean germplasm with improved rbs3b-type resistance to BSR infection.

The ability to use a single marker to identify and select a soybean plant or soybean germplasm having rbs3b-type resistance or improved rbs3b-type resistance to BSR infection and/or comprises an rbs3b haplotype increases the efficiency of MAS methods utilized in soybean breeding programs.

Marker Loci Associated with an rbs3b Hidden Haplotype

In some aspects, it may be desirable to distinguish rbs3b-type resistant soybean from rbs3a-type resistant soybean and/or distinguish soybean comprising an rbs3b hidden haplotype from a soybean comprising an rbs3b haplotype. Thus, provided herein are marker loci that are associated with an rbs3b hidden haplotype In a particular embodiment, a method for selecting a soybean plant or soybean germplasm having improved resistance to BSR infection is provided that includes the detection of at least one allele of one or more marker locus associated with an rbs3b hidden haplotype is provided, wherein the allele positively correlates with rbs3b-type resistance to BSR infection. A non-limiting list of marker loci associated with an rbs3b hidden haplotype and suitable for use in the present methods is provided in Table 4.

TABLE 4

Non-limiting list of marker loci associated with an rbs3b hidden haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32234335 | 82.59 | 32234335 | G/A | TTCCATCATCAAATTCTCACCGTTATTATCA GCTTTGTTGATTTCCACATTACTCACCACTAT TTGTTGTTGTTGTTGTAGTTGTGGGACCAAT GGCTGC[G/A]CTTGTGGGGCCTCAGGAACTG TTGTTGTTTGTGCTTGTTGTGGTGTTGGAGTT GATGTTGGTGTTGCTTGTGGCACTGGTTGCT GTGGAACAACAGTGAT | 111 |
| Gm16: 32233691 | 82.59 | 32233691 | A/T | TTTTTCCGACAATATGTGAATTCAAATTGAT CCATCATTCTTTAATTGATGCCCTTTTTGGTC AATATTTTTTCCTCTCACTCTCCGGAAGCATC AGCTG[A/T]GGCTGGTTTGCTCGCAACTATCT CATAATTATCACCTCCTTCGTCGTCCTCATCC TCGTCTTCATCTCCAATTTCCTTGTCGTCCTC GTCATCCTCATTC | 112 |
| Gm16: 32235048 | 82.6 | 32235048 | C/T | GTGTTGATGGTGGTGTTATGTTGAGAATGCT TTGAGGCATAGGAAGTGATGTTGTGGATGG AACAGTGGTGTTGTTGTTGTTATTAGACACT GGTGGCAA[C/T]GGAAGTGGCATTATTATTG ATGATGGTGTAGTTGTAGTTGTTGTTACCAC TATTGACACTGGTGTTGCTGATAGTGCTGTT GTTTGTGGTGGCGGCTTTG | 113 |
| Gm16: 32297045 | 82.97 | 32297045 | T/G | ATCTGCCAGAGCATGTCTGAGTTTTTCTTCC TGCTGGATATTTTGTTGCTGGATATTGTAAA CTTGCTGCTCTGTGGGCAGGCCGTCTCTAAT GTCTTT[T/G]ATGGGAGGATGGATTTAGGTG GAGGAATGTTTCTAAAAGGTAWATCCCAGT ATGTGGAAGTTGGATTT*CTCACATTGCTAG AATCCCTGAGTTTCTGTA | 114 |
| Gm16: 32301650 | 83 | 32301650 | C/T | CAACGGGTCAAGTAAAAGTGCTGAAGCAAA ATGTGTAGAGAGGGAAAGACAAACACTTCT CAACTTCAAACAAGGCCTCATAGATGCCTCT GGCATGCTG[C/T]CTTCATGGAGGGATGATG ACAATAATAAAGATTGYTGCAAATGGAAAG GCATTGAATGCAACAATRAAACTGGTCACAT AGACATGCTTGATCTTCGKGG | 115 |
| Gm16: 32217515 | 82.42 | 32217515 | G/A | CAACACTCCAAGGTCATTTGTATATTGTTTT RGCCCACAATACACTCATCTTAAKGWGTCC ATTTATCYAACTAGAGTAAATAYATTTGTTC AAAGGGAA[G/A]TTACTTAGCACACCCCATT TTTTGCTTGATGCATCCCATATTTTCTAAAAT CCCCTTCTTACCCTTCTTCTCCCAAGCAATGC CTCTTCTCCCAARCCTC | 116 |

TABLE 4-continued

Non-limiting list of marker loci associated with an rbs3b hidden haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32308185 | 83.04 | 32308185 | G/A | GGAGAGGCATTCAATGCAAYGATGAAACTG GTCACGTACAAGTACTCAATCTTCATTGTCC AGATAGACATTATTTGACAGGTGCAATMAA TCTCACTTC[G/A]TTGATTCACTTGCAAAACA TTGAACATCTGATCTCAGCAATAATGATTTT TTACGATGTTACMTMCCGGAAGCCATGGGC TCCTTCACCAACTYRAGATA | 117 |
| Gm16: 32459325 | 83.54 | 32459325 | C/A | TCGACTTTTCTCCAAGCTTCAAATTTTGGAA AACCTTGACCTTTCACAGAATGATCARTTAT CACTAAATTTCAAATCCAATGTCAATTATAG TTTCTCC[C/A]GGTTAAGGAGTTTGGACTTAT CTTCTATGGATTTAACTGAATTTCCGAAATT ATCTGGAAAAGTCCCAAATTTAATGTTTATC TATTTGTCCAACAACAA | 118 |
| Gm16: 32288737 | 82.92 | 32288737 | C/T | AAATTTTACCTTTCTTTGGGATCTGCACAGA GAATCATACATCAAATGATTACCATATACCT CAAGTAACCCACTGATGGCGTGGATATACGT GTGTTTA[C/T]ACTCTATAGTCTATATGAATT AATACACTAMCTTTCTCTGCCTTAAATTAGG TAAATATSAATACAGCTCAAGCACTTAAATA AAACTGGTGTGATGATA | 119 |
| Gm16: 32339081 | 83.14 | 32339081 | A/G | ATTTTGGGGTCCCACCAAATAGCCAAAGAC ATTATTATTATTACTATTACTAAGGGTTGTTT TTATTATGAGAAAACTGGGAAAGAAATCTT GGTTGGAT[A/G]CACTGATATTGGTTTGGAA TGTTGTGTGCTTGCAGGATTTTTGTTAGTTGG AACTGGTAATGAATTAGATTTAGTTTTTGTG TGTGYTTTTTTWATTTTG | 120 |
| Gm16: 32273554 | 82.83 | 32273554 | A/C | TCATTTGTTGGATTTATGCTTTGCACAATGAT ATTGTTTTGGCTATGCAAGATTCTGCAAGTT GAGAGATGTTGCTCTCTACTTACCCAAATGG ACTTGC[A/C]CTTTTCTTGGTATAGTTAAGCT CAATGTTGATAGTAGTTGTGTATTCCCTCGA CCCTAGTGATAGGGACTGGTGGTCTGCATCG TGACCACAACAATGTT | 121 |
| Gm16: 32268047 | 82.8 | 32268047 | A/G | TGAGTGAGGATCATTRTATGTAATCTTATTC TTGCATATRCAAAAAGGTTGTTTCCAAATTC AAAYTGATGACCAACCGGTTACCAAAATAC AACTTTAA[A/G]GTTGTGCTAGAGCTCASAAT CATTGATGTCTATTAGATAAAACAAGAAAA GTTGAGAAACAAAATCATTTTTATTCTACTC CCTATGTTCATATTTACAA | 122 |
| Gm16: 32270524 | 82.81 | 32270524 | A/T | CTTTCTCGGAAAGATAATCRATCAAATCCAA CAAAGAAGGATTTTCAACAACCCGACAGGA AGTTCCCCTCCCAAGCATAACATTAAGCTTT TTGTAGCT[A/T]TTACTAAGGTCATTGAATTT ATCCTCACATTGTTGAGGTGAAACATGGTAA CCTCTTTCAGCCATGACCTTAGAAATGGATT TCCATTTCCCTTTATTTT | 123 |
| Gm16: 32349993 | 83.18 | 32349993 | T/G | GGACAAAATTGCTCCAACTTGATGAACATCA ATTAGCAGAAGTAGCTCATAATAGCAGTAG TAATTTAATTATGAGTTTGTGTGTGGTGAGA CTTGTGAA[T/G]GGTACATTATTATGCATTTT AGTGATGTTTATTTTCTCTAATTCTGGATTGG AAGCACAACCTTTGAAATTTATGTTTTATAG CTTTTTGGATGAATGAA | 124 |
| Gm16: 32329724 | 83.11 | 32329724 | G/A | CCATCAAAACACGAGACTTRAAAGASACCC AATCTCTAGTCTCAATCTCAACYCTAMAAAT TTTAAATCACTTGGCAATACTACAAAGAAAC TGCACATA[G/A]ATGTTTCCACACACACAAA AACACAGTTGATGCTATGCTCACACATGGTT ATRSGTATTATGCAGTCAAGCCCAGTGMTTC ACACCAAGCACAGAAACCA | 125 |

TABLE 4-continued

Non-limiting list of marker loci associated with an rbs3b hidden haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32236209 | 82.61 | 32236209 | T/C | TAAAAGGAAATTAAACAAATCCAAATGAAA GAGCAAAAAACCAAGAGAGAGAGTGAGTG AGACGGAAAAAAATTAACATGGAATTGAAG TGAAACACATT[T/C]CCAAGAGAATGAAGAG ATGAAAGAACAAAACTTGAGCAAGAATTGA GAGGTTTCAGATCTCCAAGTACCCAACAACT CAAACTGGTATAGTACTCATCGA | 126 |
| Gm16: 32275786 | 82.85 | 32275786 | A/T | TTTTTAACWTGGTTGATTAGTATGTTTCGGA TGTTCTATGATTATTTTGGAGTGTTTTGATTT TGTGGTTCATTGAAAGATTGAATTTTAAGGT TTTGGA[A/T]KTTCACGGTTCTCCAATTTTAA AATCCACTGTCTGTGGGTGGTTGCTTGAGTT TTGCTTTTGCTTTTTTAAATTTTAGATGTTCT GTATGGCTGTGGGTT | 127 |
| Gm16: 32275787 | 82.85 | 32275787 | T/G | TTTTAACWTGGTTGATTAGTATGTTTCGGAT GTTCTATGATTATTTTGGAGTGTTTTGATTTT GTGGTTCATTGAAAGATTGAATTTTAAGGTT TTGGAW[T/G]TTCACGGTTCTCCAATTTTAAA ATCCACTGTCTGTGGGTGGTTGCTTGAGTTT TGCTTTTGCTTTTTTAAATTTTAGATGTTCTG TATGGCTGTGGGTTT | 128 |
| Gm16: 32218068 | 82.42 | 32218068 | T/G | CCTCAATTCACAACTCTCAATTATGT*TTTTT TGACAATTATTAAGCCACCACCCTAAAAGG AAATGATCATCTCCCTAAAATGGAAATCTAG TAAAAAC[T/G]GTTATTCTTGTGCATGCACGA AATCGTTCACATTCTTAATTTCAAATTTTCAA CTCACTCAAAAAATTAGAAGTACTTGGCACG ATGCTTCTACTCCTCC | 129 |
| Gm16: 32230177 | 82.56 | 32230177 | A/G | AGCATGGCAGTAGGTTTTGGACATTAATTGC ACTGGTTTACCTATAATCTGATGGGCCAGWT GGAGGGCATGTCTGAGTCCAGAGCAGATGA ACTTCTGA[A/G]CCTCATCAAGCTCTCCTACC TAGTTACAATGGATTTGGACAGAGTGATTAA TGACAATTGAATTGATGATATATAAGCTTAA ACATTAAAACACTGAAGA | 130 |
| Gm16: 32287161 | 82.91 | 32287161 | C/G | TCGTGCAACTTCGTTGGAACTAAATCAAGTG CCTGATAACAGAGAAGATTTATCAATTTGAT TCACAAATGATGCTTTTGAAACTATASCAGC ATGTATG[C/G]GTGATTCCAATTTCAAGTGG AAAGAAAAATAAGAGAAAAATTGTCAGTGT CAGTTAAAAGAAATGTAAATTACCCGTTCCT TGCCCGTGAAAGACTGTCC | 131 |
| Gm16: 32186606 | 82.16 | 32186606 | C/G | TAGCTAGAAGCACTATTCTAGAACAAGCTTG CAAAAAGGACTCAAGTTATCTTTTGGTAAGG GAAGCTTTAGA[C/G]CTCAAGTCTAGCTTGG AGACTTTTGATTTTGAAGCTTTGTATTTTGTA TCTTGGCTAAAGAATATATGTTGGAAAAAGT GTTCTTGAAGAGCTCTTAAAG | 132 |
| Gm16: 32338878 | 83.14 | 32338878 | A/G | TCTGCTGAAAACAATATGGTTGCAAATTATA TGAAGCTTTAAGCTTTAATGTTGCCATAAGC TTTAAGTTATTCCTCTTCAAAAAAGAAAAA* GCTTTAA[A/G]TTATTATTATATGATTGGAGA CGGCGAAGAGTTTAAGTGTGACTAACCTCG GACTGAGAAATAGTCTCGTAGTTGGCTTACA AGACAAAAAGTTGTAGCG | 133 |
| Gm16: 32182404 | 82.15 | 32182404 | G/A | AATTACAGATAGATATTCTAAACAYAGCAA GATAACTTTATACGAAATGGAGGAAACCCA TCAACAATGGTGCACATATGATTGTCTAGAA TTGATTAGG[G/A]CTGGGAATAACCATGTTT CTCGAGGTTTTCTCGTTTTAGTGGTTGATGC ATATATACTATTCTGCCGGCAAACATATGGC CATGATGATAAAAATAAGCT | 134 |

TABLE 4-continued

Non-limiting list of marker loci associated with an rbs3b hidden haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32323924 | 83.09 | 32323924 | C/T | ATGACCCGCTCAAAGACGATATGAAAACWA TAACTCCTAATTAGGATCATATCATAATCCA TGATCATGCTGAATGAGAATGACTTGTGAGA ACAATTTG[C/T]TAGTTATAGTCTGCGCGTAT CTTGGGGGGGAGGATGATTATTTAGAGAAT CATGATTTTTTCTACACCTTTTWGTTATATTC TTTCCATACACCTACTTT | 135 |
| Gm16: 32319745 | 83.08 | 32319745 | C/A | GATTTATAAGCCTCTGTCTGGACTATTTGTG AAGGGTCTAATATTGGTATAATCCCAGCATT TAGAGGAATTRCTTACTAATTTTCTTACAGG GGTGATA[C/A]AAATAGGTTTTATAATTTACT TAGACTTATCATATTAYTAAAATATGTTTGT GTGTGTTAATTTGATTAAATTTATAGAAATA GATCGTGATCCCTCTGA | 136 |
| Gm16: 32270866 | 82.82 | 32270866 | T/C | CCGCTTCATGATGACCATCAACACMTTCTTC GACTAAACTTGCATCACTTGGTGAGGTCTTG TGTATACCCCTTTGATTAAACTCAGTCATTG ACAAAAT[T/C]TGATGATCACAYTTCTGGAA GGATCCCATTGTAAGAGGCAAACCATCATG AATTGAGGAGTGCACTAAAGACCTTTGGCA ATGATGAATATGTTGTTGGT | 137 |
| Gm16: 32307865 | 83.04 | 32307865 | T/A | TATAATTTCCTCCAGAAAACCAACAGATCAT AATTCTCTCTTGCATTGGCATTATCTTGTCTT GTCCTTAGTTAAGATTATTCTTATCAGCAAA ATTATA[T/A]TGAGTAGTTATTTTCTGACAAC ATTTTATGCTCTGTTCCTGCTTTTATTTMATT CCTCAGGATTTAMTCTCGGATTAAATGGGTC ACTTMAAAGTYCTRA | 138 |
| Gm16: 32341072 | 83.15 | 32341072 | G/A | TGACTAGAATATAGAAATTGTAATTATCCAG GTATCCACCAKTAGCTCTTGCCACTATCCAT AAGAGCAAGACTCTTTGAGTAAGATATTAC AGATTCAA[G/A]ACTCAAATTGGTGTGCTTTT GCATAGTTTGGCTGAATTCAATCAAATGATT CTGACTATGTAGTATTACKATCTTAGTATTTT AGCTAAAGTCAATTTTG | 139 |
| Gm16: 32204594 | 82.27 | 32204594 | A/C | AAAAAAAAAACATTAGAAAATTATTTTTGTT TGACAACCAGGTTGTATAAAAATATAGTATG TGATTCGCAACTTACATATGTCCTTTGAAAG TAGTTAT[A/C]AACCTAATTGTTTGACTTGTT TGGGGTAACCAAGAAGAGTTCATCAGGATC CATAAATCGCCAAGTCTTATAACCTTAAATA AAAGCCAATGAATGCTTA | 140 |
| Gm16: 32288768 | 82.92 | 32288768 | C/A | GAATCATACATCAAATGATTACCATATACCT CAAGTAACCCACTGATGGCGTGGATATACGT GTGTTTAYACTCTATAGTCTATATGAATTAA TACACTA[C/A]CTTTCTCTGCCTTAAATTAGG TAAATATSAATACAGCTCAAGCACTTAAATA AAACTGGTGTGATGATAAAAAWACCATGGA TAACTAATTAAGGATACT | 141 |
| Gm16: 32454218 | 83.52 | 32454218 | A/G | CAAAACTCGCTTAAGCCCCAACTGTGCATGG CTTAAGCTCTTAGCCAACACCACTTATGCTA CATAAAAACATGTTAGTTTGCTCATTTGTTC TTTTCTT[A/G]CAGGAAATCTCTCCAAGTTTG GRYTCACATTCGTGATTTGGYTCCTTTCCGC AGACRTTTCACTTCTTTAYAGCGCATTACTG ACTCTTTAATTAGGRGC | 142 |
| Gm16: 32321898 | 83.09 | 32321898 | T/A | TCCCATTCAACGTCGGTTGTGAATCTAAGTG TTTTGACTTTGATCTTTTTTGTTCTGTGTTTTG TGTCCTTGTGATTGCTTTTAAACCTCAATATG TGTT[T/A]GTTATAGTATGGAGATATTTAAAG AAGAA*AAAAAAACAATTGTATTTTGTGATG GTTTTGATAATGTTAAATCTACATGCAGGGT CAAAATGAATTWTA | 143 |

TABLE 4-continued

Non-limiting list of marker loci associated with an rbs3b hidden haplotype.

| Marker Locus | Map position (cM)* | Physical position (bp)* | Allele (Type/Off) | Reference Sequence [Type/Off] | SEQ ID NO |
|---|---|---|---|---|---|
| Gm16: 32554984 | 84.1 | 32554984 | A/C | AAAGATTGTGGTTGAAAAAAATTCAGCAAC TAATTTTAGACGAGTCTGAATTGAGAGCAAT TCTTGATGAATGCAAAAAATTGWTTTGTTTA AATACAAA[A/C]TTTAAACTTAAAGTTCATT AAGAGTCAAGTCAATGTATAGCTAGTTGCTC AGTCTTTAGAAGGGCATCTGCATATTTATTA TTTAGCTAGCTSCATGTTC | 144 |
| Gm16: 32350129 | 83.18 | 32350129 | T/C | CTCTAATTCTGGATTGGAAGCACAACCTTTG AAATTTATGTTTTATAGCTTTTTGGATGAAT GAAAGTARCATTTCTTTTGAAGATAAGAATG AAAGTAA[T/C]ACAATAAARATGTTGAAAGA CTAGTTGATAATACTGTAGTAATTAGCTTTT GGAATTAAATAGCAATAATTTTGGAAAGCA* CTTCTCAGTACGCCTYGG | 145 |
| Gm16: 32243083 | 82.65 | 32243083 | T/A | CGSTGATGTAGCAAAAAAACTGTACC*AAAA AAAAAAAGATTTATGCAGGACATGTGTTTTT AGGCAGAGCCATTTATGAACGGAAGTTAAT AGTGACCA[T/A]TCCTGTTGGATTTGTAACCT ACCGTTATAATGGCATCAAAATTTCGATGG CAGTCGCTGCGTTCTCTATCCAAGGAGAATT ATTGGATTGCCAACCCTA | 146 |
| Gm16: 32291418 | 82.94 | 32291418 | G/A | CGAGATATAAGATTAGTCTAATGACGAAAA GAGAASAAAAGAAAAAGGATTAATAATACT AACAATTAATATTTGTCGATAAAAAACACAC AAAGTAGGG[G/A]TAGCGTACCTTGCTGACA GCGGAACAAACGAACTTGCAACCGAGAACA ATGTGACTGAGCAAGATGGTGAAATCGCCG CGTGACTCGGGGTGCTTGGATT | 147 |
| Gm16: 32213522 | 82.37 | 32213522 | G/A | AACATTTTTKAATACCGCGTCCTATGTAATA TTCTACCAATCTCATCATGYGTATGCAATTG TAGTAACTAGTAAGGCAGTTAATTTACCAAA CTTAAAC[G/A]GTACTCTTAAAAACTAAATA ATAAAGATTTKCATATTTATTACTCTACTAT CATTATTTTATAAATTTTACTATCATATTTTT AAATTTTGTTCACAAAT | 148 |
| Gm16: 32217755 | 82.42 | 32217755 | T/C | CCACGAAACCCTCCTGCATCATC*AATCCAC CAYTGCCTTACATCATYCACAAATKTATTAT GAATTGAATAATCCGTAAYATATTTATATTA CAWATKG[T/C]TTAATTCGTAATAAACAAAA TGATTTATRACTTTCTYACTCTTCATTTTAAG TTGTCTTTCATTYCATTTTAAATTCCTACAAA ATAARCCATCAAATAA | 149 |
| Gm16: 32541584 | 83.97 | 32541584 | C/T | CATAACATAATTAACTTTATTTCAAGACAGC TATTTAAAATCAGAGTTCCTTCGACATTGAA GGCTGAGGCAATTATTCAATGATTAGCATGT TTGCTTG[C/T]TCATTTTTTCACATATTTACCC AAATTTTCACRTCAAGGATGGCRCAG AGGCAAAACCAAACACATGGGATATTGGTTGTGTTT ATTTTTTCGTTAAACT | 150 |
| Gm16: 32554335 | 84.1 | 32554335 | C/T | TTCATCATTATTGTAAAAGTACATCTAATAM TAGTTGTGTTCAGAAAGCCGTTCTATACGTT CAACGGACCTCTTACACTTTCTATGTTTTGTT TTTCCC[C/T]ATATTTAAGAGAGAAGTGCCTT GTCTCARAAAAAGAAAAGAGAGAATGGTGC CTTAGAGAGAGGGKGGGAGAATTTTGTTAC ACGATACTTGTCTTCTTA | 151 |
| Gm16: 32509795 | 83.7 | 32509795 | A/T | CGGTTGATAATTTTCTAGCTGTTCATTAATR CGCTTAGATTTTATTTTTAACTTTTTATATT GGTGAATAGTATGGAGTTAAGTAGTGAATA ATGTGT[A/T]GACAATCAACAATCATTTCGTT AATAAAATAATATACATTTTTTTAACTCATT ACGTTCACCCCGTTTACTAATATCGATATAA TGTTTAAGGAGGAAAA | 152 |

TABLE 4-continued

Non-limiting list of marker loci associated with an rbs3b hidden haplotype.

| Marker Locus | Map position (cM)* | Physical position (bp)* | Allele (Type/ Off) | Reference Sequence [Type/Off] | SEQ ID NO |
|---|---|---|---|---|---|
| Gm16: 32239092 | 82.63 | 32239092 | C/T | CTCCAACACTTGAGCTAGTAATAATTTGAAT AGAACGATGATATATAAATGCATACATGAT ATTTTTAGACATTGTCTGATATATAAGATGC TTAGGATA[C/T]GTTGGATTGCCTATTACTAA GTCCAATTTGAGAGGCCTAATTATTTTGAAA TATTATTAGAATATGTTTGGATAYAAGRCTA AAATTTCTTTAGACASTT | 153 |
| Gm16: 32491511 | 83.64 | 32491511 | G/A | CAGAAAAGATGTGGTTAGTATATCTCTAAAA ATAATGTAGCATTAAGAAAAGATCGTGACT ATGCTGCAAAAGTTGTATATTGAAGTCTTGA GTCTAGAT[G/A]TGATTAATTAATTCATTGAA ATGCCAAGTCTCAAAATCCCGAATTAYACTT ATGCAAAATCACCTACTACCTTTTAGAGTCA ATTAAACCATTATTAACA | 154 |
| Gm16: 32270738 | 82.82 | 32270738 | G/T | TTTTCTTCTTTTGCTACTGTTGTCARAAGTTG CATCCTCACCTATGTAAGACATGACCATTAT YAGAAGTTTTACCATCTTATCAGTCCATTTC ACCTGC[G/T]GCCAAGGAGTACTTTTTTTCCC TTTACCCGCTTCATGATGACCATCAACACMT TCTTCGACTAAACTTGCATCACTTGGTGAGG TCTTGTGTATACCCCT | 155 |

*The map position and physical location on chromosome 16 (LG-J) for each of these marker loci is indicated.
Type, allele associated with an rbs3b hidden haplotype.
Off, allele associated with an offtype.

In some embodiments, the marker locus comprises an allele in linkage disequilibrium with and has at least 80%, 81%, 82%, 83%, 84%, 85%, 86%, 87%, 88%, 89%, 90%, 91%, 92%, 93%, 94%, 95%, 96%, 97%, 98%, 99%, 99.5%, 99.75%, 99.9%, or 100% association with an rbs3b hidden haplotype. In a preferred embodiment, the marker locus has at least 90%, more preferably at least 95%, association between an rbs3b hidden haplotype and an offtype. Thus, the detection of an allele of one or more of these marker loci, wherein the allele positively correlates with rbs3b-type resistance, enables the identification and/or selection of soybean plants that display improved rbs3b-type resistance to BSR infection without the need to analyze multiple marker loci and/or haplotypes.

In some embodiments, at least one allele of one or more marker locus associated with an rbs3b hidden haplotype and/or rbs3b-type resistance to BSR infection is provided, wherein the maker locus is localized on chromosome 16 (LG-J), such as one or more of the marker loci provided in FIGS. 1A-1C or Table 4. In such embodiments, the method comprises detecting at least one allele of one or more marker locus associated with an rbs3b hidden haplotype, wherein the allele positively correlates with rbs3b-type resistance. In some embodiments, the one or more marker is localized within a chromosomal interval on chromosome 16 (LG-J) and has at least 90%, 91%, 92%, 93%, 94%, 95%, 96%, 97%, 98%, 99% or more association between an rbs3b hidden haplotype and an offtype. In other embodiments, the one or more marker locus is localized within a chromosomal interval flanked by and including marker loci Sat_366 and A132_3 on chromosome 16 (LG-J) and has at least 90%, 91%, 92%, 93%, 94%, 95%, 96%, 97%, 98%, 99% or more association between an rbs3b hidden haplotype and an offtype. In another embodiment, the one or more marker locus is localized within a chromosomal interval flanked by and including marker loci Satt244 and Satt712 on chromosome 16 (LG-J) and has at least 90%, 91%, 92%, 93%, 94%, 95%, 96%, 97%, 98%, 99% or more association between an rbs3b hidden haplotype and an offtype. In yet another embodiment, the one or more marker locus is localized within a chromosomal interval flanked by and including marker loci Sat_224 and Sat_144 on chromosome 16 (LG-J) and has at least 90%, 91%, 92%, 93%, 94%, 95%, 96%, 97%, 98%, 99% or more association between an rbs3b hidden haplotype and an offtype. In a preferred embodiment, the at least one allele detected is of one or more marker locus selected from the group consisting of Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof. In a more preferred embodiment, the at least one allele detected is of marker locus Gm16:32234335 on chromosome 16 (LG-J).

In some embodiments, the method comprises detecting one or more polymorphisms of and/or linked to one or more marker locus selected from the group consisting of Gm16: 32234335, Gm16:32233691, Gm16:32235048, Gm16: 32297045, Gm16:32301650, Gm16:32217515, Gm16: 32308185, Gm16:32459325, Gm16:32288737, Gm16: 32339081, Gm16:32273554, Gm16:32268047, Gm16:

32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof.

In further embodiments, the at least one allele detected is of one or more marker locus localizing within one or more of the genomic DNA regions of SEQ ID NOs: 111-155. In some embodiments, the one or more allele detected is of one or more marker locus localizing within 1 cM, 5 cM, 10 cM, 15 cM, or 30 cM of marker locus Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 or a combination thereof. In yet other embodiments, the one or more marker locus is localized within a genetic recombination distance of less than or equal to 20 cM, e.g., about 19, 18, 17, 16, 15, 14, 13, 12, 11, 10, 9, 8, 7, 6, 5, 4, 3, 2, 1, 0.75, 0.5, or 0.25 cM or less, from marker locus Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 or a combination thereof. In yet other embodiments, the one or more marker locus is localized within a genetic recombination distance of less than or equal to 30 cM, e.g., about 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.75, 0.5, or 0.25 cM or less, from a favorable allele of marker locus Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 or a combination thereof.

In some embodiments, the method comprises detecting a haplotype or a marker profile comprising two or more polymorphisms of and/or linked to marker loci selected from the group consisting of Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof.

In some aspects, the method comprises detecting one or more polymorphisms having a physical position on chromosome 16 of the soybean genome based on the *Glycine max* Williams 82 V1.1 genome sequence (Schmutz et al. 2010) (see Table 4). In such aspects, the physical position is on chromosome 16 of the soybean genome and selected from the group consisting of 32,234,335 bp, 32,233,691 bp, 32,235,048 bp, 32,297,045 bp, 32,301,650 bp, 32,217,515 bp, 32,308,185 bp, 32,459,325 bp, 32,288,737 bp, 32,339,081 bp, 32,273,554 bp, 32,268.047 bp, 32,270,524 bp, 32,349,993 bp, 32,329,724 bp, 32,236.209 bp, 32,275,786 bp, 32,275,787 bp, 32,218,068 bp, 32,230,177 bp, 32,287,161 bp, 32,186,606 bp, 32,338,878 bp, 32,182,404 bp, 32,323,924 bp, 32,319,745 bp, 32,270,866 bp, 32,307,865 bp, 32,341,072 bp, 32,204,594 bp, 32,288,768 bp, 32,454.218 bp, 32,321,898 bp, 32,554,984 bp, 32,350,129 bp, 32,243,083 bp, 32,291,418 bp, 32,213,522 bp, 32,217,755 bp, 32,541,584 bp, 32,554,335 bp, 32,509,795 bp, 32,239,092 bp, 32,491,511 bp, 32,270,738 bp and a combination thereof.

Provided herein are alleles that are favorable for, positively correlate with and/or are associated with an rbs3b hidden haplotype and/or rbs3b-type resistance to BSR infection. In some embodiments, at least one allele of one or more marker locus positively correlates with rbs3b-type resistance to BSR infection and is selected from the group consisting of an rbs3b hidden haplotype associated allele of a marker locus provided in Table 4 and any combination thereof. In other embodiments, at least one allele of one or more marker loci negatively correlates with rbs3b-type resistance and/or is not associated with an rbs3b hidden haplotype and is selected from the group consisting of an offtype allele of a marker locus provided in Table 4 and any combination thereof. In yet other embodiments, an allele that is associated with an rbs3b hidden haplotype and an allele that is associated with an offtype is detected in a soybean plant or soybean germplasm (i.e., the soybean plant or soybean germplasm is heterozygous).

In some embodiments, alleles that positively correlate with rbs3b-type resistance are provided. In one embodiment, the at least one allele that positively correlates with rbs3b- type resistance comprises allele G of marker locus Gm16:32234335, allele A of marker locus Gm16:32233691, allele C of marker locus Gm16:32235048, allele T of marker locus Gm16:32297045, allele C of marker locus Gm16:32301650, allele G of marker locus Gm16:32217515, allele G of marker locus Gm16:32308185, allele C of marker locus Gm16:32459325, allele C of marker locus Gm16:32288737, allele A of marker locus Gm16:32339081, allele A of marker locus Gm16:32273554, allele A of marker locus Gm16:32268047, allele A of marker locus Gm16:32270524, allele T of marker locus Gm16:32349993, allele G of marker locus Gm16:32329724, allele T of marker locus Gm16:32236209, allele A of marker locus Gm16:32275786, allele T of marker locus Gm16:32275787, allele T of marker locus Gm16:32218068, allele A of marker locus Gm16:32230177, allele C of marker locus Gm16:32287161, allele C of marker locus Gm16:32186606, allele A of marker locus Gm16:32338878, allele G of marker locus Gm16:32182404, allele C of marker locus Gm16:32323924, allele C of marker locus Gm16:32319745, allele T of marker locus Gm16:32270866, allele T of marker locus Gm16:32307865, allele G of marker locus Gm16:32341072, allele A of marker locus Gm16:32204594, allele C of marker locus Gm16:32288768, allele A of marker locus Gm16:32454218, allele T of marker locus Gm16:32321898, allele A of marker locus Gm16:32554984, allele T of marker locus Gm16:32350129, allele T of marker locus Gm16:32243083, allele G of marker locus Gm16:32291418, allele G of marker locus Gm16:32213522, allele T of marker locus Gm16:32217755, allele C of marker locus Gm16:32541584, allele C of marker locus Gm16:32554335, allele A of marker locus Gm16:32509795, allele C of marker locus Gm16:32239092, allele G of marker locus Gm16:32491511, allele G of marker locus Gm16:32270738 or any combination thereof. In a preferred embodiment, a soybean plant or germplasm comprises allele G of marker locus Gm16:32234335 on chromosome 16.

Thus, marker loci of the present disclosure that have been found to be associated with an rbs3b hidden haplotype and/or rbs3b-type resistance to BSR infection and can be used to identify a soybean plant or soybean germplasm with improved rbs3b-type resistance to BSR infection. The ability to use a single marker to identify and select a soybean plant or soybean germplasm having rbs3b-type resistance or improved rbs3b-type resistance to BSR infection and/or comprises an rbs3b hidden haplotype increases the efficiency of MAS methods utilized in soybean breeding programs.

The detection of the at least one allele of one or more marker locus associated with a particular haplotype of BSR resistance, i.e., an rbs3a haplotype, an rbs3b haplotype or an rbs3b hidden haplotype can be performed before, during, or simultaneous with the detection of the at least one allele of one or more marker locus associated with resistance to BSR infection derived from any rbs3 source. Any combination of the chromosomal intervals, alleles, marker loci or haplotypes described herein for the detection of the least one allele of one or more marker locus associated with a particular type of BSR resistance is suitable for use with any combination of the chromosomal intervals, alleles, marker loci or haplotypes described herein for the detection of the least one allele of one or more marker locus associated with resistance to BSR infection derived from any rbs3 source. For example, the detection of at least one allele of one or more marker locus associated with resistance to BSR infection tracked by an rbs3a haplotype, rbs3b haplotype or an rbs3b hidden haplotype and the detection at least one allele of one or more marker locus associated with resistance to BSR infection derived from any rbs3 source, may comprise one or more marker locus:

(i) selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof;

(ii) selected from the group consisting of Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 and a combination thereof;

(iii) selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702 Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof;

(iv) selected from the group consisting of Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof; or (v) a combination of (i) with any or all of (ii), (iii), or (iv).

In addition to the markers discussed herein, information regarding useful soybean markers can be found, for example, on the USDA's Soybase website (http://www.soybase.org/). One of skill in the art will recognize that the identification of favorable markers alleles may be germplasm-specific. The determination of which marker alleles correlate with resistance (or susceptibility) is determined for the particular germplasm under study. One of skill in the art will also recognize that methods for identifying the favorable alleles are routine and well known in the art, and furthermore, that the identification and use of such favorable alleles is well within the scope of the invention.

In certain embodiments, multiple marker loci that collectively make up a haplotype and/or a marker profile are investigated, for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci described herein. In some embodiments, a haplotype for rbs3a-type resistance may comprise one or more rbs3a haplotype-associated allele of a marker provided in Table 2. In other embodiments, a haplotype for rbs3b-type resistance may comprise one or more rbs3b haplotype-associated allele of a marker provided in Table 3 or rbs3 hidden haplotype-associated allele of a marker provided in Table 4.

In other embodiments, the method involves detecting a marker profile comprising two or more marker loci, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 marker loci, or more. In some embodiments the method uses MAS to stack two or more loci in a soybean plant or soybean germplasm. In some embodiments, the method uses a marker profile to produce a soybean plant or soybean germplasm having improved resistance to BSR infection. In other embodiments, the method uses a marker profile to produce a soybean plant or soybean germplasm having improved rbs3a-type or rbs3b-type resistance.

Furthermore, the method may use MAS to track BSR resistance regardless of the particular type of BSR resistance or the rbs3 source of BSR resistance to efficiently select soybean plants or soybean germplasms with improved resistance to BSR infection and to separate these soybean plants or soybean germplasm from plant material susceptible to BSR infection. In some embodiments, it may be desirable to identify the particular source or type of BSR resistance in soybean plants or soybean germplasms in which a marker allele associated with resistance to BSR infection derived from any rbs3 source has been detected.

Suitable Techniques for the Detection of Marker Alleles

In certain aspects described herein, the method of selected a soybean plant or soybean germplasm having improved resistance to BSR infection includes a detecting step. While not intending to be limited to any particular embodiment, provided herein are exemplary detection methods suitable for use with the present methods. For example, analysis of sequence databases of soybean varieties (e.g., databases generated by genotype-by-sequence methods) in combination with archived phenotype information is suitable for the identification of suitable markers contained within or linked to a QTL associated with resistance to BSR infection and/or markers associated with any rbs3 source and/or a particular haplotype of BSR resistance.

In another embodiment, the method of detecting comprises DNA sequencing of at least one of the marker loci provided herein. As used herein, "sequencing" refers to sequencing methods for determining the order of nucleotides in a molecule of DNA. Any DNA sequencing method known in the art can be used in the methods provided herein. Non-limiting embodiments of DNA sequencing methods useful in the methods provided herein include Next Generation Sequencing (NGS) technologies, for example, as described in Egan, A. N, et al. (2012) *American Journal of Botany* 99(2): 175-185; genotyping by sequencing (GBS) methods, for example, as described in Elshire, R. J., et al. (2011) *PLoS ONE* 6(5):e19379; Molecular Inversion Probe (MIP) genotyping, as described, for example, in Hardenbol, P., et al. (2003) *Nature Biotechnology* 21(6):673-678; or high throughput genotyping by whole-genome resequencing, as described, for example in Huang, X et al., (2009) *Genome Research* 19:1068-1076. Each of the above references is incorporated by reference in their entirety herein.

In other aspects, the detecting may comprise designing a primer or probe that is complementary or partially complementary to at least a portion of the genomic DNA encompassing the marker locus and capable of specifically hybridizing to the marker locus of interest under at least moderately stringent conditions. In such aspects, the primer or probe optionally comprises a detectable label. Genomic DNA may be extracted from plant material using any suitable technique in the art, e.g., the CTAB (cetyltriethylammonium bromide, Sigma H5882) method described by Stacey & Isaac (Methods in Molecular Biology. Vol. 28: Protocols for Nucleic Acid Analysis by Nonradioactive Probes, Ed: Isaac, Humana Press Inc, Totowa, N.J. 1994, Ch 2, pp. 9-15). Detecting may comprise isolating nucleic acids, amplifying the genomic DNA encompassing the marker locus or a portion of the genomic DNA encompassing the marker locus and detecting the resulting amplified marker amplicon. In some embodiments, the amplifying comprises admixing an amplification primer or amplification primer pair and, optionally at least one nucleic acid probe, with a nucleic acid isolated from the soybean plant or soybean germplasm, wherein the primer or primer pair and optional probe is complementary or partially complementary to at least a portion of the genomic DNA encompassing the marker locus and is capable of initiating DNA polymerization by a DNA polymerase using the soybean nucleic acid as a template; and, extending the primer or primer pair in a DNA polymerization reaction comprising a DNA polymerase and a template nucleic acid to generate at least one amplicon, such as an amplicon represented by any of SEQ ID NOs: 172-175. In particular embodiments, the detection comprises real time PCR analysis.

In a certain aspect, a method of selecting soybean plants for improved resistance to BSR infection is provided that comprises extracting genomic DNA from a genetically diverse population of soybean plants and admixing an isolated polynucleotide with each genomic DNA sample, wherein the polynucleotide is capable of hybridizing with a favorable allele of a marker locus as described in Tables 1-4. In another embodiment, the polynucleotide is capable of hybridizing with a favorable allele of a marker locus selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541, Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241, Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702 Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102, Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof. In a preferred embodiment, the polynucleotide is capable of hybridizing with a favorable allele of a marker locus selected from the group consisting Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof. In certain embodiments, the isolated polynucleotide is a primer or probe. In a particular embodiment, the method further comprises detecting the presence of the hybridized polynucleotide in one or more of the genomic samples as an indication of a soybean plant or soybean germplasm with improved resistance to brown stem rot infection. In other embodiments, a soybean plant or soybean germplasm for which the presence of the hybridized polynucleotide is detected is crossed to another soybean plant, such as a recurrent soybean parent, to produce a population of progeny soybean germplasm. In such embodiments, the progeny soybean germplasm can be genotyped for the presence of a marker allele favorable for resistance to BSR infection using the detection methods described herein.

In certain embodiments, a method of selecting soybean plants for improved resistance to BSR infection is provided that comprises extracting genomic DNA from a genetically diverse population of soybean plants and admixing an isolated polynucleotide with each genomic DNA sample, wherein the polynucleotide comprises a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99% sequence identity to the nucleic acid sequence selected from the group consisting of SEQ ID NOs: 158, 159, 162, 163, 166, 167, 170 and 171, provided that the nucleic acid sequence comprises a nucleic acid complementary to and that hybridizes with a favorable allele as described in Tables 1-4. In a preferred embodiment, the isolated polynucleotide is capable of hybridizing to marker locus Gm16:32544169 and comprises a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99% sequence identity to the nucleic acid sequence represented by SEQ ID NO: 158, provided that the nucleic acid sequence comprises an adenine that hybridizes to a thymidine at 32,544,169 bp of chromosome 16. In a most preferred embodiment, the isolated polynucleotide comprises a nucleic acid sequence represented by SEQ ID NO: 158.

In some embodiments, molecular markers are detected using a suitable amplification-based detection method. Typical amplification methods include various polymerase based replication methods, including the polymerase chain reaction (PCR), ligase mediated methods, such as the ligase chain reaction (LCR), and RNA polymerase based amplification (e.g., by transcription) methods. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage & Caruthers (1981) Tetrahedron Letts 22:1859-1862, e.g., using a commercially available automated synthesizer, e.g., as described in Needham-VanDevanter et al. (1984) Nucl Acids Res 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair, or probe. For example, primers can be designed using any suitable software program, such as LASERGENE® or Primer3.

The primers are not limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length, or alternatively, at least 300 nucleotides in length, or alternatively, at least 400 nucleotides in length, or alternatively, at least 500 nucleotides in length, or alternatively, at least 1000 nucleotides in length, or alternatively, at least 2000 nucleotides in length or more.

PCR, RT-PCR, and LCR are common amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis et al. (1987) U.S. Pat. No. 4,683,202; Amheim & Levinson (1990) C&EN 36-47; Kwoh et al. (1989) Proc Natl Acad Sci USA 86:1173; Guatelli et al. (1990) Proc Natl Acad Sci USA 87:1874; Lomell et al. (1989) J Clin Chem 35:1826; Landegren et al. (1988) Science 241:1077-1080; Van Brunt (1990) Biotechnology 8:291-294; Wu & Wallace (1989) Gene 4:560; Barringer et al. (1990) Gene 89:117; and Sooknanan & Malek (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype alleles, such as SNP alleles, are provided. Real-time amplification assays, including MB or TAQMAN® based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain embodiments, each allele-specific probe for a certain SNP locus is 13-18 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

In certain embodiments, the detection step in the methods disclosed herein comprises PCR detection using amplification primers for amplifying at least a portion of one or more genomic regions of the soybean genome having at least 80%, 81%, 82%, 83%, 84%, 85%, 86%, 87%, 88%, 89%, 90%, 91%, 92%, 93%, 94%, 95%, 96%, 97%, 98%, 99% sequence identity to the nucleic acid sequence selected from the group consisting of SEQ ID NOs: 1-155. In a preferred embodiment, the detection step in the methods disclosed herein comprises PCR detection using amplification primers for amplifying at least a portion of one or more genomic regions of the soybean genome having at least 80%, 81%, 82%, 83%, 84%, 85%, 86%, 87%, 88%, 89%, 90%, 91%, 92%, 93%, 94%, 95%, 96%, 97%, 98%, 99% sequence identity to the nucleic acid sequence selected from the group consisting of SEQ ID NOs: 3, 49, 68, and 111 using nucleic acid primers comprising a nucleic acid sequence selected from the group consisting of SEQ ID NOs: 156, 157, 160, 161, 164, 165, 168, and 169. In some aspects, the amplification step further includes the use of allele-specific probes capable of hybridizing to a specific allele of the marker locus. For example, one or more probes comprising a nucleic acid sequence selected from the group consisting of SEQ ID NOs: 158, 159, 162, 163, 166, 167, 170 and 171 can be used in the present methods for detecting an allele of the marker loci associated with resistance to BSR infection conferred by an rbs3a-type rbs3b-type resistance trait. In other aspects, primers or probes are provided for detecting a polymorphism of any of the marker loci associated with resistance described herein. In certain embodiments, the primers or probes comprise one or more nucleic acid sequences selected from the group consisting of SEQ ID NOs: 156-171. Exemplary primers and probes are provided in Table 5.

TABLE 5

Non-limiting list of suitable primers and probes for the detection of various marker loci of the present disclosure.

| Marker Name | Linkage Group/ Chrom. No. | Relative Map Position (cM) | Approximate Physical Position of SNP (bp) | SEQ ID NO. | Primer or Probe |
|---|---|---|---|---|---|
| Gm16:32544169 | J/16 | 83.99 | 32,544,169 | 156 | Primer |
| | | | | 157 | Primer |
| | | | | 158 | Allelic Probe |
| | | | | 159 | Allelic Probe |
| Gm16:32234335 | J/16 | 82.59 | 32,234,335 | 160 | Primer |
| | | | | 161 | Primer |
| | | | | 162 | Allelic Probe |
| | | | | 163 | Allelic Probe |
| Gm16:32296634 | J/16 | 82.97 | 32,296,634 | 164 | Primer |
| | | | | 165 | Primer |
| | | | | 166 | Allelic Probe |
| | | | | 167 | Allelic Probe |
| Gm16:32271574 | J/16 | 82.82 | 32,271,574 | 168 | Primer |
| | | | | 169 | Primer |
| | | | | 170 | Allelic Probe |
| | | | | 171 | Allelic Probe |

In addition to the primer and probe sequences described herein, one of skill will immediately recognize that other primer and probe sequences could also be used. For instance, primers to either side of the given primers can be used in place of the given primers, so long as the primers can amplify a region that includes the allele to be detected, as can primers and probes directed to other marker loci. Further, it will be appreciated that the precise probe to be used for detection can vary, e.g., any probe that can identify the region of a marker amplicon to be detected can be substituted for those embodiments provided herein. Further, the configuration of the amplification primers and detection probes can, of course, vary. Thus, the compositions and methods are not limited to the primers and probes specifically recited herein. In other embodiments, primers and probes can be designed to detect a SNP allele in a genomic DNA sequence provided in Tables 1-4.

In certain embodiments, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabeled PCR primers that are used to generate a radiolabeled amplicon. Labeling strategies for labeling nucleic acids and their corresponding detection strategies can be found, e.g., in Haugland (1996) *Handbook of Fluorescent Probes and Research Chemicals Sixth Edition* by Molecular Probes, Inc. (Eugene, Oreg.); or Haugland (2001) *Handbook of Fluorescent Probes and Research Chemicals Eighth Edition* by Molecular Probes, Inc. (Eugene, Oreg.).

Detectable labels may also include reporter-quencher pairs, such as are employed in Molecular Beacon and TAQMAN® probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent. Generally, whether the quencher is fluorescent or simply releases the transferred energy from the reporter by nonradiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland (2001) *Handbook of Fluorescent Probes and Research Chemicals Eighth Edition* by Molecular Probes, Inc. (Eugene, Oreg.), the content of which is incorporated herein by reference.

In certain embodiments, reporter-quencher pairs are selected from xanthene dyes including fluorescein and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters is the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other embodiments, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein. e.g., using molecular beacons or TAQMAN® probes. A molecular beacon (MB) is an oligonucleotide that, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone et al. (1995) Nucl Acids Res 26:2150-2155; Tyagi & Kramer (1996) Nat Biotechnol 14:303-308; Blok & Kramer (1997) Mol Cell Probes 11:187-194; Hsuih et al. (1997) J Clin Microbiol 34:501-507; Kostrikis et al. (1998) Science 279: 1228-1229; Sokol et al. (1998) Proc Natl Acad Sci USA 95:11538-11543; Tyagi et al. (1998) Nat Biotechnol 16:49-53; Bonnet et al. (1999) Proc Natl Acad Sci USA 96:6171-6176; Fang et al. (1999) J Am Chem Soc 121:2921-2922; Marras et al. (1999) Genet Anal Biomol Eng 14:151-156; and, Vet et al. (1999) Proc Natl Acad Sci USA 96:6394-6399. Additional details regarding MB construction and use are also found in the patent literature, e.g., U.S. Pat. Nos. 5,925,517; 6,150,097; and 6,037,130.

Another real-time detection method is the 5'-exonuclease detection method, also called the TAQMAN® assay, as set forth in U.S. Pat. Nos. 5,804,375; 5,538,848; 5,487,972; and 5,210,015, each of which is hereby incorporated by reference in its entirety. In the TAQMAN® assay, a modified probe, typically 10-30 nucleotides in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are typically attached to the probe within a few nucleotides of one another, usually within 30 nucleotides of one another, or within 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

One embodiment of a suitable real-time detection technique that does not use a separate probe that binds intermediate to the two primers is the KASPar detection system/method, which is well known in the art. In KASPar, two allele specific primers are designed such that the 3' nucleotide of each primer hybridizes to the polymorphic base. For example, if the SNP is an A/C polymorphism, one of the primers would have an "A" in the 3' position, while the other primer would have a "C" in the 3' position. Each of these two allele specific primers also has a unique tail sequence on the 5' end of the primer. A common reverse primer is employed that amplifies in conjunction with either of the two allele specific primers. Two 5' fluor-labeled reporter oligos are also included in the reaction mix, one designed to interact with each of the unique tail sequences of the allele-specific primers. Lastly, one quencher oligo is included for each of the two reporter oligos, the quencher oligo being complementary to the reporter oligo and being able to quench the fluor signal when bound to the reporter oligo. During PCR, the allele-specific primers and reverse primers bind to complementary DNA, allowing amplification of the amplicon to take place. During a subsequent cycle, a complementary nucleic acid strand containing a sequence complementary to the unique tail sequence of the allele-specific primer is created. In a further cycle, the reporter oligo interacts with this complementary tail sequence, acting as a labeled primer. Thus, the product created from this cycle of PCR is a fluorescently-labeled nucleic acid strand. Because the label incorporated into this amplification product is specific to the allele specific primer that resulted in the amplification, detecting the specific fluor presenting a signal can be used to determine the SNP allele that was present in the sample.

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook: *Current Protocols in Molecular Biology*, F. M. Ausubel et al., eds., Current Protocols, a joint venture between Greene Publishing Associates. Inc. and John Wiley & Sons, Inc., (supplemented through 2002) ("Ausubel"); and, *PCR Protocols A Guide to Methods and Applications* (Innis et al., eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH) or nucleic acid sequencing techniques. ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Isolated polynucleotide or fragments thereof, e.g., a primers and/or probe, are capable of specifically hybridizing to other nucleic acid molecules under appropriate conditions. In some embodiments, the nucleic acid molecules comprise any of the marker loci of the present invention. It will be appreciated that suitable primers and probes to be used can be designed using any suitable method. It is not intended to be limited to any particular primer, primer pair or probe. For example, primers or probes can be designed using any suitable software program, such as LASERGENE® or Primer3. In one embodiment, the nucleic acid molecules comprise any of SEQ ID NOs: 156-171, complements thereof and fragments thereof. In another aspect, the nucleic acid molecules of the present invention include nucleic acid molecules that hybridize, for example, under high or low stringency, substantially homologous sequences, or that have both to these molecules. Conventional stringency conditions are described by Sambrook, and by Haymes et al. In: Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed. Appropriate stringency conditions that promote DNA hybridization are known to those skilled in the art or can be found in Current Protocols in Molecular Biology, John Wiley & Sons, N.Y., 1989, 6.3.1-6.3.6.

Typically, stringent conditions will be those in which the salt concentration is less than about 1.5 M Na ion, typically about 0.01 to about 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the thermal melting point (Tm) can be approximated from the equation of Meinkoth et al., *Anal. Biochem.* 138:267-284 (1984): Tm=81.5° C.+16.6 (log M) 4−0.41 (% GC)−0.61 (% form)−500/L; where M is the molarity of monovalent cations, % GC is the percentage of guano sine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm hybridization and/or wash conditions can be adjusted to hybridize to sequences of the desired identity. For example, if sequences with ≥90% identity are sought, the Tm can be decreased 10° C. Generally, stringent conditions are selected to be about 5° C. lower than Tm for the specific sequence and its complement at a defined ionic strength and pH. However, severely stringent conditions can utilize a hybridization and/or wash at 1, 2, 3, or 4° C. lower than the Tm moderately stringent conditions can utilize a hybridization and/or wash at 6, 7, 8, 9, or 10° C. lower than the Tm; low stringency conditions can utilize a hybridization and/or wash at 11, 12, 13, 14, 15, or 20° C. lower than the Tm. Using the equation, hybridization and wash compositions, and desired Tm those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Inter-science, New York (1995). Hybridization and/or wash conditions can be applied for at least 10, 30, 60, 90, 120, or 240 minutes.

In some embodiments, a nucleic acid, e.g., primers and/or probes, of the present invention will specifically hybridize to one or more of the nucleic acid molecules set forth in SEQ ID NOs: 1-155 or 172-175 or complements thereof, or fragments of either, under moderately stringent conditions. In an aspect, a nucleic acid of the present invention will specifically hybridize to one or more SEQ ID NOs: 1-155 or 172-175 or complements, or fragments of either, under high stringency conditions.

In some embodiments, a marker locus within or linked to a QTL associated with a preferred reproductive growth phenotype is localized within a genomic region comprising any one of SEQ ID NOs: 1-155 or 172-175. In other embodiments, a marker locus is localized within a genomic region having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of SEQ ID NOs: 1-155 or 172-175 or complements or fragments thereof. Unless otherwise stated, percent sequence identity is determined using the GAP program default parameters for nucleic acid alignment (Accelrys, San Diego, Calif., USA).

In some embodiments, a kit for detecting markers or haplotypes, and/or for correlating the markers or haplotypes with a desired phenotype (e.g. a BSR resistance phenotype), are provided. Thus, a typical kit can include a set of marker probes and/or primers configured to detect at least one favorable allele or polymorphism of one or more marker locus associated with resistance to BSR infection. These probes or primers can be configured, for example, to detect the marker alleles or polymorphisms noted in the tables and embodiments herein, e.g., using any available allele detection format, such as solid or liquid phase array based detection, microfluidic-based sample detection, etc. The kits can further include packaging materials for packaging the probes, primers, or instructions; controls, such as control amplification reactions that include probes, primers, and/or template nucleic acids for amplifications; molecular size markers; or the like.

System or kit instructions that describe how to use the system or kit and/or that correlate the presence or absence of the allele with the predicted preferred or non-preferred phenotype are also provided. For example, the instructions can include at least one look-up table that includes a correlation between the presence or absence of the favorable allele(s) and resistance to BSR infection in general or the particular type of resistance to BSR infection. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector.

Isolated nucleic acids comprising a nucleic acid sequence coding for BSR resistance, or capable of detecting such a phenotypic trait, or sequences complementary thereto, are also included. In certain embodiments, the isolated nucleic acids are capable of hybridizing under stringent conditions to nucleic acids of a soybean cultivar, to detect one or more marker loci associated with resistance to BSR infection derived from any rbs3 source and/or associated with a particular rbs3a, rbs3b or rbs3b hidden haplotype, including one or more of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541, Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241, Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702 Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102, Gm16:32234335, Gm16:32233691, Gm16:32235048, Gm16:

32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 or any a combination thereof.

In a certain aspect, a kit for selecting at least one soybean plant by marker assisted selection of a QTL associated with resistance to BSR infection is provided, the kit comprising primers or probes for detecting a polymorphism in the soybean genome, wherein the physical location of the polymorphism is on chromosome 16 and selected from the group consisting of 32,543,279 bp, 32,544,128 bp, 32,544,169 bp, 32,545,642 bp, 32,544,181 bp, 32,545,680 bp, 32,291,307 bp, 32,543,387 bp, 32,284,137 bp, 32,544,094 bp, 32,543,360 bp, 32,546,349 bp, 32,324,276 bp, 32,544,455 bp, 32,346,680 bp, 32,543,724 bp, 32,546,343 bp, 32,543,241 bp, 32,542,545 bp, 32,286,588 bp, 32,546,309 bp, 32,282,532 bp, 32,540,234 bp, 32,346,259 bp, 32,546,697 bp, 32,286,461 bp, 32,542,834 bp, 32,346,754 bp, 32,286,518 bp, 32,542,809 bp, 32,545,807 bp, 32,239,934 bp, 32,544,481 bp, 32,346,987 bp, 32,347,808 bp, 32,540,201 bp, 32,546,282 bp, 32,286,403 bp, 32,545,360 bp, 32,285,402 bp, 32,544,988 bp, 32,286,428 bp, 32,283,215 bp, 32,454,541 bp and any combination thereof. In addition, instructions for using the primers or probes to detect the marker loci and correlate the marker loci with improved resistance to BSR infection. In some embodiments, the primers or probes will comprise a detectable label, including, but not limited to, a FAM (6-carboxyfluorescein) or VIC (4,7,2'-trichloro-7'-phenyl-6-carboxyfluorescein) fluorophore at the 5' end.

In some embodiments the primers or probes are selected from Table 5. For example, suitable primers or probes may comprise a nucleic acid sequence represented by any one of SEQ ID NOs: 156-171 or a portion of any one of SEQ ID NOs: 1-155 or 172-175. Vectors comprising one or more of the nucleic acids represented by SEQ ID NOs: 1-172, expression products of such vectors expressed in a host compatible therewith, antibodies to the expression product (both polyclonal and monoclonal), and antisense nucleic acids are also included. In some embodiments, one or more of these nucleic acids is provided in a kit.

These systems and methods represent a wide variety of available detection methods which can be utilized to detect markers associated with improved resistance to BSR infection, but any suitable method could also be used.

MAS Selection and Introgression

The use of marker assisted selection (MAS) to select a soybean plant or germplasm based upon detection of a particular marker or haplotype of interest is provided. For instance, in certain embodiments, a soybean plant or germplasm possessing a certain predetermined favorable marker allele or haplotype will be selected via MAS. Using MAS, soybean plants or germplasm can be selected for markers or marker alleles that positively correlate with resistance to BSR infection, without actually raising soybean and measuring for resistance (or, contrawise, soybean plants can be selected against if they possess markers that negatively correlate with BSR resistance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In still further aspects, the information disclosed herein regarding marker loci, marker alleles, haplotypes, and/or marker profiles can be used to aid in the creation and/or selection of soybean plants, soybean germplasms, soybean progeny, soybean breeding plants, lines, and populations for improved resistance to BSR infection, including rbs3a-type resistance or rbs3b-type resistance. In a preferred aspect, the utilization of markers associated with resistance to BSR infection derived from any rbs3 source enable the selection of soybean plants, soybean germplasms, and soybean progeny with improved resistance to BSR. In other words, genotyping a soybean plant at even a single marker locus, such as any marker locus described in Table 1, is sufficient to detect a soybean plant or soybean germplasm with improved BSR resistance in order to separate resistant soybean plants and soybean germplasms from soybean plants and soybean germplasms that are susceptible to BSR infection. In one embodiment, methods and kits used for selection of soybean plants and soybean germplasms comprise detection of a marker allele that positively correlates, or is associated, with resistance to BSR infection, wherein the marker locus is selected from the group consisting of Gm16:32543279, Gm16:32544128, Gm16:32544169, Gm16:32545642, Gm16:32544181, Gm16:32545680, Gm16:32291307, Gm16:32543387, Gm16:32284137, Gm16:32544094, Gm16:32543360, Gm16:32546349, Gm16:32324276, Gm16:32544455, Gm16:32346680, Gm16:32543724, Gm16:32546343, Gm16:32543241, Gm16:32542545, Gm16:32286588, Gm16:32546309, Gm16:32282532, Gm16:32540234, Gm16:32346259, Gm16:32546697, Gm16:32286461, Gm16:32542834, Gm16:32346754, Gm16:32286518, Gm16:32542809, Gm16:32545807, Gm16:32239934, Gm16:32544481, Gm16:32346987, Gm16:32347808, Gm16:32540201, Gm16:32546282, Gm16:32286403, Gm16:32545360, Gm16:32285402, Gm16:32544988, Gm16:32286428, Gm16:32283215, Gm16:32454541 and a combination thereof. Thus, the present methods improve the efficiency and accuracy of selection of soybean plants and soybean germplasms, even from heterogeneous populations and/or from among different soybean varieties, via MAS as compared to previous genotyping techniques that required the use of multiple marker loci to identify and/or select soybean plants and soybean germplasms with improved resistance to BSR infection.

Also provided herein are marker loci that are highly associated with a particular haplotype for BSR resistance, such as the marker loci described in Tables 2-4, that can be used in combination with marker loci that are associated with resistance to BSR infection derived from any rbs3 source in order to identify the particular source of BSR resistance.

In one aspect, a method for selecting a soybean plant with improved resistance to BSR infection from a population of genetically diverse and/or heterogeneous soybean plants is provided. In one embodiment, the method comprises extracting genomic DNA samples from each of the soybean plants in the genetically diverse and/or heterogeneous population and admixing a first isolated polynucleotide with each of the genomic DNA samples, wherein the first polynucleotide is capable of hybridizing with a favorable allele of a marker locus selected from the group consisting of Gm16: 32543279, Gm16:32544128, Gm16:32544169, Gm16: 32545642, Gm16:32544181, Gm16:32545680, Gm16: 32291307, Gm16:32543387, Gm16:32284137, Gm16: 32544094, Gm16:32543360, Gm16:32546349, Gm16: 32324276, Gm16:32544455, Gm16:32346680, Gm16: 32543724, Gm16:32546343, Gm16:32543241, Gm16: 32542545, Gm16:32286588, Gm16:32546309, Gm16: 32282532, Gm16:32540234, Gm16:32346259, Gm16: 32546697, Gm16:32286461, Gm16:32542834, Gm16: 32346754, Gm16:32286518, Gm16:32542809, Gm16: 32545807, Gm16:32239934, Gm16:32544481, Gm16: 32346987, Gm16:32347808, Gm16:32540201, Gm16: 32546282, Gm16:32286403, Gm16:32545360, Gm16: 32285402, Gm16:32544988, Gm16:32286428, Gm16: 32283215, Gm16:32454541 and a combination thereof. In such an embodiment, the detection of the hybridized first polynucleotide in one or more of the genomic DNA samples indicates a soybean plant with improved resistance to BSR infection, which is then selected for use in breeding programs. In a preferred embodiment, the first polynucleotide is a probe; more preferably it is a allele-specific probe. In addition, the methods of the present disclosure can be used to select progeny plants having improved resistance to BSR infection that are produced from a cross between a soybean plant with improved BSR resistance and another soybean plant, such as an exotic soybean plant variety, elite soybean plant variety, etc.

Introgression of BSR resistance into non-resistant or less-resistant soybean germplasm is provided. Any method for introgressing one or more marker loci into soybean plants known to one of skill in the art can be used. Typically, a first soybean germplasm that contains a BSR resistance trait derived from a particular marker locus, haplotype, QTL or marker profile and a second soybean germplasm that lacks such resistance derived from the marker locus, haplotype, QTL or marker profile are provided. The first soybean germplasm may be crossed with the second soybean germplasm to provide progeny soybean germplasm. These progeny germplasm are screened to determine the presence of BSR resistance derived from the marker locus, haplotype, QTL, or marker profile, and progeny that test positive for the presence of resistance derived from the marker locus, haplotype, QTL or marker profile are selected as being soybean germplasm into which the marker locus, haplotype, QTL or marker profile has been introgressed. Methods for performing such screening are well known in the art and any suitable method can be used.

One application of MAS is to use the resistance markers, haplotypes or marker profiles to increase the efficiency of an introgression or backcrossing effort aimed at introducing a resistance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible. Thus, the markers and methods can be utilized to guide MAS or breeding of soybean varieties with the desired complement (set) of allelic forms of chromosome segments associated with superior agronomic performance (resistance, along with any other available markers for yield, disease resistance, etc.). Any of the disclosed marker loci, marker alleles, haplotypes, QTLs or marker profiles can be introduced into a soybean line via introgression, by traditional breeding (or introduced via transformation, or both) to yield a soybean plant with superior agronomic performance. The number of alleles associated with resistance that can be introduced or be present in a soybean plant ranges from 1 to the number of alleles disclosed herein, each integer of which is incorporated herein as if explicitly recited.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with BSR resistance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant in that it comprises at least one of the marker loci or marker profiles, such that the progeny are capable of inheriting the marker locus or marker profile.

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, primers, probes, and marker profiles can be used for MAS in crosses involving elite x exotic soybean lines by subjecting the segregating progeny to MAS to maintain major yield alleles, along with the resistance marker alleles herein.

In one embodiment, a soybean plant or soybean germplasm having improved resistance to BSR infection is identified and/or selected using the methods and marker loci described herein. In such an embodiment, the selected soybean plant or soybean germplasm is crossed to another soybean plant, such as an elite soybean plant or a recurrent soybean parent, to produce a population of progeny soybean germplasm in which a QTL associated with BSR resistance is introgressed into a subpopulation of the progeny soybean germplasm. The resulting subpopulation of progeny soybean germplasm may display: (i) rbs3a-type resistance or improved rbs3a-type resistance to BSR infection; (ii) rbs3b-type resistance or improved rbs3b-type resistance; (iii) or a combination of both (e.g., an F1 hybrid progeny line).

As an alternative to standard breeding methods of introducing traits of interest into soybean (e.g., introgression), transgenic approaches can also be used to create transgenic plants with the desired traits. In these methods, exogenous nucleic acids that encode a desired marker loci, marker allele, marker profile, QTL or haplotype are introduced into target plants or germplasm. For example, a nucleic acid that codes for a BSR resistance trait is cloned, e.g., via positional cloning, and introduced into a target plant or germplasm.

Experienced plant breeders can recognize resistant soybean plants in the field, and can select the resistant individuals or populations for breeding purposes or for propagation. In this context, the plant breeder recognizes "resistant" or "tolerant" and "nonresistant" or "susceptible" soybean plants. However, plant resistance is a phenotypic spectrum of extremes in resistance and susceptibility, as well as a continuum of intermediate resistance phenotypes. Evaluation of these intermediate phenotypes using reproducible assays are of value to scientists who seek to identify genetic loci that impart resistance, to conduct marker assisted selection for resistant populations, and to use introgression techniques to breed a resistance trait into an elite soybean line, for example.

By "improved resistance" is intended that the soybean plants show a decrease in the disease symptoms that are the outcome of plant exposure to BSR. That is, the damage caused by BSR is prevented, or alternatively, the disease symptoms caused by BSR is minimized or lessened. Thus, improved resistance or improved tolerance to BSR can result in reduction of the disease symptoms by at least about 2% to at least about 6%, at least about 5% to about 50%, at least about 10% to about 60%, at least about 30% to about 70%, at least about 40% to about 80%, or at least about 50% to about 90% or greater. Hence, the methods provided herein can be utilized to protect plants from BSR.

As discussed herein, BSR infection of soybean is caused by the fungal pathogen *Phialophora gregata*. Screening and selection of BSR resistant or tolerant soybean plants may be performed, for example, by exposing plants to *Phialophora gregata* and selecting those plants showing resistance to BSR. Various assays can be used to measure resistance or improved resistance to BSR infection. For example, BSR resistance can be determined by visual observations after plant exposure to *Phialophora gregata*. Scores range from 1 to 9 and indicate visual observations of resistance as compared to other genotypes in the test. A score of 1 indicates *Phialophora gregata* is able to infect the plant and cause yield loss.

Non-limiting embodiments of BSR phenotypic screening are described in detail below. Phenotypic resistance or tolerance to BSR can be evaluated in the field. The fields are selected based on a strong history of BSR infection. Generally. BSR severity increases as soil pH decreases. BSR severity is generally greatest at pH 6.0 and declines as the pH increases. It has been observed that cool temperatures during the pod filling stage can also be a major factor in BSR development. Yield trial sites are valuable sources of good BSR ratings as well. Susceptible and resistant/tolerant varieties are grown as checks.

BSR leaf symptoms will appear during late reproductive phases and typically peak during R6 crop stage. In the Midwest region of the United States, R6 typically occurs in mid August through mid September, depending on the planting date and maturity of the soybean cultivar. Leaf symptoms can be scored when differences are apparent, up through leaf senescence after R7. In some cases, leaf symptoms may be absent but stem symptoms may be apparent. Stem symptoms typically reach peak intensity at R7 through R8. BSR infection can be scored using stem and/or leaf tissues: (i) Split stem symptoms (BRSTM) and/or (ii) leaf scorch symptoms (BSRLF). The scoring system for the BSRLF trait is an estimate of affected leaf area based on a visual assessment of incidence-by-severity for the plot. A 1-9 scale is used based on total leaf area of plot affected:

9=no symptoms,
8=slight symptoms (a few chlorotic spots can be found),
7=about 15% affected leaf area,
6=30% affected leaf area,
5=about 40% total leaf area affected,
4=50% affected leaf area,
3=60% affected leaf area,
2=70% affected leaf area.
1=>80° % affected leaf area.

Stems are periodically split to confirm if stem browning is present in plants showing leaf symptoms. As is known to those skilled in the art, there are two BSR pathogen types. Type A produces stem and leaf symptoms while Type B produces stem symptoms only. Split stems are scored based on the percent of brown nodes as follows:

9=clean,
8=slight browning (1 or 2 nodes),
1=nearly the entire plant with brown nodes.

The pathology of the affected plants is evaluated to ensure that the symptoms are not being confused with sudden death syndrome.

The plots are scored approximately 2-3 times at 5-7 day intervals until the plot reached R7. R7 is a stage at the beginning of maturity, with seed in one or more pods that are physiologically mature.

Further, the marker alleles, marker loci, haplotypes, QTLs, and/or marker profiles can be used in introgression into elite soybean germplasm, exotic soybean germplasm, or any other soybean germplasm. In some embodiments the marker alleles, marker loci, haplotypes, QTLs and/or marker profiles can be used to aid in the creation and/or selection of breeding plants, lines, and with improved resistance to BSR infection. Also provided is a method for introgressing into a soybean germplasm a soybean QTL, marker locus, marker allele, haplotype, and/or marker profile associated with resistance to BSR infection conferred by rbs3a-type resistance or rbs3b-type resistance. Such method may optionally include introgressing into a soybean germplasm a soybean QTL, marker locus, marker allele, haplotype, and/or marker profile associated with a particular type or source of resistance to BSR infection.

In some embodiments the methods include identifying trait loci in a mixed defined plant population comprising multiple plant families (see, e.g., U.S. Pat. No. 6,399,855, herein incorporated by reference in its entirety). The method comprises quantifying a phenotypic trait across lines sampled from the population, identifying at least one genetic marker associated with the phenotypic trait by screening a set of markers and identifying the quantitative trait loci based on the association of the phenotypic trait and the genetic marker(s). In some embodiments the plant population consists of diploid plants, either hybrid or inbred. The phenotypic traits associated with the locus are quantitative such that a numerical value can be ascribed to the trait, and the association of the genetic loci and the phenotypic trait is determined through specified statistical models. In some embodiments the statistical models are linear models with fixed effects and random effects. In a other embodiments the statistical model is a mixed effects model.

Soybean plants, germplasms seeds, tissue cultures, variants and mutants having a improved resistance to BSR infection produced by the foregoing methods are also provided. Soybean plants, seeds, tissue cultures, variants and mutants comprising one or more of the marker loci, one or more of the favorable alleles, and/or one or more of the haplotypes and having improved resistance to BSR infection are provided. Also provided are isolated nucleic acids, kits, and systems useful for the identification, prediction, and/or selection methods disclosed herein.

In some embodiments, the soybean plant, germplasm, plant part, or seed having improved resistance to BSR infection further comprises one or more other traits of interest including but not limited to improved resistance to one or more ALS-inhibiting herbicides, a hydroxyphenylpyruvatedioxygenase inhibitor, a phosphanoglycine (including but not limited to a glyphosate), a sulfonamide, an imidazolinone, a bialaphos, a phosphinothricin, a metribuzin, a mesotrione, an isoxaflutole, an azafenidin, a butafenacil, a sulfosate, a glufosinate, a dicamba, a 2,4-D, and a protox inhibitor. In some embodiments, resistance to the herbicidal formulation is conferred by a transgene. In some embodiments, the plant or germplasm further comprises a trait selected from the group consisting of extended reproductive growth stage, early flowering, drought tolerance, stress tolerance, disease resistance, herbicide resistance, enhanced yield, modified oil, modified protein, tolerance to chlorotic conditions, and insect resistance, or any combination thereof. In some embodiments, the trait is selected from the group consisting of charcoal rot drought complex resistance, *Fusarium* resistance, *Phytophthora* resistance, stem canker resistance, sudden death syndrome resistance, *Sclerotinia* resistance, *Cercospora* resistance, anthracnose resistance, target spot resistance, frogeye leaf spot resistance, soybean cyst nematode resistance, root knot nematode resistance, rust resistance, high oleic content, low linolenic content, aphid resistance, stink bug resistance, and iron chlorosis deficiency tolerance, or any combination thereof. In some embodiments, one or more of the traits is conferred by one or more transgenes, by one or more native loci, or any combination thereof.

Glyphosate resistance can be conferred from genes including but not limited to EPSPS, GAT, GOX, and the like, such as described in U.S. Pat. Nos. 6,248,876; 5,627,061; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE36,449; RE37,287 E; U.S. Pat. Nos. 5,491,288; 5,776, 760; 5,463,175; 8,044,261; 7·527,955; 7,666,643; 7,998, 703; 7,951,995; 7,968,770; 8,088,972, 7,863,503; and US20030083480; WO 97/04103; WO 00/66746; WO 01/66704; and WO 00/66747, which are each incorporated herein by reference in their entireties for all purposes. Additionally, glyphosate tolerant plants can be generated through the selection of naturally occurring mutations that impart tolerance to glyphosate.

HPPD resistance can be conferred by genes including exemplary sequences disclosed in U.S. Pat. Nos. 6,245,968; 6,268,549; and 6,069,115, and WO 99/23886, which are each incorporated herein by reference in their entireties for all purposes. Mutant hydroxyphenylpyruvatedioxygenases having this activity are also known. For further examples see US20110185444 and US20110185445.

Resistance to auxins, such as 2,4-D or dicamba, can be provided by polynucleotides as described, for example, in WO2005/107437, US20070220629, and U.S. Pat. No. 7,838,733 and in Herman et al. (2005) J. Biol. Chem. 280:24759-24767, each which is herein incorporated by reference.

Resistance to PPO-inhibiting herbicides can be provided as described in U.S. Pat. Nos. 6,288,306; 6,282,837; and 5,767,373; and WO 01/12825, each of which is herein incorporated by reference. Plants containing such polynucleotides can exhibit improved tolerance to any of a variety of herbicides which target the protox enzyme. Resistance can also be conferred as described in US20100186131; US20110185444; US20100024080, each of which is herein incorporated by reference.

The development of plants containing an exogenous phosphinothricin acetyltransferase which confers resistance to glufosinate, bialaphos, or phosphinothricin is described, for example, in U.S. Pat. Nos. 5,969,213; 5,489,520; 5,550,318; 5,874,265; 5,919,675; 5,561,236; 5,648,477; 5,646,024; 6,177,616; and 5,879,903, which are each incorporated herein by reference in their entireties for all purposes. Mutant phosphinothricin acetyltransferase having this activity are also known in the art.

Examples of markers and loci conferring improved iron chlorosis deficiency tolerance are disclosed in US20110258743, U.S. Pat. Nos. 7,582,806, and 7,977,533, each of which is herein incorporated by reference. Various disease resistance loci and markers are disclosed, for example, in WO1999031964, U.S. Pat. Nos. 5,948,953, 5,689,035, US20090170112, US20090172829, US20090172830, US20110271409, US20110145953, U.S. Pat. Nos. 7,642,403, 7,919,675, US20110131677, U.S. Pat. Nos. 7,767,882, 7,910,799, US20080263720, U.S. Pat. No. 7,507,874, US20040034890, US20110055960, US20110185448, US20110191893, US20120017339, U.S. Pat. Nos. 7,250,552, 7,595,432, 7,790,949, 7,956,239. U.S. Pat. No. 7,968,763, each of which is herein incorporated by reference.

Markers and loci conferring improved yield are provided, for example, in U.S. Pat. No. 7,973,212 and WO2000018963, each of which is herein incorporated by reference. Markers and loci conferring improved resistance to insects are disclosed in, for example, US20090049565, U.S. Pat. No. 7,781,648, US20100263085, U.S. Pat. Nos. 7,928,286, 7,994,389, and WO2011116131, each of which is herein incorporated by reference. Markers and loci for modified soybean oil content or composition are disclosed in, for example, US20120028255 and US20110277173, each of which is herein incorporated by reference.

Methods and compositions to modified soybean oil content are described in, for example, WO2008147935, U.S. Pat. Nos. 8,119,860; 8,119,784; 8,101,189; 8,058,517; 8,049,062; 8,124,845, 7,790,959, 7,531,718, 7,504,563, and 6,949,698, each of which is herein incorporated by reference. Markers and loci conferring tolerance to nematodes are disclosed in, for example, US20090064354, US20090100537, US20110083234, US20060225150, US20110083224, U.S. Pat. Nos. 5,491,081, 6,162,967, 6,538,175, 7,872,171, 6,096,944, and 6,300,541, each of which is herein incorporated by reference. Resistance to nematodes may be conferred using a transgenic approach as described, for example, in U.S. Pat. Nos. 6,284,948 and 6,228,992, each of which is herein incorporated by reference. Plant phenotypes can be modified using isopentyl transferase polynucleotides as described, for example, in U.S. Pat. Nos. 7,553,951 and 7,893,236, each of which is herein incorporated by reference.

Soybean variety V2 of Table 8 is also known as soybean variety XBO4E07. Applicant has made a deposit of seeds of Soybean Variety X1304E07 (V2 of Table 8) with the American Type Culture Collection (ATCC), 10801 University Boulevard, Manassas, Va. 20110 USA, as ATCC Deposit No. PTA-9326. The seeds deposited with the ATCC on Jul. 1, 2008 were taken from the seed stock maintained by Pioneer Hi-Bred International, Inc., 7250 NW 62$^{nd}$ Avenue, Johnston, Iowa 50131 since prior to the filing date of this application. Access to this seed stock will be available during the pendency of the application to the Commissioner of Patents and Trademarks and persons determined by the Commissioner to be entitled thereto upon request. Upon issuance of any claims in the application, the Applicant will make the deposit available to the public pursuant to 37 C.F.R. § 1.808. This deposit of Soybean Variety XBO4E07 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.).

The present disclosure is illustrated by the following examples. The foregoing and following description and the various examples are not intended to be limiting but rather are illustrative of the described embodiments. Hence, it will be understood that the present disclosure is not limited to the specific details of these examples.

EXAMPLES

Example 1. Case Control Association Analysis for Marker Loci Associated with Resistance to BSR Infection Derived from any Rbs3 Source Using a case-control association analysis, a locus conditioning resistance to BSR infection was fine-mapped between 32,239,934 to 32,546,697 bp on chromosome 16 (LG-J) of soybean. SNPs were identified in this region that are highly associated with the phenotypic variation observed across a panel of elite inbred cultivars. These markers, and markers within the fine-mapped region, are ideal for MAS of BSR resistance.

Phenotype and haplotype data was collected during field studies. Phenotypic scores correlated with the corresponding with susceptibility or an applicable resistance haplotype, including rbs3a haplotype/rbs3a-type resistance, rbs3b haplotype/rbs3b-type resistance, and rbs3b hidden haplotype/rbs3b-type resistance. All three sources of BSR resistance were included in the resistance category.

DNA was prepped using standard Illumina TruSeq Chemistry and lines were sequenced to ~0.5-40× genome coverage on an Illumina HiSeq2000. SNPs were called using the proprietary Biotique pipeline. The publically available software Haploview was used to conduct a case-control association analysis on a set of 8,917 SNPs identified in the region on chromosome 16 from 31,911,121 to 32,673,440 bp. The case group comprised 336 proprietary soybean lines susceptible to BSR infection and the control group comprised 187 proprietary lines resistant to BSR infection (see Table 6). Following haploview filtering, 4,525 SNPs remained in the analysis.

Haploview Settings:
  Do Association Test
  Case/Control Data
  Ignore Pairwise comparisons of markers>5 kb apart
  Exclude individuals with >50% missing genotypes
  HW p-value cutoff: 0.0
  Min genotype % 50
  Max # mendel errors: 1
  Minimum minor allele freq. 0.05

A case-control association analysis using 4,525 SNPs reveals a peak of allele-to-phenotype association between 32,239,934-32,546,697 bp on chromosome 16 (LG-J), suggesting a locus conditioning BSR resistance is in this region. Percent association is the percent of alleles that were correctly called. Forty-four SNPs are in very high linkage disequilibrium with the phenotype, ranking from 97.6 to 100% association for the case (i.e., susceptible) category and 95.1 to 99.3% association for the control (i.e., resistant) category (see Table 7). These markers are ideal targets for marker assay design and marker assisted selection.

As shown on FIG. 2, chi square values generated in the case-control analysis plotted against physical position of 4,525 SNPs reveals a peak of SNP to trait association between 32,239,934-32,546,697 bp on chromosome 16, suggesting a locus conditioning BSR resistance is in this region.

TABLE 6

Line counts used in this study

| No. Soybean Lines | Phenotype/haplotype |
|---|---|
| 336 | Susceptible |
| 51 | Rbs3a |
| 56 | Rbs3b |
| 80 | Rbs3b hidden |

TABLE 7

SNPs have a high association between 336 susceptible (case) and 187 resistant (control) lines.

| Name | Map position (cM) | Physical position (bp) | RES allele | SUS allele | Case, Control Ratio Counts | Case, Control Frequencies | Chi square | P value |
|---|---|---|---|---|---|---|---|---|
| Gm16: 32543279 | 83.99 | 32543279 | CC | AA | 548:4, 10:292 | 0.993, 0.033 | 793.772 | 1.22E−174 |
| Gm16: 32544128 | 83.99 | 32544128 | TT | AA | 548:8, 4:282 | 0.986, 0.014 | 789.612 | 9.79E−174 |
| Gm16: 32544169 | 83.99 | 32544169 | AA | CC | 552:8, 2:266 | 0.986, 0.007 | 783.419 | 2.17E−172 |
| Gm16: 32545642 | 84.01 | 32545642 | AA | TT | 544:6, 8:284 | 0.989, 0.027 | 781.257 | 6.41E−172 |
| Gm16: 32544181 | 83.99 | 32544181 | AA | CC | 546:8, 2:268 | 0.986, 0.007 | 779.694 | 1.40E−171 |
| Gm16: 32545680 | 84.01 | 32545680 | TT | CC | 538:4, 6:264 | 0.993, 0.022 | 767.512 | 6.25E−169 |
| Gm16: 32291307 | 82.94 | 32291307 | AA | GG | 522:10, 4:290 | 0.981, 0.014 | 766.517 | 1.03E−168 |
| Gm16: 32543387 | 83.99 | 32543387 | TT | CC | 534:10, 6:274 | 0.982, 0.021 | 754.546 | 4.12E−166 |
| Gm16: 32284137 | 82.9 | 32284137 | TT | CC | 526:10, 6:280 | 0.981, 0.021 | 753.295 | 7.71E−166 |
| Gm16: 32544094 | 83.99 | 32544094 | AA | GG | 532:6, 12:280 | 0.989, 0.041 | 752.779 | 9.98E−166 |
| Gm16: 32543360 | 83.99 | 32543360 | CC | TT | 540:4, 14:270 | 0.993, 0.049 | 749.953 | 4.11E−165 |
| Gm16: 32546349 | 84.02 | 32546349 | CC | TT | 560:4, 12:246 | 0.993, 0.047 | 749.17 | 6.08E−165 |
| Gm16: 32324276 | 83.09 | 32324276 | TT | CC | 534:6, 12:274 | 0.989, 0.042 | 748.214 | 9.81E−165 |
| Gm16: 32544455 | 84 | 32544455 | CC | GG | 530:6, 8:260 | 0.989, 0.030 | 742.144 | 2.05E−163 |
| Gm16: 32346680 | 83.17 | 32346680 | GG | AA | 516:10, 4:272 | 0.981, 0.014 | 741.68 | 2.58E−163 |
| Gm16: 32543724 | 83.99 | 32543724 | GG | AA | 530:10, 6:264 | 0.981, 0.022 | 739.945 | 6.16E−163 |

TABLE 7-continued

SNPs have a high association between 336 susceptible (case) and 187 resistant (control) lines.

| Name | Map position (cM) | Physical position (bp) | RES allele | SUS allele | Case, Control Ratio Counts | Case, Control Frequencies | Chi square | P value |
|---|---|---|---|---|---|---|---|---|
| Gm16: 32546343 | 84.02 | 32546343 | TT | AA | 560:6, 12:240 | 0.989, 0.048 | 735.425 | 5.92E−162 |
| Gm16: 32543241 | 83.98 | 32543241 | AA | TT | 534:8, 12:268 | 0.985, 0.043 | 735.16 | 6.76E−162 |
| Gm16: 32542545 | 83.98 | 32542545 | AA | GG | 518:6, 6:254 | 0.989, 0.023 | 730.796 | 6.01E−161 |
| Gm16: 32286588 | 82.91 | 32286588 | AA | GG | 490:8, 8:290 | 0.984, 0.027 | 729.153 | 1.37E−160 |
| Gm16: 32546309 | 84.02 | 32546309 | TT | CC | 540:4, 8:232 | 0.993, 0.033 | 728.375 | 2.02E−160 |
| Gm16: 32282532 | 82.89 | 32282532 | AA | TT | 502:4, 8:266 | 0.992, 0.029 | 728.152 | 2.26E−160 |
| Gm16: 32540234 | 83.95 | 32540234 | GG | TT | 480:4, 6:280 | 0.992, 0.021 | 727.726 | 2.80E−160 |
| Gm16: 32346259 | 83.17 | 32346259 | TT | CC | 532:10, 10:262 | 0.982, 0.037 | 726.592 | 4.94E−160 |
| Gm16: 32546697 | 84.02 | 32546697 | GG | CC | 502:8, 8:276 | 0.984, 0.028 | 725.885 | 7.03E−160 |
| Gm16: 32286461 | 82.91 | 32286461 | CC | GG | 510:8, 8:254 | 0.985, 0.029 | 725.013 | 1.09E−159 |
| Gm16: 32542834 | 83.98 | 32542834 | GG | AA | 520:4, 8:246 | 0.992, 0.031 | 724.27 | 1.58E−159 |
| Gm16: 32346754 | 83.17 | 32346754 | TT | CC | 506:8, 6:264 | 0.984, 0.022 | 723.348 | 2.50E−159 |
| Gm16: 32286518 | 82.91 | 32286518 | GG | AA | 500:10, 8:280 | 0.980, 0.028 | 722.002 | 4.91E−159 |
| Gm16: 32542809 | 83.98 | 32542809 | AA | GG | 524:2, 8:232 | 0.996, 0.033 | 720.159 | 1.24E−158 |
| Gm16: 32545807 | 84.01 | 32545807 | AA | CC | 530:8, 12:256 | 0.985, 0.045 | 718.177 | 3.33E−158 |
| Gm16: 32239934 | 82.63 | 32239934 | TT | AA | 498:12, 4:272 | 0.976, 0.014 | 718.141 | 3.40E−158 |
| Gm16: 32544481 | 84 | 32544481 | CC | TT | 536:6, 12:244 | 0.989, 0.047 | 717.256 | 5.29E−158 |
| Gm16: 32346987 | 83.17 | 32346987 | GG | AA | 510:8, 10:266 | 0.985, 0.036 | 716.505 | 7.70E−158 |
| Gm16: 32347808 | 83.17 | 32347808 | TT | AA | 506:12, 8:270 | 0.977, 0.029 | 710.795 | 1.34E−156 |
| Gm16: 32540201 | 83.95 | 32540201 | GG | TT | 480:10, 4:274 | 0.980, 0.014 | 709.049 | 3.22E−156 |
| Gm16: 32546282 | 84.02 | 32546282 | AA | GG | 538:4, 8:214 | 0.993, 0.036 | 706.712 | 1.04E−155 |
| Gm16: 32286403 | 82.91 | 32286403 | AA | TT | 472:0, 6:254 | 1.000, 0.023 | 706.131 | 1.39E−155 |
| Gm16: 32545360 | 84.01 | 32545360 | TT | CC | 526:6, 10:236 | 0.989, 0.041 | 705.551 | 1.86E−155 |
| Gm16: 32285402 | 82.9 | 32285402 | AA | TT | 514:10, 6:246 | 0.981, 0.024 | 705.133 | 2.29E−155 |
| Gm16: 32544988 | 84 | 32544988 | AA | GG | 518:8, 8:238 | 0.985, 0.033 | 700.064 | 2.90E−154 |
| Gm16: 32286428 | 82.91 | 32286428 | AA | CC | 494:6, 10:258 | 0.988, 0.037 | 699.047 | 4.82E−154 |
| Gm16: 32283215 | 82.89 | 32283215 | TT | CC | 506:12, 12:266 | 0.977, 0.043 | 693.903 | 6.33E−153 |
| Gm16: 32454541 | 83.52 | 32454541 | CC | TT | 484:8, 6:256 | 0.984, 0.023 | 693.648 | 7.20E−153 |

Example 2. Genotyping Assay for 91 Soybean Varieties

A genotyping assay was developed to assay marker locus Gm16:32544169 of Example 1, which is highly associated with resistance to BSR infection regardless of the particular source of the resistance and was useful for distinguishing plants with BSR resistance from plants with susceptibility to BSR infection. Marker locus Gm16:32544169 was analyzed in ninety-one soybean varieties displaying BSR resistance or BSR susceptibility phenotypes. For comparison, marker loci S01584-1, S04831-1, S16015-001 and S16023-001 were also analyzed in all ninety-one soybean varieties. Haplotypes that include marker loci marker loci S01584-1, S04831-1, S16015-001 and S16023-001 have been used previously to detect the rbs3a haplotypes, rbs3b haplotype, and the rbs3b hidden haplotype. (see. e.g., WO 2014/150226, the contents of which are hereby incorporated by reference in their entirety).

The scoring system for split stem symptoms (BRSTM) and/or leaf scorch symptoms (BSRLF) was used to estimate the affected leaf area based on a visual assessment of incidence-by-severity for the plot. A 1-9 scale was used based on total leaf area of plot affected:

9=no symptoms,
8=slight symptoms (a few chlorotic spots can be found),
7=about 15% affected leaf area,
6=30% affected leaf area,
5=about 40% total leaf area affected,
4=50% affected leaf area,
3=60% affected leaf area,
2=70% affected leaf area,
1=>80% affected leaf area.

Split stems were scored based on the percent of brown nodes as follows:

9=clean,
8=slight browning (1 or 2 nodes),
1=nearly the entire plant with brown nodes.

Soybean varieties with a BSR score of 7 to 9 were considered resistant to BSR infection. As shown in Table 8, Gm16:32544169 was in perfect association between resistance and susceptibility to BSR infection in all ninety-one varieties regardless of the type or source of BSR resistance.

TABLE 8

Phenotypic data summary.

| | | | Allele Call | | | | |
|---|---|---|---|---|---|---|---|
| Soybean Variety | Type | BSR Score | S01584-1 | S04831-1 | Gm16: 32544169 | S16015-001 | S16023-001 |
| V1 | Rbs3A | 9 | 3_3 | 1_1 | 1_1 | 4_4 | 4_4 |
| V2 | Rbs3A | 9 | 3_3 | 1_1 | 1_1 | 4_4 | 4_4 |
| V3 | Rbs3A | 9 | 3_3 | 1_1 | 1_1 | 4_4 | 4_4 |
| V4 | Rbs3A | 9 | 3_3 | 1_1 | 1_1 | 2_2 | 4_4 |
| V5 | Rbs3B | 9 | 3_3 | 1_3 | 1_1 | 4_4 | 2_2 |

TABLE 8-continued

Phenotypic data summary.

| Soybean Variety | Type | BSR Score | Allele Call | | | | |
|---|---|---|---|---|---|---|---|
| | | | S01584-1 | S04831-1 | Gm16: 32544169 | S16015-001 | S16023-001 |
| V6 | Rbs3A | 8 | 3_3 | 1_1 | 1_1 | 4_4 | 4_4 |
| V7 | Rbs3A | 8 | 3_3 | 1_1 | 1_1 | 4_4 | 4_4 |
| V8 | Rbs3A | 8 | 3_3 | 1_3 | 1_1 | 4_4 | 4_4 |
| V9 | Rbs3A | 8 | 3_3 | 1_1 | 1_1 | 2_2 | 4_4 |
| V10 | Rbs3A | 8 | 3_3 | 1_1 | 1_1 | 2_2 | 4_4 |
| V11 | Rbs3A | 8 | 3_3 | 1_1 | 1_1 | 2_2 | 4_4 |
| V12 | 3b hidden | 8 | 3_3 | 3_3 | 1_1 | 4_4 | 4_4 |
| V13 | Rbs3A | 8 | 3_3 | 1_1 | 1_1 | 2_2 | 4_4 |
| V14 | Rbs3A | 8 | 3_3 | 1_1 | 1_1 | 2_2 | 4_4 |
| V15 | Rbs3b | 8 | 3_3 | 3_3 | 1_1 | 4_4 | 2_2 |
| V16 | Rbs3A | 8 | 3_3 | 1_1 | 1_1 | 2_2 | 4_4 |
| V17 | Rbs3b | 8 | 3_3 | 3_3 | 1_1 | 4_4 | 2_2 |
| V18 | Rbs3b | 8 | 3_3 | 3_3 | 1_1 | 4_4 | 2_2 |
| V19 | Rbs3b | 8 | 3_3 | 3_3 | 1_1 | 4_4 | 2_2 |
| V20 | Rbs3A | 8 | 3_3 | 1_1 | 1_1 | 2_2 | 4_4 |
| V21 | Rbs3A | 8 | 3_3 | 1_1 | 1_1 | 4_4 | 4_4 |
| V22 | Rbs3A | 8 | 3_3 | 1_3 | 1_1 | 2_2 | 4_4 |
| V23 | Rbs3b | 8 | 3_3 | 3_3 | 1_1 | 4_4 | 2_2 |
| V24 | Rbs3A | 7 | 3_3 | 1_1 | 1_1 | 2_2 | 4_4 |
| V25 | 3b hidden | 7 | 3_3 | 3_3 | 1_1 | 4_4 | 4_4 |
| V26 | Rbs3A | 7 | 3_3 | 1_1 | 1_1 | 4_4 | 4_4 |
| V27 | Rbs3b | 7 | 3_3 | 3_3 | 1_1 | 4_4 | 2_2 |
| V28 | Rbs3b | 7 | 3_3 | 3_3 | 1_1 | 4_4 | 2_2 |
| V29 | Rbs3A | 7 | 3_3 | 1_1 | 1_1 | 2_2 | 4_4 |
| V30 | Rbs3b | 7 | 3_3 | 3_3 | 1_1 | 4_4 | 2_2 |
| V31 | Rbs3b | 7 | 3_3 | 3_3 | 1_1 | 4_4 | 2_2 |
| V32 | Rbs3A | 7 | 3_3 | 1_1 | 1_1 | 2_2 | 4_4 |
| V33 | Rbs3b | 7 | 3_3 | 3_3 | 1_1 | 4_4 | 2_2 |
| V34 | 3b hidden | 7 | 3_3 | 3_3 | 1_1 | 4_4 | 4_4 |
| V35 | Rbs3b | 7 | 3_3 | 3_3 | 1_1 | 4_4 | 2_2 |
| V36 | Rbs3b | 7 | 3_3 | 3_3 | 1_1 | 4_4 | 2_2 |
| V37 | 3b hidden | 7 | 3_3 | 3_3 | 1_1 | 4_4 | 4_4 |
| V38 | Rbs3b | 7 | 3_3 | 3_3 | 1_1 | 4_4 | 2_2 |
| V39 | Rbs3b | 7 | 3_3 | 3_3 | 1_1 | 4_4 | 2_2 |
| V40 | Mod. Sus. | 6 | 1_1 | 1_1 | 2_2 | 4_4 | 4_4 |
| V41 | Mod. Sus. | 6 | 1_1 | 1_1 | 2_2 | 4_4 | 4_4 |
| V42 | Mod. Sus. | 6 | 1_1 | 1_1 | 2_2 | 4_4 | 4_4 |
| V43 | Mod. Sus. | 6 | 1_1 | 1_1 | 2_2 | 4_4 | 4_4 |
| V44 | Mod. Sus. | 6 | 1_1 | 1_1 | 2_2 | 4_4 | 4_4 |
| V45 | Mod. Sus. | 6 | 1_1 | 1_1 | 2_2 | 4_4 | 4_4 |
| V46 | Mod. Sus. | 6 | 1_1 | 1_1 | 2_2 | 4_4 | 4_4 |
| V47 | Mod. Sus. | 6 | 1_1 | 1_1 | 2_2 | 4_4 | 4_4 |
| V48 | Mod. Sus. | 6 | 1_1 | 1_1 | 2_2 | 4_4 | 4_4 |
| V49 | Mod. Sus. | 6 | 1_1 | 1_1 | 2_2 | 4_4 | 4_4 |
| V50 | Mod. Sus. | 6 | 3_3 | 3_3 | 2_2 | 4_4 | 4_4 |
| V51 | Mod. Sus. | 5 | 1_1 | 1_1 | 2_2 | 4_4 | 4_4 |
| V52 | Mod. Sus. | 5 | 1_1 | 1_1 | 2_2 | 4_4 | 4_4 |
| V53 | Mod. Sus. | 5 | 1_1 | 1_1 | 2_2 | 4_4 | 4_4 |
| V54 | Mod. Sus. | 5 | 1_1 | 1_1 | 2_2 | 4_4 | 4_4 |
| V55 | Mod. Sus. | 5 | 1_1 | 1_1 | 2_2 | 4_4 | 4_4 |
| V56 | Mod. Sus. | 5 | 1_1 | 1_1 | 2_2 | 4_4 | 4_4 |
| V57 | Mod. Sus. | 5 | 1_1 | 1_1 | 2_2 | 4_4 | 4_4 |
| V58 | Mod. Sus. | 5 | 1_1 | 1_1 | 2_2 | 4_4 | 4_4 |
| V59 | Mod. Sus. | 5 | 1_1 | 1_1 | 2_2 | 4_4 | 4_4 |
| V60 | Mod. Sus. | 5 | 1_1 | 1_1 | 2_2 | 4_4 | 4_4 |
| V61 | Mod. Sus. | 5 | 3_3 | 3_3 | 2_2 | 4_4 | 4_4 |
| V62 | Mod. Sus. | 5 | 1_1 | 1_1 | 2_2 | 4_4 | 4_4 |
| V63 | Mod. Sus. | 5 | 3_3 | 3_3 | 2_2 | 2_2 | 4_4 |
| V64 | Mod. Sus. | 5 | 3_3 | 3_3 | 2_2 | 4_4 | 4_4 |
| V65 | Mod. Sus. | 5 | 1_1 | 1_1 | 2_2 | 4_4 | 2_2 |
| V66 | Mod. Sus. | 5 | 1_1 | 1_1 | 2_2 | 4_4 | 4_4 |
| V67 | Mod. Sus. | 5 | 1_1 | 1_1 | 2_2 | 4_4 | 4_4 |
| V68 | Mod. Sus. | 5 | 3_3 | 3_3 | 2_2 | 4_4 | 4_4 |
| V69 | Mod. Sus. | 5 | 1_1 | 1_1 | 2_2 | 4_4 | 4_4 |
| V70 | Mod. Sus. | 4 | 1_1 | 1_1 | 2_2 | 4_4 | 4_4 |
| V71 | Mod. Sus. | 4 | 1_1 | 1_1 | 2_2 | 4_4 | 4_4 |
| V72 | Mod. Sus. | 4 | 1_1 | 1_1 | 2_2 | 4_4 | 4_4 |
| V73 | Mod. Sus. | 4 | 1_1 | 1_1 | 2_2 | 4_4 | 4_4 |
| V74 | Mod. Sus. | 4 | 1_1 | 1_1 | 2_2 | 4_4 | 4_4 |
| V75 | Mod. Sus. | 4 | 1_1 | 1_1 | 2_2 | 4_4 | 4_4 |
| V76 | Mod. Sus. | 4 | 1_1 | 1_1 | 2_2 | 4_4 | 4_4 |
| V77 | Mod. Sus. | 4 | 1_1 | 1_1 | 2_2 | 4_4 | 4_4 |
| V78 | Mod. Sus. | 4 | 1_1 | 1_1 | 2_2 | 4_4 | 4_4 |

TABLE 8-continued

Phenotypic data summary.

| Soybean Variety | Type | BSR Score | Allele Call | | | | |
|---|---|---|---|---|---|---|---|
| | | | S01584-1 | S04831-1 | Gm16: 32544169 | S16015-001 | S16023-001 |
| V79 | Mod. Sus. | 4 | 1_1 | 1_1 | 2_2 | 4_4 | 4_4 |
| V80 | Mod. Sus. | 4 | 1_1 | 1_1 | 2_2 | 4_4 | 4_4 |
| V81 | Mod. Sus. | 4 | 1_1 | 1_1 | 2_2 | 4_4 | 4_4 |
| V82 | Mod. Sus. | 4 | 1_1 | 1_1 | 2_2 | 2_2 | 4_4 |
| V83 | Mod. Sus. | 4 | 3_3 | 3_3 | 2_2 | 4_4 | 4_4 |
| V84 | Mod. Sus. | 4 | 1_1 | 1_1 | 2_2 | 4_4 | 2_2 |
| V85 | Mod. Sus. | 3 | 1_1 | 1_1 | 2_2 | 4_4 | 4_4 |
| V86 | Mod. Sus. | 3 | 1_1 | 1_1 | 2_2 | 4_4 | 4_4 |
| V87 | Mod. Sus. | 3 | 1_1 | 1_1 | 2_2 | 4_4 | 4_4 |
| V88 | Mod. Sus. | 3 | 1_1 | 1_1 | 2_2 | 4_4 | 2_2 |
| V89 | Mod. Sus. | 3 | 3_3 | 3_3 | 2_2 | 2_2 | 4_4 |
| V90 | Mod. Sus. | 2 | 1_1 | 1_1 | 2_2 | 4_4 | 4_4 |
| V91 | Mod. Sus. | 2 | 1_1 | 1_1 | 2_2 | 4_4 | 4_4 |

3b hidden = Rbs3b hidden
Mod. Sus. = moderately susceptible

Example 3. Case Control Association Analysis for Marker Loci Associated with an rbs3a Haplotype In order to identify marker loci that are highly associated an rbs3a haplotype, a case-control study similar to Example 1 was conducted, except that only samples with the rbs3a haplotype were placed in the "case" group, whereas all offtypes, i.e., rbs3b, rbs3b hidden, and susceptible haplotypes, were placed in the "control" (see Table 9).
Haploview Settings:
  Do Association Test
  Case/Control Data
  Ignore Pairwise comparisons of markers>5 kb apart
  Exclude individuals with >50% missing genotypes
  HW p-value cutoff: 0.0
  Min genotype % 50
  Max # mendel errors: 1
  Minimum minor allele freq. 0.05

Twenty-two SNPs are in very high linkage disequilibrium with the phenotype, ranking from 95.7% to 100% association for the case (i.e., rbs3a haplotype) category and 99.2% to 100% association for the control (i.e., offtype) category (see Table 9). These markers are ideal targets for marker assay design and marker assisted selection.

TABLE 9

SNPs with high association with an rbs3a haplotype.

| Name | Map position (cM) | Physical position (bp) | Rbs3a allele | Offtype allele | Case, Control Ratio Counts | Case, Control Frequencies | Chi square | P value |
|---|---|---|---|---|---|---|---|---|
| Gm16: 32297214 | 82.97 | 32297214 | G | C | 146:0, 2:960 | 1.000, 0.002 | 1090.755 | 3.38E−239 |
| Gm16: 32340207 | 83.15 | 32340207 | T | A | 136:0, 4:970 | 1.000, 0.004 | 1073.857 | 1.59E−235 |
| Gm16: 32273397 | 82.83 | 32273397 | A | T | 136:4, 4:980 | 0.971, 0.004 | 1051.83 | 9.74E−231 |
| Gm16: 32284255 | 82.9 | 32284255 | C | T | 140:2, 0:926 | 0.986, 0.000 | 1050.688 | 1.72E−230 |
| Gm16: 32296634 | 82.97 | 32296634 | T | C | 134:2, 0:928 | 0.985, 0.000 | 1046.098 | 1.72E−229 |
| Gm16: 32297269 | 82.97 | 32297269 | A | G | 140:6, 0:942 | 0.959, 0.000 | 1036.685 | 1.91E−227 |
| Gm16: 32543353 | 83.99 | 32543353 | C | T | 146:2, 6:948 | 0.986, 0.006 | 1035.265 | 3.88E−227 |
| Gm16: 32287149 | 82.91 | 32287149 | G | C | 136:2, 4:946 | 0.986, 0.004 | 1034.894 | 4.67E−227 |
| Gm16: 32278942 | 82.86 | 32278942 | A | G | 140:6, 2:952 | 0.959, 0.002 | 1031.073 | 3.16E−226 |
| Gm16: 32297835 | 82.98 | 32297835 | G | A | 138:4, 2:936 | 0.972, 0.002 | 1027.857 | 1.58E−225 |
| Gm16: 32552252 | 84.08 | 32552252 | A | C | 138:4, 0:920 | 0.972, 0.000 | 1027.617 | 1.78E−225 |
| Gm16: 32297287 | 82.98 | 32297287 | C | T | 140:6, 0:928 | 0.959, 0.000 | 1023.247 | 1.59E−224 |
| Gm16: 32570539 | 84.26 | 32570539 | C | T | 134:4, 2:930 | 0.971, 0.002 | 1017.004 | 3.62E−223 |
| Gm16: 32459125 | 83.54 | 32459125 | T | A | 128:4, 4:954 | 0.970, 0.004 | 1016.133 | 5.59E−223 |
| Gm16: 32296468 | 82.97 | 32296468 | C | A | 136:2, 4:924 | 0.986, 0.004 | 1013.812 | 1.79E−222 |
| Gm16: 32109926 | 81.71 | 32109926 | A | C | 140:4, 4:934 | 0.972, 0.004 | 1013.772 | 1.82E−222 |
| Gm16: 32562910 | 84.18 | 32562910 | A | C | 134:6, 4:958 | 0.957, 0.004 | 1013.213 | 2.41E−222 |
| Gm16: 32339979 | 83.14 | 32339979 | T | G | 128:4, 4:950 | 0.970, 0.004 | 1012.367 | 3.68E−222 |
| Gm16: 32296941 | 82.97 | 32296941 | A | T | 148:4, 8:950 | 0.974, 0.008 | 1012.078 | 4.26E−222 |
| Gm16: 32464136 | 83.55 | 32464136 | A | G | 148:0, 4:892 | 1.000, 0.004 | 1011.988 | 4.45E−222 |
| Gm16: 32298201 | 82.98 | 32298201 | A | T | 144:2, 4:910 | 0.986, 0.004 | 1010.427 | 9.72E−222 |
| Gm16: 32300241 | 82.99 | 32300241 | T | A | 110:2, 2:938 | 0.982, 0.002 | 1010.372 | 9.99E−222 |

Example 4. Case Control Association Analysis for Marker Loci Associated an rbs3b Haplotype In order to identify marker loci that are highly associated with an rbs3 haplotype, a case-control study similar to Example 1 was conducted, except that only samples with the rbs3b haplotype were placed in the "case" group, whereas all offtypes, i.e., rbs3a, rbs3b hidden, and susceptible haplotypes, were placed in the "control" group (see Table 10).

Haploview Settings:
  Do Association Test
  Case/Control Data
  Ignore Pairwise comparisons of markers>5 kb apart
  Exclude individuals with >50% missing genotypes
  HW p-value cutoff: 0.0
  Min genotype % 50
  Max # mendel errors: 1
  Minimum minor allele freq. 0.05

Forty-four SNPs are in very high linkage disequilibrium with the phenotype, ranking from 95.9% to 100% association for the case (i.e., rbs3b haplotype) category and 99.4% to 100% association for the control (i.e., offtype) category (see Table 10). These markers are ideal targets for marker assay design and marker assisted selection.

TABLE 10

SNPs with high association with an rbs3b haplotype.

| Name | Map position (cM) | Physical position (bp) | Rbs3b allele | Offtype allele | Case, Control Ratio Counts | Case, Control Frequencies | Chi square | P value |
|---|---|---|---|---|---|---|---|---|
| Gm16: 32271645 | 82.82 | 32271645 | G | C | 108:0, 0:1026 | 1.000, 0.000 | 1134 | 1.3E−248 |
| Gm16: 32271574 | 82.82 | 32271574 | T | C | 120:0, 2:1002 | 1.000, 0.002 | 1103.371 | 6.1E−242 |
| Gm16: 32346412 | 83.17 | 32346412 | A | C | 110:2, 0:1006 | 0.982, 0.000 | 1095.857 | 2.6E−240 |
| Gm16: 32339865 | 83.14 | 32339865 | T | C | 116:0, 0:978 | 1.000, 0.000 | 1094 | 6.7E−240 |
| Gm16: 32275584 | 82.84 | 32275584 | T | G | 120:0, 4:1010 | 1.000, 0.004 | 1093.09 | 1.0E−239 |
| Gm16: 32287898 | 82.92 | 32287898 | C | T | 116:0, 2:992 | 1.000, 0.002 | 1088.991 | 8.2E−239 |
| Gm16: 32455251 | 83.52 | 32455251 | A | C | 116:0, 2:982 | 1.000, 0.002 | 1079.158 | 1.1E−236 |
| Gm16: 32346356 | 83.17 | 32346356 | A | G | 114:2, 2:1000 | 0.983, 0.002 | 1075.399 | 7.3E−236 |
| Gm16: 32570462 | 84.25 | 32570462 | T | C | 114:2, 2:1000 | 0.983, 0.002 | 1075.399 | 7.3E−236 |
| Gm16: 32665882 | 84.99 | 32665882 | G | C | 120:0, 2:970 | 1.000, 0.002 | 1071.888 | 4.3E−235 |
| Gm16: 32563711 | 84.19 | 32563711 | A | T | 108:0, 0:962 | 1.000, 0.000 | 1070 | 1.1E−234 |
| Gm16: 32267736 | 82.8 | 32267736 | C | T | 104:2, 0:986 | 0.981, 0.000 | 1069.227 | 1.6E−234 |
| Gm16: 32269647 | 82.81 | 32269647 | G | T | 112:0, 2:976 | 1.000, 0.002 | 1068.687 | 2.1E−234 |
| Gm16: 32525289 | 83.8 | 32525289 | A | G | 118:0, 0:950 | 1.000, 0.000 | 1068 | 3.0E−234 |
| Gm16: 32211313 | 82.35 | 32211313 | A | T | 82:2, 0:1010 | 0.976, 0.000 | 1065.842 | 8.8E−234 |
| Gm16: 32347756 | 83.17 | 32347756 | T | G | 108:0, 0:956 | 1.000, 0.000 | 1064 | 2.2E−233 |
| Gm16: 32271714 | 82.82 | 32271714 | A | T | 116:2, 2:984 | 0.983, 0.002 | 1062.495 | 4.7E−233 |
| Gm16: 32550454 | 84.06 | 32550454 | A | G | 96:0, 0:966 | 1.000, 0.000 | 1062 | 6.0E−233 |
| Gm16: 32550524 | 84.06 | 32550524 | A | C | 106:0, 2:976 | 1.000, 0.002 | 1061.75 | 6.8E−233 |
| Gm16: 32517555 | 83.73 | 32517555 | G | A | 110:2, 2:984 | 0.982, 0.002 | 1054.766 | 2.2E−231 |
| Gm16: 32464778 | 83.56 | 32464778 | G | C | 110:0, 0:944 | 1.000, 0.000 | 1054 | 3.3E−231 |
| Gm16: 32315350 | 83.06 | 32315350 | A | G | 112:2, 0:960 | 0.982, 0.000 | 1052.964 | 5.5E−231 |
| Gm16: 32263188 | 82.77 | 32263188 | A | C | 108:4, 0:984 | 0.964, 0.000 | 1052.578 | 6.7E−231 |
| Gm16: 32550442 | 84.06 | 32550442 | A | C | 92:0, 0:960 | 1.000, 0.000 | 1052 | 8.9E−231 |
| Gm16: 32217702 | 82.42 | 32217702 | T | C | 84:2, 0:992 | 0.977, 0.000 | 1050.812 | 1.6E−230 |
| Gm16: 32225387 | 82.51 | 32225387 | G | C | 106:0, 2:964 | 1.000, 0.002 | 1049.97 | 2.47E−230 |
| Gm16: 32552305 | 84.08 | 32552305 | C | T | 96:2, 0:976 | 0.980, 0.000 | 1049.93 | 2.52E−230 |
| Gm16: 32344193 | 83.16 | 32344193 | A | C | 100:2, 2:992 | 0.980, 0.002 | 1049.121 | 3.78E−230 |
| Gm16: 32349746 | 83.18 | 32349746 | A | C | 108:4, 0:980 | 0.964, 0.000 | 1048.72 | 4.62E−230 |
| Gm16: 32550443 | 84.06 | 32550443 | A | G | 88:0, 0:960 | 1.000, 0.000 | 1048 | 6.62E−230 |
| Gm16: 32271035 | 82.82 | 32271035 | T | C | 118:2, 2:964 | 0.983, 0.002 | 1045.684 | 2.11E−229 |
| Gm16: 32342403 | 83.15 | 32342403 | G | A | 104:0, 2:962 | 1.000, 0.002 | 1045.675 | 2.12E−229 |
| Gm16: 32541245 | 83.96 | 32541245 | C | T | 94:2, 0:974 | 0.979, 0.000 | 1045.561 | 2.24E−229 |
| Gm16: 32268012 | 82.8 | 32268012 | T | C | 94:0, 0:950 | 1.000, 0.000 | 1044 | 4.90E−229 |
| Gm16: 32516254 | 83.72 | 32516254 | A | G | 112:0, 6:988 | 1.000, 0.006 | 1043.426 | 6.53E−229 |
| Gm16: 32269873 | 82.81 | 32269873 | A | C | 122:4, 4:992 | 0.968, 0.004 | 1043.185 | 7.37E−229 |
| Gm16: 32344231 | 83.16 | 32344231 | T | C | 100:2, 4:1006 | 0.980, 0.004 | 1041.877 | 1.42E−228 |
| Gm16: 32550578 | 84.06 | 32550578 | T | A | 104:0, 2:958 | 1.000, 0.002 | 1041.75 | 1.51E−228 |
| Gm16: 32346483 | 83.17 | 32346483 | G | A | 80:2, 0:986 | 0.976, 0.000 | 1039.842 | 3.93E−228 |
| Gm16: 32573101 | 84.28 | 32573101 | T | C | 102:2, 2:974 | 0.981, 0.002 | 1034.524 | 5.62E−227 |
| Gm16: 32217820 | 82.42 | 32217820 | T | C | 94:4, 0:984 | 0.959, 0.000 | 1033.635 | 8.78E−227 |
| Gm16: 32324084 | 83.09 | 32324084 | T | C | 108:4, 2:984 | 0.964, 0.002 | 1033.071 | 1.16E−226 |
| Gm16: 32346915 | 83.17 | 32346915 | T | C | 110:4, 0:960 | 0.965, 0.000 | 1032.016 | 1.97E−226 |
| Gm16: 32324102 | 83.09 | 32324102 | C | G | 104:4, 2:988 | 0.963, 0.002 | 1030.953 | 1.36E−226 |

Example 5. Case Control Association Analysis for Marker Loci Associated with an rbs3b Hidden Haplotype In order to identify marker loci that are highly associated with an rbs3b hidden haplotype, a case-control study similar to Example 1 was conducted, except that only samples with the rbs3b hidden haplotype were placed in the "case" group, whereas all offtypes, i.e., rbs3a, rbs3b, and susceptible haplotypes, were placed in the "control" group (see Table 11).

Haploview Settings:
Do Association Test
Case/Control Data
Ignore Pairwise comparisons of markers>5 kb apart
Exclude individuals with >50% missing genotypes
HW p-value cutoff 0.0
Min genotype % 50
Max # mendel errors: 1
Minimum minor allele freq. 0.05

Forty-five SNPs are in very high linkage disequilibrium with the phenotype, ranking from 95.2% to 100% association for the case (i.e., rbs3b hidden haplotype) category and 99.3% to 100% association for the control (i.e., offtype) category (see Table 11). These markers are ideal targets for marker assay design and marker assisted selection.

TABLE 11

SNPs with high association with an rbs3b hidden haplotype.

| Name | Map position (cM) | Physical position (bp) | Rbs3b hidden allele | Offtype allele | Case, Control Ratio Counts | Case, Control Frequencies | Chi square | P value |
|---|---|---|---|---|---|---|---|---|
| Gm16: 32234335 | 82.59 | 32234335 | G | A | 158:0, 2:950 | 1.000, 0.002 | 1093.822 | 7.27E−240 |
| Gm16: 32233691 | 82.59 | 32233691 | A | T | 146:0, 0:932 | 1.000, 0.000 | 1078 | 2.00E−236 |
| Gm16: 32235048 | 82.6 | 32235048 | C | T | 164:4, 2:940 | 0.976, 0.002 | 1063.607 | 2.68E−233 |
| Gm16: 32297045 | 82.97 | 32297045 | T | G | 148:0, 4:942 | 1.000, 0.004 | 1060.706 | 1.15E−232 |
| Gm16: 32301650 | 83 | 32301650 | C | T | 144:0, 0:916 | 1.000, 0.000 | 1060 | 1.63E−232 |
| Gm16: 32217515 | 82.42 | 32217515 | G | A | 162:0, 4:918 | 1.000, 0.004 | 1053.29 | 4.69E−231 |
| Gm16: 32308185 | 83.04 | 32308185 | G | A | 156:0, 2:904 | 1.000, 0.002 | 1046.242 | 1.60E−229 |
| Gm16: 32459325 | 83.54 | 32459325 | C | A | 130:4, 0:948 | 0.970, 0.000 | 1045.291 | 2.57E−229 |
| Gm16: 32288737 | 82.92 | 32288737 | C | T | 146:2, 4:940 | 0.986, 0.004 | 1041.736 | 1.52E−228 |
| Gm16: 32339081 | 83.14 | 32339081 | A | G | 146:4, 2:940 | 0.973, 0.002 | 1041.736 | 1.52E−228 |
| Gm16: 32273554 | 82.83 | 32273554 | A | C | 154:4, 2:926 | 0.975, 0.002 | 1038.083 | 9.48E−228 |
| Gm16: 32268047 | 82.8 | 32268047 | A | G | 158:0, 4:902 | 1.000, 0.004 | 1033.147 | 1.12E−226 |
| Gm16: 32270524 | 82.81 | 32270524 | A | T | 148:2, 0:898 | 0.987, 0.000 | 1031.729 | 2.28E−226 |
| Gm16: 32349993 | 83.18 | 32349993 | T | G | 158:0, 4:900 | 1.000, 0.004 | 1031.195 | 2.98E−226 |
| Gm16: 32329724 | 83.11 | 32329724 | G | A | 136:2, 0:910 | 0.986, 0.000 | 1030.547 | 4.12E−226 |
| Gm16: 32236209 | 82.61 | 32236209 | T | C | 164:6, 4:932 | 0.965, 0.004 | 1030.152 | 5.02E−226 |
| Gm16: 32275786 | 82.85 | 32275786 | A | T | 156:2, 8:942 | 0.987, 0.008 | 1029.437 | 7.18E−226 |
| Gm16: 32275787 | 82.85 | 32275787 | T | G | 156:2, 8:942 | 0.987, 0.008 | 1029.437 | 7.18E−226 |
| Gm16: 32218068 | 82.42 | 32218068 | T | G | 148:2, 4:924 | 0.987, 0.004 | 1028.825 | 9.75E−226 |
| Gm16: 32230177 | 82.56 | 32230177 | A | G | 154:4, 2:916 | 0.975, 0.002 | 1028.45 | 1.18E−225 |
| Gm16: 32287161 | 82.91 | 32287161 | C | G | 160:2, 6:920 | 0.988, 0.006 | 1026.618 | 2.94E−225 |
| Gm16: 32186606 | 82.16 | 32186606 | C | G | 150:4, 2:918 | 0.974, 0.002 | 1025.507 | 5.13E−225 |
| Gm16: 32338878 | 83.14 | 32338878 | A | G | 144:4, 4:940 | 0.973, 0.004 | 1024.786 | 7.36E−225 |
| Gm16: 32182404 | 82.15 | 32182404 | G | A | 152:4, 0:898 | 0.974, 0.000 | 1022.42 | 2.40E−224 |
| Gm16: 32323924 | 83.09 | 32323924 | C | T | 158:4, 6:932 | 0.975, 0.006 | 1022.256 | 2.61E−224 |
| Gm16: 32319745 | 83.08 | 32319745 | C | A | 168:4, 2:892 | 0.977, 0.002 | 1021.965 | 3.02E−224 |
| Gm16: 32270866 | 82.82 | 32270866 | T | C | 154:2, 6:922 | 0.987, 0.006 | 1020.927 | 5.08E−224 |
| Gm16: 32307865 | 83.04 | 32307865 | T | A | 150:2, 6:922 | 0.987, 0.006 | 1015.792 | 6.63E−223 |
| Gm16: 32341072 | 83.15 | 32341072 | G | A | 148:2, 6:924 | 0.987, 0.006 | 1015.1 | 9.38E−223 |
| Gm16: 32204594 | 82.27 | 32204594 | A | C | 156:4, 4:912 | 0.975, 0.004 | 1013.731 | 1.86E−222 |
| Gm16: 32288768 | 82.92 | 32288768 | C | A | 152:4, 4:916 | 0.974, 0.004 | 1012.432 | 3.57E−222 |
| Gm16: 32454218 | 83.52 | 32454218 | A | G | 128:6, 2:948 | 0.955, 0.002 | 1010.788 | 8.12E−222 |
| Gm16: 32321898 | 83.09 | 32321898 | T | A | 142:2, 0:882 | 0.986, 0.000 | 1009.461 | 1.58E−221 |
| Gm16: 32554984 | 84.1 | 32554984 | A | C | 146:2, 2:892 | 0.986, 0.002 | 1009.434 | 1.60E−221 |
| Gm16: 32350129 | 83.18 | 32350129 | T | C | 142:4, 4:926 | 0.973, 0.004 | 1008.866 | 2.12E−221 |
| Gm16: 32243083 | 82.65 | 32243083 | T | A | 150:2, 0:872 | 0.987, 0.000 | 1008.214 | 2.94E−221 |
| Gm16: 32291418 | 82.94 | 32291418 | G | A | 156:4, 4:906 | 0.975, 0.004 | 1008.018 | 3.25E−221 |
| Gm16: 32213522 | 82.37 | 32213522 | G | A | 146:6, 0:904 | 0.961, 0.000 | 1007.628 | 3.95E−221 |
| Gm16: 32217755 | 82.42 | 32217755 | T | C | 156:4, 0:878 | 0.975, 0.000 | 1007.46 | 4.29E−221 |
| Gm16: 32541584 | 83.97 | 32541584 | C | T | 156:6, 6:932 | 0.963, 0.006 | 1006.521 | 6.87E−221 |
| Gm16: 32554335 | 84.1 | 32554335 | C | T | 146:4, 0:888 | 0.973, 0.000 | 1005.789 | 9.91E−221 |
| Gm16: 32509795 | 83.7 | 32509795 | A | T | 152:2, 6:908 | 0.987, 0.007 | 1005.054 | 1.43E−220 |
| Gm16: 32239092 | 82.63 | 32239092 | C | T | 148:6, 2:912 | 0.961, 0.002 | 1003.705 | 2.81E−220 |
| Gm16: 32491511 | 83.64 | 32491511 | G | A | 158:8, 2:910 | 0.952, 0.002 | 1001.967 | 6.71E−220 |
| Gm16: 32270738 | 82.82 | 32270738 | G | T | 152:6, 4:918 | 0.962, 0.004 | 1001.065 | 1.05E−219 |

Example 6. Nonlimiting Exemplary Genotyping Assay

Genotyping assays may be developed to characterize, identify, and/or select resistance or susceptible alleles of various marker loci associated with resistance to BSR infection. Markers are screened against various known and resistant and susceptible soybean plants. Any methodology can be deployed to use this information, including but not limited to any one or more of sequencing or marker methods.

In one example, sample tissue, including tissue from soybean leaves or seeds, can be extract obtained from leaf discs can be screened with the markers using a TAQMAN® PCR assay system (Life Technologies, Grand Island, N.Y., USA).

Genomic DNA may be extracted from leaf tissue using a modification of the CTAB (cetyltriethylammonium bromide, Sigma H5882) method described by Stacey & Isaac (Methods in Molecular Biology, Vol. 28: Protocols for Nucleic Acid Analysis by Nonradioactive Probes, Ed: Isaac, Humana Press Inc, Totowa, N.J. 1994, Ch 2, pp. 9-15). Approximately 100-200 mg of tissue is ground into powder in liquid nitrogen and homogenized in 1 ml of CTAB extraction buffer (2% CTAB, 0.02 M EDTA, 0.1 M Tris-Cl pH 8, 1.4 M NaCl, 25 mM DTT) for 30 min at 65° C. Homogenized samples are then cooled at room temperature for 15 minutes before a single protein extraction with approximately 1 ml 24:1 v/v chloroform:octanol is done. Samples are then centrifuged for 7 minutes at 13,000 rpm and the upper layer of supernatant is collected using wide-mouthed pipette tips. DNA is precipitated from the supernatant by incubation in 95% ethanol on ice for 1 hour. DNA threads are spooled onto a glass hook, washed in 75% ethanol containing 0.2 M sodium acetate for 10 minutes, air-dried for 5 minutes and resuspended in TE buffer. Five µl RNAse A may be added to the samples, which are then incubated at 37° C. for 1 hour.

Exemplary TAQMAN® PCR conditions are provided.

TAQMAN® Assay Conditions

Reaction Mixture (Total Volume=5 µl):

| | |
|---|---|
| Genomic DNA (dried) | 16 ng |
| DDH20 | 2.42 µl |
| Klearkall Masterraix | 2.5 µl |
| Forward primer (100 µM) | 0.0375 µl |
| Reverse primer (100 µM) | 0.0375 µl |
| Probe 1 (100 µM) | 0.005 µl |
| Probe 2 (100 µM) | 0.005 µl |

Reaction Conditions:

| | |
|---|---|
| 94° C. | 10 min 1 cycle |
| 40 cycles of the following: | |
| 94° C. | 30 sec |
| 60° C. | 60 sec |

Klearkall Mastermix is available from KBioscience Ltd. (Hoddesdon, UK).

A non-limiting list of primers and probes suitable for the detection of various SNPs are provided in Table 5.

That which is claimed:

1. A method of selecting a soybean plant or soybean germplasm having improved resistance to brown stem rot infection, the method comprising:
   (a) detecting in the nucleic acid of a soybean plant or soybean germplasm at least one allele of one or more marker locus within or linked to a quantitative trait locus (QTL) associated with resistance to brown stem rot infection, wherein the allele positively correlates with resistance to brown stem rot infection, and wherein the one or more marker locus is Gm16: 32544169;
   (b) selecting the soybean plant or soybean germplasm comprising the at least one allele from step (a), thereby selecting a soybean plant with improved resistance to brown stem rot infection;
   (c) crossing the selected soybean plant or soybean germplasm with a second soybean plant to produce a population of progeny soybean germplasm, whereby the QTL associated with resistance to brown stem rot infection is introgressed into a subpopulation of the progeny soybean germplasm; and
   (d) collecting seeds from the progeny soybean of said cross.

2. The method of claim 1, wherein the soybean plant or soybean germplasm comprises alleles A, A of marker locus Gm16:32544169.

3. The method of claim 1, further comprising:
   before, simultaneous with or after step (a) and before step (b), the further step of detecting in the soybean plant or soybean germplasm at least one allele of one or more marker locus associated with an rbs3a haplotype, wherein the allele positively correlates with rbs3a-type resistance to brown stem rot infection, and wherein the one or more marker locus is selected from the group consisting of Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 and a combination thereof; and
   after step (a) and before, simultaneous with or after step (b), the further step of selecting the soybean plant or soybean germplasm comprising the allele of one or more marker locus associated with an rbs3a haplotype, thereby selecting a soybean plant with improved rbs3a-type resistance to brown stem rot infection.

4. The method of claim 3, wherein the marker locus associated with an rbs3a haplotype is Gm16:32296634.

5. The method of claim 3, wherein the soybean plant or soybean germplasm further comprises allele T of marker locus Gm16:32296634.

6. The method of claim 1, further comprising:
   before, simultaneous with or after step (a) and before step (b), the further step of detecting in the soybean plant or soybean germplasm at least one allele of one or more marker locus associated with an rbs3b haplotype, wherein the allele positively correlates with rbs3b-type resistance to brown stem rot infection, and wherein the one or more marker locus is selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702 Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof; and
   after step (a) and before, simultaneous with or after step (b), the further step of selecting the soybean plant or soybean germplasm comprising the allele of one or more marker locus associated with an rbs3b haplotype, thereby selecting a soybean plant with improved rbs3b-type resistance to brown stem rot infection.

7. The method of step 6, wherein the marker locus associated with an rbs3b haplotype is Gm16:32271574.

8. The method of claim 6, wherein the soybean plant or soybean germplasm further comprises allele T of marker locus Gm16:32271574.

9. The method of claim 1, further comprising:
   before, simultaneous with or after step (a) and before step (b), the further step of detecting in the soybean plant or soybean germplasm at least one allele of one or more marker locus associated with an rbs3b hidden haplotype, wherein the allele positively correlates with rbs3b-type resistance to brown stem rot infection, and wherein the one or more marker locus is selected from the group consisting of Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738
   and a combination thereof; and
   after step (a) and before, simultaneous with or after step (b), the further step of selecting the soybean plant or soybean germplasm comprising the allele of one or more marker locus associated with an rbs3b hidden haplotype, thereby selecting a soybean plant with improved rbs3b-type resistance to brown stem rot infection.

10. The method of claim 9, wherein the marker locus associated with an rbs3b hidden haplotype is Gm16:32234335.

11. The method of claim 9, wherein the soybean plant or soybean germplasm further comprises allele G of marker locus Gm16:32234335.

12. The method of claim 1, further comprising:
   before, simultaneous with or after step (a) and before step (b), the further step of detecting in the soybean plant or soybean germplasm at least one allele of one or more marker locus associated with:

(1) an rbs3a haplotype, wherein the allele positively correlates with rbs3a-type resistance to brown stem rot infection, and wherein the one or more marker locus is selected from the group consisting of Gm16:32297214, Gm16:32340207, Gm16:32273397, Gm16:32284255, Gm16:32296634, Gm16:32297269, Gm16:32543353, Gm16:32287149, Gm16:32278942, Gm16:32297835, Gm16:32552252, Gm16:32297287, Gm16:32570539, Gm16:32459125, Gm16:32296468, Gm16:32109926, Gm16:32562910, Gm16:32339979, Gm16:32296941, Gm16:32464136, Gm16:32298201, Gm16:32300241 and a combination thereof;

(2) an rbs3b haplotype, wherein the allele positively correlates with rbs3b-type resistance to brown stem rot infection, and wherein the one or more marker locus is selected from the group consisting of Gm16:32271645, Gm16:32271574, Gm16:32346412, Gm16:32339865, Gm16:32275584, Gm16:32287898, Gm16:32455251, Gm16:32346356, Gm16:32570462, Gm16:32665882, Gm16:32563711, Gm16:32267736, Gm16:32269647, Gm16:32525289, Gm16:32211313, Gm16:32347756, Gm16:32271714, Gm16:32550454, Gm16:32550524, Gm16:32517555, Gm16:32464778, Gm16:32315350, Gm16:32263188, Gm16:32550442, Gm16:32217702, Gm16:32225387, Gm16:32552305, Gm16:32344193, Gm16:32349746, Gm16:32550443, Gm16:32271035, Gm16:32342403, Gm16:32541245, Gm16:32268012, Gm16:32516254, Gm16:32269873, Gm16:32344231, Gm16:32550578, Gm16:32346483, Gm16:32573101, Gm16:32217820, Gm16:32324084, Gm16:32346915, Gm16:32324102 and a combination thereof;

(3) an rbs3b hidden haplotype, wherein the allele positively correlates with rbs3b-type resistance to brown stem rot infection, and wherein the one or more marker locus is selected from the group consisting of Gm16:32234335, Gm16:32233691, Gm16:32235048, Gm16:32297045, Gm16:32301650, Gm16:32217515, Gm16:32308185, Gm16:32459325, Gm16:32288737, Gm16:32339081, Gm16:32273554, Gm16:32268047, Gm16:32270524, Gm16:32349993, Gm16:32329724, Gm16:32236209, Gm16:32275786, Gm16:32275787, Gm16:32218068, Gm16:32230177, Gm16:32287161, Gm16:32186606, Gm16:32338878, Gm16:32182404, Gm16:32323924, Gm16:32319745, Gm16:32270866, Gm16:32307865, Gm16:32341072, Gm16:32204594, Gm16:32288768, Gm16:32454218, Gm16:32321898, Gm16:32554984, Gm16:32350129, Gm16:32243083, Gm16:32291418, Gm16:32213522, Gm16:32217755, Gm16:32541584, Gm16:32554335, Gm16:32509795, Gm16:32239092, Gm16:32491511, Gm16:32270738 and a combination thereof; or (4) a combination of (1), (2), or (3); and after step (a) and before, simultaneously with or after step (b), the further step of selecting the soybean plant or soybean germplasm comprising the allele of one or more marker locus from (1), (2), (3), or (4).

13. The method of claim 1, wherein detecting comprises:
(i) sequencing at least one of the marker loci;
(ii) amplifying a nucleic acid comprising the marker locus of each allele and detecting the resulting amplified nucleic acid comprising each marker locus;
(iii) hybridizing a nucleic acid to the marker locus of each allele under at least moderately stringent conditions and detecting the nucleic acid that hybridized to each marker locus; or
(iv) a combination of (i), (ii) or (iii).

14. The method of claim 1, wherein detecting comprises amplifying a nucleic acid sequence comprising the marker locus of each allele and detecting the resulting amplified nucleic acid comprising each marker locus.

15. The method of claim 14, wherein the amplifying comprises amplification of at least a portion of one or more genomic regions of the soybean genome selected from the group consisting of SEQ ID NOs: 1-155, 172 and a combination thereof.

16. The method of claim 15, wherein the amplification comprises providing one or more nucleic acid primers, wherein the nucleic acid primers comprise the nucleic acid sequence selected from the group consisting of SEQ ID NOs: 156 and 157.

17. The method of claim 16, wherein the detecting further comprises hybridization with one or more nucleic acid probes, wherein the nucleic acid probes comprise the nucleic acid sequence selected from the group consisting of SEQ ID NOs: 158 and 159.

18. The method of claim 1, wherein the subpopulation of the progeny soybean germplasm displays: (i) rbs3a-type resistance or improved rbs3a-type resistance to brown stem rot infection; (ii) rbs3b-type resistance or improved rbs3b-type resistance to brown stem rot infection; or (iii) a combination of (i) and (ii).

19. A method of selecting soybean plants for improved resistance to brown stem rot infection, the method comprising:
(a) providing a population of genetically diverse soybean plants;
(b) extracting genomic DNA samples from each of the soybean plants in the population;
(c) admixing a first isolated polynucleotide with each of the genomic DNA samples from step (b), wherein the first polynucleotide is capable of hybridizing with a favorable allele of a marker locus of Gm16:32544169;
(d) detecting the presence of a hybridized first polynucleotide in one or more of the genomic DNA samples, wherein the presence of the hybridized first polynucleotide indicates a soybean plant with improved resistance to brown stem rot infection; and
(e) selecting at least one soybean plant with improved resistance to brown stem rot infection from step (d);
(f) crossing a soybean plant selected in step (e) to a second soybean plant to produce a population of progeny soybean germplasm;
(g) extracting genomic DNA from each of the progeny soybean germplasm;
(h) admixing a second isolated polynucleotide with each of the genomic DNA samples from (b), wherein the second polynucleotide is capable of hybridizing with a favorable allele of a marker locus of Gm16:32544169;
(i) detecting the presence of a hybridized second polynucleotide in one or more of the genomic DNA samples from one or more of the progeny soybean germplasm, wherein the presence of the hybridized second polynucleotide indicates a progeny soybean germplasm with improved resistance to brown stem rot infection;
(j) selecting at least one progeny soybean germplasm with improved resistance to brown stem rot infection from (d); and
(k) collecting seeds from the progeny soybean of said cross.

20. The method of claim 19, wherein the isolated polynucleotide comprises a nucleic acid sequence having at least 90% sequence identity to SEQ ID NO: 158, provided that the nucleic acid sequence comprises an adenine that hybridizes to a thymidine at 32,544,169 bp of chromosome 16.

21. The method of claim 19, wherein the isolated polynucleotide comprises a nucleic acid sequence represented by SEQ ID NO: 158.

22. The method of claim 21, wherein the isolated polynucleotide comprises a detectable label.

* * * * *

SEQUENCE LISTING

```
<160> NUMBER OF SEQ ID NOS: 175

<210> SEQ ID NO 1
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32543279

<400> SEQUENCE: 1
ccatatacat acccaagtgt ggtagtatga taatattgga taatmaaaaa atagtaatag      60
aawaatgata gttctttggg cagcacaaag taaatgctaa mataaatcag acaccaggtg     120
aatatactaa agtttagcaa ataatggtac ggcagagtaa ttgaatacat gaacyaaaaa     180 tyctttttg ctaattgaaa t                                                201

<210> SEQ ID NO 2
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32544128

<400> SEQUENCE: 2
tggtgcattc tgaaaataaa cagaacaaga aatgagtttg aaattcagtt ccattaaaat      60
gcataarttt tggtttcact aaaaggggat ggaacaaatg wgaatagagc aaaatgtttc     120
ccatttggtt ctatttgcac amcaaatgct gccmaaaagt cttctttctc tatttcataa    180
caatcatcac cattttatct c                                               201

<210> SEQ ID NO 3
<211> LENGTH: 201
<212> TYPE: DNA
```

```
<213> ORGANISM: Glycine max
<220> FEATURE:
<221> NAME/KEY: variation
<222> LOCATION: (101)..(101)
<223> OTHER INFORMATION: SNP Gm16:32544169

<400> SEQUENCE: 3
aattcagttc cattaaaatg cataartttt ggtttcacta aaagggatg gaacaaatgw      60 gaatagagca aaatgtttcc catttggttc tatttgcaca mcaaatgctg ccmaaaagtc   120
ttctttctct atttcataac aatcatcacc attttatctc attttgaagt gatgcagtca   180
tgtgatttac agaaccaaaa c                                              201

<210> SEQ ID NO 4
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32545642

<400> SEQUENCE: 4
agtaaaaaaa tttaaaaata aaatctactg ctaggaaatt aaaattaaaa tagaaaacaa      60
aaacaatgtt tggaaatcaa acagattctg agtcatcacc wcatctccat ttgggatacc   120
catgtaattg agttttgcyc tctatgcaac taaggttcac tataaagata ttaaccacac   180
tctgctgacc taattaaagc t                                              201

<210> SEQ ID NO 5
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32544181

<400> SEQUENCE: 5
ttaaaatgca taartttggg tttcactaaa aggggatgga acaaatgwga atagagcaaa      60
atgtttccca tttggttcta tttgcacamc aaatgctgcc maaaagtctt ctttctctat   120
ttcataacaa tcatcaccat tttatctcat tttgaagtga tgcagtcatg tgatttacag   180
aaccaaaaca gaattaattt t                                              201

<210> SEQ ID NO 6
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32545680

<400> SEQUENCE: 6
ttaaaattaa aatagaaaac aaaaacaatg tttggaaatc aaacagattc tgagtcatca      60
ccwcatctcc atttgggata cccatgtaat tgagttttgc yctctatgca actaaggttc   120
actataaaga tattaaccac actctgctga cctaattaaa gctaacaaga cccaaacagc   180
atgakgtaga aagtcaagcc c                                              201

<210> SEQ ID NO 7
<211> LENGTH: 201
```

```
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32291307

<400> SEQUENCE: 7
taactctaat caatatttca ttcttagtca gcatgaatca ttttttyttc ttcttcttat      60
atttaagacc agaataatat atttgaatag agtgaaataa rtacatgata acgagatata     120
agattagtct aatgacgaaa agagaasaaa agaaaaagga ttaataatac taacaattaa     180
tatttgtcga taaaaaacac a                                               201

<210> SEQ ID NO 8
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32543387

<400> SEQUENCE: 8
agacaccagg tgaatatact aaagtttagc aaataatggt acggcagagt aattgaatac      60
atgaacyaaa aatyctttt tgctaattga aattgtactt ygatctcggc ctgttaataa      120
tttatgcatt tcaagggctc taataaggat tgtgtccaga ggggtgaata aaattgcatg     180
tggagtatcg cccccaaaac g                                               201

<210> SEQ ID NO 9
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32284137

<400> SEQUENCE: 9
tttcaatttg ttagaaagtt ccttaaacgg attaaagttg ggtctgaata gcactcaaca      60
tagccttccc ttaaaaattt gttaaaggat ttgtatttat yatcttatta cacaggaaat     120
aattgtcttt ctttctcctg aattacttga tataaatctt tcataaaatt attatttgtc     180
ctggtaataa acttctattt c                                               201

<210> SEQ ID NO 10
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32544094

<400> SEQUENCE: 10
atagaacagg ataaaatata acatgggtag tctttggtgc attctgaaaa taaacagaac      60
aagaaatgag tttgaaattc agttccatta aaatgcataa rttttggttt cactaaaagg     120
ggatggaaca aatgwgaata gagcaaaatg tttcccattt ggttctattt gcacamcaaa     180
tgctgccmaa aagtcttctt t                                               201

<210> SEQ ID NO 11
```

```
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32543360

<400> SEQUENCE: 11
agcacaaagt aaatgctaam ataaatcaga caccaggtga atatactaaa gtttagcaaa      60
taatggtacg gcagagtaat tgaatacatg aacyaaaaat yctttttttgc taattgaaat    120 tgtacttyga tctcggcctg ttaataattt atgcatttca agggctctaa taaggattgt    180
gtccagaggg gtgaataaaa t                                              201

<210> SEQ ID NO 12
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32546349

<400> SEQUENCE: 12
tgcagatgtc agacaaacat ggcacaccaa tgargcccaa tatcaattta gtaattaaga     60
yaataaaatc yaacaaacct aacatgaatc cctawctttg yaaggccaaa taatcagctc    120
ccttaagttt aacccataaa tccattggaa attcaactcc atcaacatgg catcacaata    180
accccaccaa atacattgca g                                              201

<210> SEQ ID NO 13
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32324276

<400> SEQUENCE: 13
tyggataaag agaaaagaaa taawggataa acacagacaa gaggatgaag aataaaattg     60
tacatacaac atcttatata tttgtgtaga tattatattc yactcatgka attaagaaa    120 tagaagtaaa aaactagcaa agtatttwrg tcacaagtgt tgtgctctcc agtccacggc    180
aaaattctct tcaytttcat                                                200

<210> SEQ ID NO 14
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32544455

<400> SEQUENCE: 14
gcaaagtcca caaacaaag gtaatgagga tctccaccac gctgcaatga acaagcattt      60
cagcataaag tggacactgc aactttttgac aactaaataa scaaagagg agaagcaggc    120 atctgtyaca aacattaaac ttacatgttt cgattctttg ctcacaagtc taacttctct    180
atayccaaca aaagggcgga a                                              201
```

```
<210> SEQ ID NO 15
<211> LENGTH: 199
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32346680

<400> SEQUENCE: 15
aagctyygaa acactatatt ttttttttc atccttaatc aygyataact ttcttttaaa      60
ttgtatctca ctccttaaag acactaaatt ttcacgcacr atggaatgtt aattgtgttt    120
cttttgaatg aattgaagaa ggacaccaac ccttttgata ctataattgt gtycaaatgt    180
cttaaaaagg aagatgcat                                                  199

<210> SEQ ID NO 16
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32543724

<400> SEQUENCE: 16
attgagttca tcaactttat aacctgcaca ccaccccaac aatgtcagaa acaccaaga      60 agtttggata gtaaatrtgt gtaaaatcgt caaacataar aaactgttag gtttgccaac   120
cacgggagca cagctgacca caataagcat acacatagca atgcattata gtttattgaa   180
cacttatttt tggttcttgt                                                200

<210> SEQ ID NO 17
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32546343

<400> SEQUENCE: 17
cacatatgca gatgtcagac aaacatggca caccaatgar gcccaatatc aatttagtaa     60
ttaagayaat aaaatcyaac aaacctaaca tgaatcccta wctttgyaag gccaaataat   120
cagctcccct aagtttaacc cataaatcca ttggaaattc aactccatca acatggcatc   180
acaataaccc caccaaatac a                                              201

<210> SEQ ID NO 18
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32543241

<400> SEQUENCE: 18
ctattttaag caattggaat aataacytgt tagatatccc atatacatac ccaagtgtgg     60
tagtatgata atattggata atmaaaaaat agtaatagaa waatgatagt tctttgggca   120
gcacaaagta aatgctaama taaatcagac accaggtgaa tatactaaag tttagcaaat   180
aatggtacgg cagagtaatt g                                              201
```

<210> SEQ ID NO 19
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32542545

<400> SEQUENCE: 19

```
cttataatat aacttttttt actatctatt caatgcaatt tttgttttta ttgtctgttt      60
tatgctcttc attgtattgt atggtgattc taaagaaatg raaaataaca tttaaacaac     120
tyattattag ggatagaatg atcttatttt gtccatgcat acatcttcaa acttcatgca     180
atttactgtt ttatcttaaa g                                               201
```

<210> SEQ ID NO 20
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32286588

<400> SEQUENCE: 20

```
tcataattat aacaatttat gtaacasaac raaattatar ttttgttagt ttaccaaaaa      60
ggatgggtgm gtgccaatat gggaggaaag aagcaaaatg rcttgtattt atgcatttca     120
tgctagggac caaaagcaat tttggaggag tcaatatcaa ttccgttatt attatttgaa     180
atgaaggtaa tataagatat a                                               201
```

<210> SEQ ID NO 21
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32546309

<400> SEQUENCE: 21

```
aaaatcttga aaacaccagg aaattgaata aggccacata tgcagatgtc agacaaacat      60
ggcacaccaa tgargcccaa tatcaattta gtaattaaga yaataaaatc yaacaaacct     120
aacatgaatc cctawctttg yaaggccaaa taatcagctc ccttaagttt aacccataaa     180
tccattggaa attcaactcc a                                               201
```

<210> SEQ ID NO 22
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32282532

<400> SEQUENCE: 22

```
atatctaaaa ttttgatcra aatccaaatt aaattactac ccaaattaat tttgatttaa      60
aatttactca aattaattaa ttaattaatc tacaaactta wgatatggac cctaaaacac     120
ctgtcctagg cccaggatcc aacaaactac aaatactttg acccaagggg aagaaaaaa     180
ttgactcaaa aagagggtta a                                               201
```

<210> SEQ ID NO 23
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32540234

<400> SEQUENCE: 23
acaaaatatg gcagttttaa attgcactca agtcaatatt tgtctactat taatagttat      60
gtaatttkta tttattgaat ttaattaaaa tgcacttata ktataaagat ttattataat     120
catctcatca tgtattatct cctatagctt ttctaataat tacattagaa aaacatatat     180
gaagttattt ctaatagaat g                                                201

<210> SEQ ID NO 24
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32346259

<400> SEQUENCE: 24
tttgggaaag tttggtttga accctaactt ggtaaatttg ggaattttat ttgggttgca      60
tgatttatga gttattagat gtttgtttgg tgtattaatg yttgatggac cattcatgtg     120
tcttttatga tgtttagaac tggttgggaa gtcattaatg gcctwgaaat ttctaaaatt     180
gaaactccct acattttrcc c                                                201

<210> SEQ ID NO 25
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32546697

<400> SEQUENCE: 25
agaactagta aaatggaatt caaaatggaa ctaattcaat gagaaaaaat tgattacatt      60
aaaccatcta ggtggctgtt atatacaata tgagaagtaa staacttgca aataaatttg     120
taactaacta tacctttaat ataaggttca ttttatttga caaattcttt ttccaaatga     180
gattatcatg caacctaagt t                                                201

<210> SEQ ID NO 26
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32286461

<400> SEQUENCE: 26
caatagaatc ataggtgata tacaataaaa wtatgatttt gtwgtattct ttttataccc      60
tcacagcmga ataacataca atgaaatttg tgattctgtt scagggtgaa tttgtaatac     120
aaaagaatca taattataac aatttatgta acasaacraa attatartttt tgttagttta    180 ccaaaaagga tgggtgmgtg c                                              201

<210> SEQ ID NO 27
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32542834

<400> SEQUENCE: 27
aacattaaaa aaaaahatgt tgacattaca tyaaagataa ttaagcatgt taagtyccaa      60
catatttaaa ttctraagtt atcaattgca tttaatcttr ttatttacc tgtcttttat     120 tctttctttc tttcatttca atttcttatc tcttgcttac aaattagata tatatcaact    180
caaatataaa aagtccttgt                                                200

<210> SEQ ID NO 28
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32346754

<400> SEQUENCE: 28
cttaaagaca ctaaattttc acgcacratg gaatgttaat tgtgtttctt ttgaatgaat     60
tgaagaagga caccaaccct tttgatacta taattgtgty caaatgtctt aaaaaggaag   120
atgcatgcaa taagatttga gatgcyttct ttggatgaty ggtgrggttc tgycacttct   180
catcccaaaa aatgtggtaa                                               200

<210> SEQ ID NO 29
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32286518

<400> SEQUENCE: 29
ccctcacagc mgaataacat acaatgaaat ttgtgattct gttscagggt gaatttgtaa     60
tacaaaagaa tcataattat aacaatttat gtaacasaac raaattatar ttttgttagt   120
ttaccaaaaa ggatgggtgm gtgccaatat gggaggaaag aagcaaaatg rcttgtattt   180
atgcatttca tgctagggac c                                             201

<210> SEQ ID NO 30
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32542809

<400> SEQUENCE: 30
aatagatgtg aatgaaaatt aaaacaaacat taaaaaaaaa hatgttgaca ttacatyaaa    60
gataattaag catgttaagt yccaacatat ttaaattctr aagttatcaa ttgcatttaa   120
tcttrttatt ttacctgtct tttattcttt cttttctttca tttcaatttc ttatctcttg   180
cttacaaatt agatatatat                                                       200

<210> SEQ ID NO 31
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32545807

<400> SEQUENCE: 31
agatattaac cacactctgc tgacctaatt aaagctaaca agacccaaac agcatgakgt            60
agaaagtcaa gcccaaaaat aaatacaagc cacaataaaa magaaacact gtaaaggcag          120
catggaattc caggagcaga atctcttatt gttgctgtca ctcagtcatt gttgcatcta          180
tytgaaaatt acagcttaga a                                                    201

<210> SEQ ID NO 32
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32239934

<400> SEQUENCE: 32
ggttctagtc ttccgggaaa aaaaatgtgg gaatggggag gtgagatggr aagaacttttt          60 cgtacaatwa aatttctcta aggaatacaa ccagtaacaa wttttcattt ttctctcttt         120
gataggttgt gtcaaggttt gtgtttgtgc cactggctca ctttgtattt agcataagaa         180
aagtggaaac ggtaaaaact                                                     200

<210> SEQ ID NO 33
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32544481

<400> SEQUENCE: 33
aggatctcca ccacgctgca atgaacaagc atttcagcat aaagtggaca ctgcaacttt          60
tgacaactaa ataascaaaa gaggagaagc aggcatctgt ycaaaacatt aaacttacat         120
gtttcgattc tttgctcaca agtctaactt ctctataycc aacaaaaggg cggaaaatat         180
ctaaggtgag gttaaggaat a                                                   201

<210> SEQ ID NO 34
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32346987

<400> SEQUENCE: 34
aaggtcatgr tatgagaaca agggggggaya ctacttggaa gtttaagttc aatacttgtc         60
ataggacaaa aaagacaaag aaagaaatka tgttaagcat rcaaaacttg atgtctaast        120 ttatgttat gcttttgyca atgttgaagt gaagctacmt gtaaggatgt tcacgagtat    180
gagccactmr aattgaccca a                                              201

<210> SEQ ID NO 35
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32347808

<400> SEQUENCE: 35
tgttgcttcc atggatttta taagtatatg gggtcatgtc tagcacttkc ttagaccgtg    60
tcccattagt ttagatttca tgttctagat tgagtagatt wtggagaatg aagactctgg   120
tcatgcagat gytatgtttt tgtgaattaa tgtctttggc ttattacttt ttagacactt   180
agttatgtaa ttattctttt a                                             201

<210> SEQ ID NO 36
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32540201

<400> SEQUENCE: 36
ttgtcactag ttgttatgta ttaaataaac tctacaaaat atggcagttt taaattgcac    60
tcaagtcaat atttgtctac tattaatagt tatgtaattt ktatttattg aatttaatta   120
aaatgcactt ataktataaa gattattat aatcatctca tcatgtatta tctcctatag    180
cttttctaat aattacatta g                                             201

<210> SEQ ID NO 37
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32546282

<400> SEQUENCE: 37
caatccatca cattatattc aacccataaa atcttgaaaa caccaggaaa ttgaataagg    60
ccacatatgc agatgtcaga caaacatggc acaccaatga rgcccaatat caatttagta   120
attaagayaa taaatcyaa caaacctaac atgaatccct awctttgyaa ggccaaataa    180
tcagctccct taagtttaac c                                             201

<210> SEQ ID NO 38
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32286403

<400> SEQUENCE: 38
tgtttataca tcattacatt cataatcttc ktggtatggg aatgcgaaaa atgttataca    60
atagaatcat aggtgatata caataaaawt atgattttgt wgtattcttt ttatacctc   120

```
acagcmgaat aacatacaat gaaatttgtg attctgttsc agggtgaatt tgtaatacaa    180
aagaatcata attataacaa t                                              201

<210> SEQ ID NO 39
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32545360

<400> SEQUENCE: 39
attattagta gagttattag tacwttccag gttaattaaa ttttcatttc cataaacaat    60
aacaaaatac tttwaaagaa taggaaatta aggctgttca yggttcatgt attttctgtt   120
tttattgggg raaaaaacac atttgaaaaw gtgctcagtg arttttaata ataatatcag   180
atgaaaaaaa aatatgtttc                                               200

<210> SEQ ID NO 40
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32285402

<400> SEQUENCE: 40
ctcaattggc mtgtgtgcta gagatttctg ttaaacagtc agttttcaat tatctttgta    60
gcatgagaga atcatggtat gcacataaac gattagctgc wgtgtggagc tgacattata   120
tattagtggc tccataaaaa gtgtttcatg attcctgatt ttatgtcttc ttcatgtttt   180
acttttagtt ccaatagaag a                                             201

<210> SEQ ID NO 41
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32544988

<400> SEQUENCE: 41
ataatccacc accaccaccc ctagccaacc caagaccacc aactgyactg ayttccccag    60
aagtaaatga agaaagttgc tgcataaata aacaggatgc rtgttttcaa aatcaagcag   120
tgaaaatgaa agtgcccaaa ataaccaaca gtgaaatatt taagacataa gaagatgaag   180
tgttacccca ctctgaaggt a                                             201

<210> SEQ ID NO 42
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32286428

<400> SEQUENCE: 42
tcttcktggt atgggaatgc gaaaaatgtt atacaataga atcataggtg atatacaata    60
```
aaawtatgat tttgtwgtat tcttttttata ccctcacagc mgaataacat acaatgaaat     120
ttgtgattct gttscagggt gaatttgtaa tacaaaagaa tcataattat aacaatttat     180
gtaacasaac raaattatar t                                                201

<210> SEQ ID NO 43
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32283215

<400> SEQUENCE: 43
aattgagtct ttggtggttc caaattttgc gctttggaag aaagttgttt tttgttgctg      60
aatggaaatt tgagtgtttt gaactataat ttagaataag yaggtttggg atgaggaatg     120
ataagtatga gttgtttatt tttttgcaa aatataagta caacttgtta gttatttttc     180
ttcactgcta ttaactgatg t                                                201

<210> SEQ ID NO 44
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32454541

<400> SEQUENCE: 44
agattaaatt tcttatgtat cgacgagcrc atctgttgca tttgttttat catcttgata      60
taggtcttct tgtattagra agactttgt ttttaactgy sgggtatgcc ccgtttatta     120
ttgtatcrtt ttgrgtttaa tatcatttac rtttttctcca aaacatgtta gttttttgtgc     180 ccattctacc ttaagcgcta                                                  200

<210> SEQ ID NO 45
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32297214

<400> SEQUENCE: 45
ctcacattgc tagaatccct gagtttctgt aaggttggtc agaatttgaa atgccgaaag      60
tggcctatat gggttgttgg cagtgaatcc cattacacas tactgttctg gacaccagtg     120
ttcaaaatga gaatgagctg gaacaaaggg aatcrcagat tcgcaaagct ttygatgctc     180
aatatcagag cggcgggggt                                                  200

<210> SEQ ID NO 46
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32340207

<400> SEQUENCE: 46
tatttaggca aaaaaatagt gttctgtaag atgatgacct tgtcaatgat taaacctgtg      60

```
actgctatat cacaaataca ttataggctt cattttgatt wtgaaaagat aagcatgaaa    120
tgtctcttga tgcattggtt ccagtcatat gagaagtaat aactgataat tcaatgctgg    180
gtttgtaaat tgaactgagt a                                              201
```

<210> SEQ ID NO 47
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32273397

<400> SEQUENCE: 47

```
ttctctcccc caaggctttc ttaattccaa ccctctcctt tggctaaagc atagcttta     60 gctccaaggg ggattctcta tgttgtagca ttatgatgga wttggaagtg gcgcaacaac    120
aaattttttt atgtggacaa gtgggttrct caacaagtca tttgttggat ttatgctttg    180
cacaatgata ttgttttggc t                                              201
```

<210> SEQ ID NO 48
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32284255

<400> SEQUENCE: 48

```
ataattgtct ttctttctcc tgaattactt gatataaatc tttcataaaa ttattatttg    60
tcctggtaat aaacttctat ttcgaatgaa agtgatcata yatggaaaat atgcattgct    120
ttatatttag gttgcctaag taaaacttttt gtaaggggaa aattctttta gaattttttgt  180 atctgcttcc tttcctgtct c                                              201
```

<210> SEQ ID NO 49
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32296634

<400> SEQUENCE: 49

```
acataaacat aaattttata acagttacat aattatacta ttcataatat ccctaattac    60
aaataaattg ggagatttct aatgttaagc ttgttgactt yagagtgagc taaatcttga    120
atttgtgtcc atttcttgac ctcttaaatt ttaagctaat gacaatcgaa tgccttgttt    180
tgtcccaaga tgtgtatagc                                                200
```

<210> SEQ ID NO 50
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32297269

<400> SEQUENCE: 50

```
cgaaagtggc ctatatgggt tgttggcagt gaatcccatt acacastact gttctggaca      60
ccagtgttca aaatgagaat gagctggaac aaagggaatc rcagattcgc aaagctttyg     120
atgctcaata tcagagcggc gggggtggtt cgttagtgta aagggctcc atcaagttca      180 tagagaaaca matatcaaac                                                  200
```

<210> SEQ ID NO 51
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32543353

<400> SEQUENCE: 51

```
tttgggcagc acaaagtaaa tgctaaamata aatcagacac caggtgaata tactaaagtt     60
tagcaaataa tggtacggca gagtaattga atacatgaac yaaaaatyct tttttgctaa     120
ttgaaattgt acttygatct cggcctgtta ataatttatg catttcaagg gctctaataa     180
ggattgtgtc cagagggtg a                                                 201
```

<210> SEQ ID NO 52
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32287149

<400> SEQUENCE: 52

```
atgggagatc gctcgtgcaa cttcgttgga actaaatcaa gtgcctgata acagagaaga     60
tttatcaatt tgattcacaa atgatgcttt tgaaactata scagcatgta tgsgtgattc     120
caatttcaag tggaaagaaa aataagagaa aaattgtcag tgtcagttaa aagaaatgta     180 aattaccgt tccttgcccg t                                                 201
```

<210> SEQ ID NO 53
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32278942

<400> SEQUENCE: 53

```
atgattttg cagacaaaag gttagtatcc ttgagtcctt ttgcttccat gaacaygttg      60
aacatttggg aaaatgtgag ggttgcttat agtattctac rctgacgtta atttgatgaa     120
gscaacttgc tagtttctag ttttgattca aaaagcacaa tgcactcttc tctttgtaac     180
tttatggaat ttgtcctgaa a                                                201
```

<210> SEQ ID NO 54
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32297835

<400> SEQUENCE: 54

```
ttggtatgta agttttaaat ttgwtggttc tgaattgttg tgatgctaat actaaattta        60
ttgtgctctg gttctcaaaa gggaaaattg aatattaatc rtatcaccac cccatctaac       120
ctggaacatg atcgatttat caattgctaa tgayaatcat cataaaacag ggtccgtatg       180
gttgtcaaaa caaaaaaata                                                  200
```

<210> SEQ ID NO 55
<211> LENGTH: 199
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32552252

<400> SEQUENCE: 55

```
gttaggaata aaatatatta accgagcaaa aaaatcattt agaattttct taacaaagta        60
ttatatgact gccttttatt tttattcctt attacatgtm cttggatwat ttattcataa       120 aatccttta tatcaacagt ttttagtagt aycattatca tgtgtgraca ttaagaggtc       180
tagcatgatc agycttaat                                                  199
```

<210> SEQ ID NO 56
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32297287

<400> SEQUENCE: 56

```
gttgttggca gtgaatccca ttacacasta ctgttctgga caccagtgtt caaaatgaga        60
atgagctgga acaaagggaa tcrcagattc gcaaagcttt ygatgctcaa tatcagagcg       120 gcggggtgg ttcgttagtg tagaagggct ccatcaagtt catagagaaa camatatcaa       180
acttccacaa gagaagcttg                                                 200
```

<210> SEQ ID NO 57
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32570539

<400> SEQUENCE: 57

```
aaacaaaaac aagaaaacaa aaayaaaaac ttgcagacat cgaaattaat ctgataataa        60
ttgcaaaata gtatcgcatg tatcaatgca ttttatatgg ycgttattgg agaacttaaa       120
tccaaatttg gaagacttat atgtcaaggg aagctaattt aattggctga ataaaagtgg       180
agaaattatt ataaattcct t                                               201
```

<210> SEQ ID NO 58
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32459125

```
<400> SEQUENCE: 58
tctttgacga ctttagatct atcgggaaac cagttcacag ggctgccagt gcatctaagt      60
acaatctcat catattcctt ggggattcta tatttgtcct wcaataagct gcagggaaac     120
attccagaat caattttcag ccttgtaaac cttactctct tagatctatc atcaaataat    180
ttcagtgggt ctgtccactw t                                              201

<210> SEQ ID NO 59
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32296468

<400> SEQUENCE: 59
atccacacta agattattgg aaattgcaac aacactgaga tcttgaggtc ttccattcag      60
ttcaggttgt ttggattgaa aatactaaac ctgatacca maccgaacaa ggcagggttg     120
actttgtgga aatcgtacgg aaccatcaac ccaaaccaac ccacatacat aaacataaat    180
tttataacag ttacataatt a                                              201

<210> SEQ ID NO 60
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32109926

<400> SEQUENCE: 60
aaaagacact acaagaaagy gaagatgtca gagaagcaat ggtcaaaaga gaaagaaaag      60
agattarata tgttatggat aatagtgaag gtgaaaagtg maaaaggatg cagatggaag    120
caaagaaaga cttgrcaaaa gagacaacac aagaaggtaa agatttgaaa gaagcaatgg    180
tcaaaagaga aggcaaagag a                                              201

<210> SEQ ID NO 61
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32562910

<400> SEQUENCE: 61
tccttaaatt tttaacatcc catcttatcc ttcttccttc tcccatcrct caccctcttt      60
ttctctccat cttgctcttc ctatctcccc ccattccttg matcctgcca caacttcttc    120
cacttccktc atcgctcatc ctccttctgt cactctccat gaatgttgtt ttccaaattt    180
cctattttgt aattttttt                                                 200

<210> SEQ ID NO 62
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32339979
```

<400> SEQUENCE: 62

```
ttttatattc tttatggtta catgtcaaag aaaagaagaa ggttgtttct ttaattttat    60
aaaacatgga ggtggtttgc agaaatttac tgttgcattt kctcttatga cacaaatctc   120
ttatctgata aaggaccaaa taaccagaga gtagacctca acactggata gccattgctt   180
gatatatatc tttgaatgtc r                                             201
```

<210> SEQ ID NO 63
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32296941

<400> SEQUENCE: 63

```
tacaatagcc acttaagtgt catcaatgca aaagcatgcc tctcaggtat ataccaacag    60
aatgtaaraa tattgctatc atttcaagtg cttcacattt waaaatctgc cagagcatgt   120
ctgagttttt tcttcctgct ggatattttg ttgctggata ttgtaaactt gctgctctgt   180
gggcaggccg tctctaatgt c                                             201
```

<210> SEQ ID NO 64
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32464136

<400> SEQUENCE: 64

```
aatgtaattg atttataaa attgattttg aagtgattta tgttggtatg ttttattata    60
aaattactgg aagtgacaaa gatgagaccg ataccgaagg rtgaagacca aagatggcca   120
tatgcactac ttagtataat ggttggtgta atagcaactt ccacgaatat gtgcaattgt   180
gcatgtttgg ttttaagatt a                                             201
```

<210> SEQ ID NO 65
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32298201

<400> SEQUENCE: 65

```
gaaaagaaga accaagttct gggagaaatt tcggcaataa gatgcaaaga atagattgat    60
cttgaattat taaattttca ttaaccactt ttcctaagag wgcttatgta aaattaaaga   120
atttgtctga gtatgcccat gccttgcygt tgacaatggc atagttgcgt tccaatgaga   180
agctattgaa atgtttaatg a                                             201
```

<210> SEQ ID NO 66
<211> LENGTH: 199
<212> TYPE: DNA
<213> ORGANISM: Glycine max
<220> FEATURE:
<221> NAME/KEY: variation
<222> LOCATION: (100)..(100)

<223> OTHER INFORMATION: SNP Gm16:32300241

<400> SEQUENCE: 66

```
ggataaaaat atttcttcat agtggtaaat gagaaccgag agaagaaaaa taatgaacgc      60
atacctttta ttaaccttct tgtttwtttgt aaaatcgtgw gaactcagcg ttaaaatata    120
aatgaagaaa aagaaaaaag ggatataaac tatgaaggaa acaaattgtg ggaaataaaa    180
cagaagcatc ctactagat                                                  199
```

<210> SEQ ID NO 67
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32271645

<400> SEQUENCE: 67

```
aaagattgaa actttktctc aaaatcaagy tgagaaccct gaaacaaaga caaacaacta      60
aaaagaacac atcctcagtc accaaggagt gaagaagtgy sgtaagaaaa caagggaaaa    120
agagaagaaa aagagcgaaa tcactaaaga caaggattag tttgtgatgw gaactagtta    180
ctatgtaacs aggctatata t                                               201
```

<210> SEQ ID NO 68
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32271574

<400> SEQUENCE: 68

```
aggctcaccg gcgaagaagc tcaacaactt ctctgatcaa aatcttcaca aaatctgaca      60
cccttagaag caaagattga actttktctc aaaatcaagy tgagaaccct gaaacaaag     120 acaaacaact aaaaagaaca catcctcagt caccaaggag tgaagaagtg ysgtaagaaa    180
acaagggaaa aagagaagaa a                                               201
```

<210> SEQ ID NO 69
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32346412

<400> SEQUENCE: 69

```
attaatggcc twgaaatttc taaaattgaa actccctaca ttttrcccaa aaattaagct      60
ctacactaag cytgggattt gtgaggctta gcttaagaag macaaattga agatttagct    120
ctagggactt aaggctaagc gwgaaatttt ctcaatctta gcatggrctt crrgctaagt    180
gtagaacttc tcaagctaag t                                               201
```

<210> SEQ ID NO 70
<211> LENGTH: 200
<212> TYPE: DNA
<213> ORGANISM: Glycine max
<220> FEATURE:
<221> NAME/KEY: variation

```
<222> LOCATION: (101)..(101)
<223> OTHER INFORMATION: SNP Gm16:32339865

<400> SEQUENCE: 70
atagaattgt ccttggtttg wcaaaagtta gattaaatta ctctctatct cattcctwgc      60
attttgttca tattacagaa ggcccttttga aaattatacc ytcctcatct gtttttata     120 ttctttatgg ttacatgtca aagaaaagaa gaaggttgtt tctttaattt tataaaacat    180
ggaggtggtt tgcagaaatt                                                 200

<210> SEQ ID NO 71
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32275584

<400> SEQUENCE: 71
atcttttata agtttaagtg tgtatttgat tatgggttgg gaatgtttag atgcacatca      60
ttatcatttt tggacaaaat aagtagcttt cacgtagtga kgggtgytta cggttaagtt    120
tggatattta gtgtgatgat tgagaagttc aattttggtc agttttggaa gttccctact    180
gttgaatgtt tgattttgtt                                                 200

<210> SEQ ID NO 72
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32287898

<400> SEQUENCE: 72
ttatcagttt aacaattgca tctgtggatt atatcacata tctatttatc tcctattta      60 tcagtcatcc tttattctct ggtaaatttt aattcagcaa ytgcatcctt tatgtatgct    120
ccggtaaatt tcaaccagaa aataagtcca ccgttcagag taaattaata tgattcagat    180
tcaagaagct gaaaccagaa a                                               201

<210> SEQ ID NO 73
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32455251

<400> SEQUENCE: 73
attaaaaaga accaatagaa acaaaagtaa gagaaataaa agtcaacaac agcctaggta     60
cctctccaaa tacttgcaag cttaataaaa taatgaaaat mtaataaaaa aaatggagga   120
aatagccaac acaccttcta tatatgacca tgcattgtta catctctacc acaaaatatg   180
aatatctaat cttattggaa a                                              201

<210> SEQ ID NO 74
<211> LENGTH: 201
<212> TYPE: DNA
<213> ORGANISM: Glycine max
<220> FEATURE:
```

```
<221> NAME/KEY: variation
<222> LOCATION: (101)..(101)
<223> OTHER INFORMATION: SNP Gm16:32346356

<400> SEQUENCE: 74
atgyttgatg gaccattcat gtgtcttta tgatgtttag aactggttgg gaagtcatta       60
atggcctwga aatttctaaa attgaaactc cctacatttt rcccaaaaat taagctctac    120
actaagcytg ggatttgtga ggcttagctt aagaagmaca aattgaagat ttagctctag    180
ggacttaagg ctaagcgwga a                                              201

<210> SEQ ID NO 75
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32570462

<400> SEQUENCE: 75
gtgaagtcat tcctacgtag ttatacttat atgtagctag ttccaaataa ggtcaataaa     60
aatttggatg ttagtaaaaa caaaacaag aaaacaaaaa yaaaaacttg cagacatcga   120
aattaatctg ataataattg caaaatagta tcgcatgtat caatgcattt tatatggycg   180
ttattggaga acttaaatcc a                                              201

<210> SEQ ID NO 76
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32665882

<400> SEQUENCE: 76
aaaaaaaaac aaccttggay cacgtaaaag ttgtaaccca aaagaaaat agttggacat     60 agcccaaaac gacgacgttg cgattcatca cttgtgaaca sccccatttc cccaccgcaa    120
agtctcattc tgcaaawtgg aggccrgtgt ctcatcctct ctyggystya tgagggaaga   180
tcgaattagc tggttttgag g                                              201

<210> SEQ ID NO 77
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32563711

<400> SEQUENCE: 77
attgtcttaa ttgtttccrk gggattcagg aagcaatagc cttaacttgt tcttgaagag    60
tcyaaaaart atattacaaa gaaattgggc tttgctttgc wattgggctg aaagagggtc   120
ttttcgatcg aarcactaat aatgaggcat tcagaaggar ctgaagacaa ctagaatatt   180
attagaattt twgtcaatag c                                              201

<210> SEQ ID NO 78
<211> LENGTH: 200
<212> TYPE: DNA
<213> ORGANISM: Glycine max
```

```
<220> FEATURE:
<221> NAME/KEY: variation
<222> LOCATION: (100)..(100)
<223> OTHER INFORMATION: SNP Gm16:32267736

<400> SEQUENCE: 78
aaaaaaaaaa caawtgttta aaaataagc  acataaaagt aaatgcaact cctcctaagc     60
tagactattg tggcattgtg tttsctacac tttgttggay gaagcttaac tccaacaata   120
tttttgggat atctattcaa ttaagccatt gccttggcct tagcttaagg gtttggcttc   180
catatggtgc aaagcacatg                                                200

<210> SEQ ID NO 79
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32269647

<400> SEQUENCE: 79
aatcaataaa tctctatcca tcatccactr gatttttcaa cttctcaaat ctgaatagcg     60 ctaggggggtt tcattctttc ataagttttc ccataaaaat ktatactttc aactacataa   120
acacaactta tcaaacatag ttggaaaaaa agggccattg tgcatcaaat gcytttgaaa   180
aaaaaaaagt aatacracca                                                200

<210> SEQ ID NO 80
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32525289

<400> SEQUENCE: 80
aaaatttata sgtttaatta tgaaatgacg aatatacaac ataaaaaaac aaaaaaaata     60
gcctgtacta tgaacactac aagaatttca ctcaatagtr agggaaatta gagagatttt   120
ttttcactaa tcgctcaaaa attagcgata ggtttatgag aaacacactt tatttcacat   180
tccatttcat ataattttg                                                 200

<210> SEQ ID NO 81
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32211313

<400> SEQUENCE: 81
atgctttgat aaggataagg acaagtctag aaaccaagta tcaagagaat ggaccaaaag     60
ctccattgtg ggaagatatc tcaattgcaa tgcaaaggct wgggtacaac cggagtgcaa   120
agagatgcaa ggaaaaatgg gagaacatca acaagtactt caagagagtg agggagagta   180
gcaaagaaag gcgtgaagat a                                              201

<210> SEQ ID NO 82
<211> LENGTH: 201
<212> TYPE: DNA
```

```
<213> ORGANISM: Glycine max
<220> FEATURE:
<221> NAME/KEY: variation
<222> LOCATION: (101)..(101)
<223> OTHER INFORMATION: SNP Gm16:32347756

<400> SEQUENCE: 82
ccaaatctaa ctcaacctcg cttgtgaact cccctagcta gctatatgtt tatgttgctt    60
ccatggattt tataagtata tggggtcatg tctagcactt kcttagaccg tgtcccatta   120
gtttagattt catgttctag attgagtaga ttwtggagaa tgaagactct ggtcatgcag   180
atgytatgtt tttgtgaatt a                                             201

<210> SEQ ID NO 83
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32271714

<400> SEQUENCE: 83
catcctcagt caccaaggag tgaagaagtg ysgtaagaaa acaagggaaa aagagaagaa    60
aaagagcgaa atcactaaag acaaggatta gtttgtgatg wgaactagtt actatgtaac   120
saggctatat ataggatact aaggaaaata wcgaaagaac cttaatggtt caatgtatga   180
tgaaattagt gtagaccaac c                                             201

<210> SEQ ID NO 84
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32550454

<400> SEQUENCE: 84
accttcgcgg agtgagtaac cgaaacgacg ccgagcarcg acaaaacggc gtcgtttakc    60
tcctctccgc cgtcctttaa aaaactcgmr agcaacgaca rcaatccgca tgcttcgctg   120
atcgatttgg aagattgaaa atcgmacgcg agaaactcca aaaccttaac mgtttcaatc   180
tttgatttca gagatccgtt t                                             201

<210> SEQ ID NO 85
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32550524

<400> SEQUENCE: 85
cgtcctttaa aaaactcgmr agcaacgaca rcaatccgca tgcttcgctg atcgatttgg    60
aagattgaaa atcgmacgcg agaaactcca aaaccttaac mgtttcaatc tttgatttca   120
gagatccgtt tctgagaaca aatatcatcg catcwaagca ttgttcscga gcgtcaagaa   180
tcagctttcg aattctctct c                                             201

<210> SEQ ID NO 86
<211> LENGTH: 199
```

```
<212> TYPE: DNA
<213> ORGANISM: Glycine max
<220> FEATURE:
<221> NAME/KEY: variation
<222> LOCATION: (99)..(99)
<223> OTHER INFORMATION: SNP Gm16:32517555

<400> SEQUENCE: 86
aggaaagaaa gacaaaggtt aaaaaaagta taagataaat gtaaaattta gaataaaaaa      60
aaytaattag gattcttatt agatcttctt agcagaacra tatttaagta tcgatttata     120
agtctcactt tgactttsta tatgctattt ttacacttct acaaagagg gaggaagaga     180 aaaaacaaaa tgtgagttt                                                  199

<210> SEQ ID NO 87
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32464778

<400> SEQUENCE: 87
ctagttgttc ggtaatttgc actcttacga tggtgggtta ttattgtaca aatttctgaa      60
accaattaat agaaactcgg gcttaaccat atgtgccggt saatayataa catccatttm     120
tttaattgat taagaaatca ttgacataaa cacgatatgg ctaggaacct tcaatatgca     180
tgacgcaatg tatgacaggg a                                               201

<210> SEQ ID NO 88
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32315350

<400> SEQUENCE: 88
caccatttct accagaattc atacaattca ttaacaaatg tttctcatac caagcatgca      60
tgatttcata aattttaaga aactaaacga tttagagttt rgaaattacg atattacatg     120
tgttcaaata taactgcatt acctgaagtg aaacaaccac taataaagaa ataaagtaat     180
tatatatgag ataagatatt c                                               201

<210> SEQ ID NO 89
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32263188

<400> SEQUENCE: 89
tttttgtacc aatgtgctac aaaacaatgt gattgtatgc cactggttaa acccaataat      60
atgttcccag acagattaag ataatctgat acaacaacct mcaatatcaa ttgataaatt     120
tccttataag aacaataaag gattttagtt ttcgtgcaag gtagaagaac attgcagttg     180
ctgtcaaaca tgaagaggaa r                                               201

<210> SEQ ID NO 90
```

```
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32550442

<400> SEQUENCE: 90
ctaacgagtt ccaccttcgc ggagtgagta accgaaacga cgccgagcar cgacaaaacg      60
gcgtcgttta kctcctctcc gccgtccttt aaaaaactcg mragcaacga carcaatccg     120
catgcttcgc tgatcgattt ggaagattga aaatcgmacg cgagaaactc caaaaccttta    180 acmgtttcaa tctttgattt c                                              201

<210> SEQ ID NO 91
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32217702

<400> SEQUENCE: 91
ttctcccaar cctccatgac caacattgca ccttcatgtc rcaccaccat gacccacgaa      60
accctcctgc atcatcaatc caccaytgcc ttacatcaty cacaaatkta ttatgaattg     120
aataatccgt aayatattta tattacawat kgyttaattc gtaataaaca aaatgattta    180
tractttcty actcttcatt                                                200

<210> SEQ ID NO 92
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32225387

<400> SEQUENCE: 92
gatgtttctt tgcttmcatt tgtgtggttg taataagata ttttgatggt atatgaaaaa      60
cacaggaaag caataagagc tagctagggt ctttggaagt scaaattaag ctcagatttg     120
agagcatcag catggcatgg accatcgaca gcatcaatat tctgttctgc tctgcttcaa    180
tcgcacccac tttttcagat g                                              201

<210> SEQ ID NO 93
<211> LENGTH: 199
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32552305

<400> SEQUENCE: 93
acaaagtatt atatgactgc cttttatttt tattccttat tacatgtmct tggatwattt      60
attcataaaa tcctttata tcaacagttt ttagtagtay cattatcatg tgtgracatt     120
aagaggtcta gcatgatcag ycttaattag aaaaaatcct tatgcttcat tacctcaaaa    180
aagcttgaac aacaaagaa                                                199
```

```
<210> SEQ ID NO 94
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32344193

<400> SEQUENCE: 94
ctagcttaat ttccagaagc ttatgaccag cttcctcyaa atcaacacta gacataattg      60
ctgagtattt tgtctttcga agattgacaa gatttgtctc matttcatct tttatctgca     120
tatgttcttc ttcctcttyg ttgycattgt ctgactcatc agcatccaag ccttcctcat     180
catcatcctc agattcctca c                                              201

<210> SEQ ID NO 95
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32349746

<400> SEQUENCE: 95
tgaggaaccc taatgcacat ttttcaaaam aaaaaaaaaa ttaagtctag ggaaattatt      60
attgcttkaa atttgtgaag ttgcagattt tttcatttgm gtgtttcaaa tttaacgcat     120
gaatataaac atggctacaa tatgtaattg cagaggtcrg taaggcgcaa cgggaagaat     180
taaagcgcct tagggcaaga                                                200

<210> SEQ ID NO 96
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32550443

<400> SEQUENCE: 96
taacgagttc caccttcgcg gagtgagtaa ccgaaacgac gccgagcarc gacaaaacgg      60
cgtcgtttak ctcctctccg ccgtccttta aaaaactcgm ragcaacgac arcaatccgc     120
atgcttcgct gatcgatttg gaagattgaa aatcgmacgc gagaaactcc aaaaccttaa     180
cmgtttcaat ctttgatttc a                                              201

<210> SEQ ID NO 97
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32271035

<400> SEQUENCE: 97
agacctttgg caatgatgaa tatgttgttg gttcatggaa tgaggatgct tctcttttyg      60
acgaactcgc attgatctag gcaaatcaga accaccaaaa ygaccsctac cttgaagcat     120
acctctcttt gacaacttgc cttccattgc ttctcacaat caacaaaaac atatcaaacc     180
aatgaaccca tttcacatcc a                                              201
```

<210> SEQ ID NO 98
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32342403

<400> SEQUENCE: 98
gatcaaaacc tttcttttt aatcatttag catgatgaga atgtcaacgt tgattttaa      60 gattttcatt taaaaccact gtttagggaa acaaaattat rtaaaatgca taaattgatt  120
taattagttt ggtgctattt caaaatacaa gtacactgaa ccgaaatgtc aggctaatgg  180
ggcctatggg ctatgggcag t                                              201

<210> SEQ ID NO 99
<211> LENGTH: 199
<212> TYPE: DNA
<213> ORGANISM: Glycine max
<220> FEATURE:
<221> NAME/KEY: variation
<222> LOCATION: (99)..(99)
<223> OTHER INFORMATION: SNP Gm16:32541245

<400> SEQUENCE: 99
tacaaatttt atacacaaac ttaaaaatta taaataaaaa attyaataat cacaaaaatt    60
tarccattga tcaattggaa aaaaaggtac atttctctya aaataggtac cctaaaacat  120
aaaaaataga atcaactaaa atacttgtaa acaaatgaaa ggtctaacaa ttttcaaaca  180
atcakttatt atttacaca                                                 199

<210> SEQ ID NO 100
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32268012

<400> SEQUENCE: 100
tcccattacc caaaggtcc ttgctagcaa aagtatgagt gaggatcatt rtatgtaatc     60
ttattcttgc atatrcaaaa aggttgtttc caaattcaaa ytgatgacca accggttacc  120
aaaatacaac tttaargttg tgctagagct casaatcatt gatgtctatt agataaaaca  180
agaaaagttg agaaacaaaa t                                              201

<210> SEQ ID NO 101
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32516254

<400> SEQUENCE: 101
gttataatgt ttttatattg ggcaacaatg atttgccttt tttggtgatt ttattttcat    60
ctttcatgga gaattaygat ttgagrtggg gcaattagat rgwgaattt maatcscata   120 tgrtaatgta cgtagctcaa agccaagttc gaattggtca actaagatgg aagggtgtca  180
gatgaataat ttggagaagg a                                              201

<210> SEQ ID NO 102
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32269873

<400> SEQUENCE: 102
cmtggcgctt caattttaaa gcaatacgtt cattctcaat cttcattctt tcattctcta    60
gcttcaactt ttctaactcv agatctttt tcctactaaa mttctgccac ttgaatcttt    120
gtttcttcag ctccaacatc tcgtyttgaa tttgtagctt ctgctcttct aaytgaagtg    180
aacgagattc aaccsattgc t                                              201

<210> SEQ ID NO 103
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32344231

<400> SEQUENCE: 103
aaatcaacac tagacataat tgctgagtat tttgtctttc gaagattgac aagatttgtc    60
tcmatttcat cttttatctg catatgttct tcttcctctt ygttgycatt gtctgactca    120
tcagcatcca agccttcctc atcatcatcc tcagattcct cacccagcat tgatttcttc    180
aactctttat aacgcttttc t                                              201

<210> SEQ ID NO 104
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32550578

<400> SEQUENCE: 104
atttggaaga ttgaaaatcg macgcgagaa actccaaaac cttaacmgtt tcaatctttg    60
atttcagaga tccgtttctg agaacaaata tcatcgcatc waagcattgt tcscgagcgt    120
caagaatcag ctttcgaatt ctctctccag ttgactttcc gttttctcgg aaaactgaac    180
cgagaagata gatcgcgttt t                                              201

<210> SEQ ID NO 105
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32346483

<400> SEQUENCE: 105
ytgggatttg tgaggcttag cttaagaagm acaaattgaa gatttagctc tagggactta    60
aggctaagcg wgaaattttc tcaatcttag catggrcttc rrgctaagtg tagaacttct    120
caagctaagt gtgagagagg aagtaaaggg cttgagcatt ctaagcttra agctaaacgt    180
gagaacattc tagttggaag c                                                201

<210> SEQ ID NO 106
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32573101

<400> SEQUENCE: 106
ggaaatggaa ggttaaatgg gtagggtgg ttccttgacc aaaattatca gaactgatga      60
ttttatatac actaaactac aacatgtaaa gggcatatgc ycaaattaaa tggaagacag    120
ataatttaag agaaaaagag gaaaggggaa aaaagaagag tgagaagaga ataaggatgg    180
acataagaac caccaacaaa c                                              201

<210> SEQ ID NO 107
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32217820

<400> SEQUENCE: 107
ttgaataatc cgtaayatat ttatattaca watkgyttaa ttcgtaataa acaaaatgat     60 ttatractttt ctyactcttc attttaagtt gtctttcatt ycattttaaa ttcctacaaa   120
ataarccatc aaataagcac atataaccta tcaaatgat aaactaaaga gaaaaataac    180
atatttataa atttataagt a                                              201

<210> SEQ ID NO 108
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32324084

<400> SEQUENCE: 108
ttctacacct tttwgttata ttctttccat acacctactt tatggtcatt gatgatgata    60
ctttagcctt aaaaaacatc aaatgacacc cctgacttay gaataaagtt taggttcsgt    120
aaggagtctt ggcaaccacc aaatcaagga ccaaagagaa acaccttgtc tgtccaaagc    180
tctaagcaaa ttyggataaa                                                200

<210> SEQ ID NO 109
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32346915

<400> SEQUENCE: 109
ggtgrggttc tgycacttct catcccaaaa aatgtggtaa agrctsctcg agtcrgaggg     60
tgaaataaat gcaaggtcat grtatgagaa caaggggggga yactacttgg aagtttaagt   120
tcaatacttg tcataggaca aaaaagacaa agaaagaaat katgttaagc atrcaaaact   180
tgatgtctaa stttatgttt a                                                     201

<210> SEQ ID NO 110
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32324102

<400> SEQUENCE: 110
tattctttcc atacacctac tttatggtca ttgatgatga tactttagcc ttaaaaaaca           60
tcaaatgaca ccccctgactt aygaataaag tttaggttcs gtaaggagtc ttggcaacca         120
ccaaatcaag gaccaaagag aaacaccttg tctgtccaaa gctctaagca aattyggata         180
aagagaaaag aaataawgga                                                      200

<210> SEQ ID NO 111
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32234335

<400> SEQUENCE: 111
ttccatcatc aaattctcac cgttattatc agctttgttg atttccacat tactcaccac          60
tatttgttgt tgttgttgta gttgtgggac caatggctgc rcttgtgggg cctcaggaac         120
tgttgttgtt tgtgcttgtt gtggtgttgg agttgatgtt ggtgttgctt gtggcactgg         180
ttgctgtgga acaacagtga t                                                    201

<210> SEQ ID NO 112
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32233691

<400> SEQUENCE: 112
tttttccgac aatatgtgaa ttcaaattga tccatcattc tttaattgat gcccttttg           60 gtcaatattt tttcctctca ctctccggaa gcatcagctg wggctggttt gctcgcaact         120
atctcataat tatcacctcc ttcgtcgtcc tcatcctcgt cttcatctcc aatttccttg         180
tcgtcctcgt catcctcatt c                                                    201

<210> SEQ ID NO 113
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32235048

<400> SEQUENCE: 113
gtgttgatgg tggtgttatg ttgagaatgc tttgaggcat aggaagtgat gttgtggatg          60
gaacagtggt gttgttgttg ttattagaca ctggtggcaa yggaagtggc attattattg         120

```
atgatggtgt agttgtagtt gttgttacca ctattgacac tggtgttgct gatagtgctg    180
ttgtttgtgg tggcggcttt g                                              201

<210> SEQ ID NO 114
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32297045

<400> SEQUENCE: 114
atctgccaga gcatgtctga gttttttctt cctgctggat attttgttgc tggatattgt    60
aaacttgctg ctctgtgggc aggccgtctc taatgtctttt katgggagga tggatttagg   120
tggaggaatg tttctaaaag gtawatccca gtatgtggaa gttggatttc tcacattgct   180
agaatccctg agtttctgta                                                200

<210> SEQ ID NO 115
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32301650

<400> SEQUENCE: 115
caacgggtca agtaaaagtg ctgaagcaaa atgtgtagag agggaaagac aaacacttct    60
caacttcaaa caaggcctca tagatgcctc tggcatgctg ycttcatgga gggatgatga   120
caataataaa gattgytgca aatggaaagg cattgaatgc aacaatraaa ctggtcacat   180
agacatgctt gatcttcgkg g                                              201

<210> SEQ ID NO 116
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32217515

<400> SEQUENCE: 116
caacactcca aggtcatttg tatattgttt trgcccacaa tacactcatc ttaakgwgtc    60
catttatcya actagagtaa atayatttgt tcaaagggaa rttacttagc acaccccatt   120
ttttgcttga tgcatcccat attttctaaa atccccttct taccttcttc ctcccaagca   180
atgcctcttc tcccaarcct c                                              201

<210> SEQ ID NO 117
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32308185

<400> SEQUENCE: 117
ggagaggcat tcaatgcaay gatgaaactg gtcacgtaca agtactcaat cttcattgtc    60
cagatagaca ttatttgaca ggtgcaatma atctcacttc rttgattcac ttgcaaaaca   120
```

```
ttgaacatct gatctcagca ataatgattt tttacgatgt tacmtmccgg aagccatggg    180
ctccttcacc aactyragat a                                              201
```

<210> SEQ ID NO 118
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32459325

<400> SEQUENCE: 118

```
tcgactttc tccaagcttc aaattttgga aaaccttgac ctttcacaga atgatcartt    60
atcactaaat ttcaaatcca atgtcaatta tagtttctcc mgcttaagga gtttggactt   120
atcttctatg gatttaactg aatttccgaa attatctgga aaagtcccaa atttaatgtt   180
tatctatttg tccaacaaca a                                             201
```

<210> SEQ ID NO 119
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32288737

<400> SEQUENCE: 119

```
aaattttacc tttctttggg atctgcacag agaatcatac atcaaatgat taccatatac    60
ctcaagtaac ccactgatgg cgtggatata cgtgtgttta yactctatag tctatatgaa   120
ttaatacact amctttctct gccttaaatt aggtaaatat saatacagct caagcactta   180
aataaaactg gtgtgatgat a                                             201
```

<210> SEQ ID NO 120
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32339081

<400> SEQUENCE: 120

```
attttggggt cccaccaaat agccaaagac attattatta ttactattac taagggttgt    60
ttttattatg agaaaactgg gaaagaaatc ttggttggat rcactgatat tggtttggaa   120
tgttgtgtgc ttgcaggatt tttgttagtt ggaactggta atgaattaga tttagttttt   180
gtgtgtgytt ttttwatttt g                                             201
```

<210> SEQ ID NO 121
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32273554

<400> SEQUENCE: 121

```
tcatttgttg gatttatgct ttgcacaatg atattgtttt ggctatgcaa gattctgcaa    60
```

```
gttgagagat gttgctctct acttacccaa atggacttgc mcttttcttg gtatagttaa      120
gctcaatgtt gatagtagtt gtgtattccc tcgaccctag tgatagggac tggtggtctg      180
catcgtgacc acaacaatgt t                                                201
```

<210> SEQ ID NO 122
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32268047

<400> SEQUENCE: 122

```
tgagtgagga tcattrtatg taatcttatt cttgcatatr caaaaaggtt gtttccaaat       60
tcaaaytgat gaccaaccgg ttaccaaaat acaactttaa rgttgtgcta gagctcasaa      120
tcattgatgt ctattagata aaacaagaaa agttgagaaa caaaatcatt tttattctac     180
tccctatgtt catatttaca a                                                201
```

<210> SEQ ID NO 123
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32270524

<400> SEQUENCE: 123

```
ctttctcgga aagataatcr atcaaatcca acaagaagg attttcaaca acccgacagg       60
aagttcccct cccaagcata acattaagct ttttgtagct wttactaagg tcattgaatt     120
tatcctcaca ttgttgaggt gaaacatggt aacctctttc agccatgacc ttagaaatgg     180
atttccattt cccttttattt t                                               201
```

<210> SEQ ID NO 124
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32349993

<400> SEQUENCE: 124

```
ggacaaaatt gctccaactt gatgaacatc aattagcaga agtagctcat aatagcagta       60
gtaatttaat tatgagtttg tgtgtggtga gacttgtgaa kggtacatta ttatgcattt     120
tagtgatgtt tattttctct aattctggat tggaagcaca acctttgaaa tttatgtttt     180
atagcttttt ggatgaatga a                                                201
```

<210> SEQ ID NO 125
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32329724

<400> SEQUENCE: 125

```
ccatcaaaac acgagacttr aaagasaccc aatctctagt ctcaatctca acyctamaaa       60
```

-continued

```
ttttaaatca cttggcaata ctacaaagaa actgcacata ratgtttcca cacacacaaa      120
aacacagttg atgctatgct cacacatggt tatrsgtatt atgcagtcaa gcccagtgmt      180
tcacaccaag cacagaaacc a                                                201
```

<210> SEQ ID NO 126
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32236209

<400> SEQUENCE: 126

```
taaaaggaaa ttaaacaaat ccaaatgaaa gagcaaaaaa ccaagagaga gagtgagtga      60
gacggaaaaa aattaacatg gaattgaagt gaaacacatt yccaagagaa tgaagagatg     120
aaagaacaaa acttgagcaa gaattgagag gtttcagatc tccaagtacc caacaactca    180
aactggtata gtactcatcg a                                                201
```

<210> SEQ ID NO 127
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32275786

<400> SEQUENCE: 127

```
tttttaacwt ggttgattag tatgtttcgg atgttctatg attattttgg agtgttttga      60
ttttgtggtt cattgaaaga ttgaatttta aggttttgga wkttcacggt tctccaattt     120
taaaatccac tgtctgtggg tggttgcttg agttttgctt ttgctttttt aaattttaga    180
tgttctgtat ggctgtgggt t                                                201
```

<210> SEQ ID NO 128
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32275787

<400> SEQUENCE: 128

```
ttttaacwtg gttgattagt atgtttcgga tgttctatga ttattttgga gtgttttgat      60
tttgtggttc attgaaagat tgaattttaa ggttttggaw kttcacggtt ctccaatttt     120
aaaatccact gtctgtgggt ggttgcttga gttttgcttt tgctttttta aattttagat    180
gttctgtatg gctgtgggtt t                                                201
```

<210> SEQ ID NO 129
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32218068

<400> SEQUENCE: 129

```
cctcaattca caactctcaa ttatgttttt ttgacaatta ttaagccacc accctaaaag    60
gaaatgatca tctccctaaa atggaaatct agtaaaaack gttattcttg tgcatgcacg   120
aaatcgttca cattcttaat ttcaaatttt caactcactc aaaaaattag aagtacttgg   180
cacgatgctt ctactcctcc                                               200

<210> SEQ ID NO 130
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32230177

<400> SEQUENCE: 130
agcatggcag taggttttgg acattaattg cactggttta cctataatct gatgggccag    60
wtggagggca tgtctgagtc cagagcagat gaacttctga rcctcatcaa gctctcctac   120
ctagttacaa tggatttgga cagagtgatt aatgacaatt gaattgatga tatataagct   180
taaacattaa aacactgaag a                                             201

<210> SEQ ID NO 131
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32287161

<400> SEQUENCE: 131
tcgtgcaact tcgttggaac taaatcaagt gcctgataac agagaagatt tatcaatttg    60
attcacaaat gatgcttttg aaactatasc agcatgtatg sgtgattcca atttcaagtg   120
gaaagaaaaa taagagaaaa attgtcagtg tcagttaaaa gaaatgtaaa ttacccgttc   180
cttgcccgtg aaagactgtc c                                             201

<210> SEQ ID NO 132
<211> LENGTH: 173
<212> TYPE: DNA
<213> ORGANISM: Glycine max
<220> FEATURE:
<221> NAME/KEY: variation
<222> LOCATION: (73)..(73)
<223> OTHER INFORMATION: SNP Gm16:32186606

<400> SEQUENCE: 132
tagctagaag cactattcta gaacaagctt gcaaaaagga ctcaagttat ctttggtaag    60 ggaagctttta gasctcaagt ctagcttgga gacttttgat tttgaagctt tgtattttgt   120
atcttggcta aagaatatat gttggaaaaa gtcttcttga agagctctta aag           173

<210> SEQ ID NO 133
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32338878

<400> SEQUENCE: 133
tctgctgaaa acaatatggt tgcaaattat atgaagcttt aagctttaat gttgccataa    60
```

```
gctttaagtt attcctcttc aaaaaagaaa aagctttaar ttattattat atgattggag      120
acggcgaaga gtttaagtgt gactaacctc ggactgagaa atagtctcgt agttggctta      180
caagacaaaa agttgtagcg                                                  200
```

<210> SEQ ID NO 134
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32182404

<400> SEQUENCE: 134

```
aattacagat agatattcta aacayagcaa gataacttta tacgaaatgg aggaaaccca      60
tcaacaatgg tgcacatatg attgtctaga attgattagg rctggaaata accatgtttc      120
tcgaggtttt ctcgttttag tggttgatgc atatatacta ttctgccggc aaacatatgg      180
ccatgatgat aaaaataagc t                                                201
```

<210> SEQ ID NO 135
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32323924

<400> SEQUENCE: 135

```
atgacccgct caaagacgat atgaaaacwa taactcctaa ttaggatcat atcataatcc      60
atgatcatgc tgaatgagaa tgacttgtga gaacaatttg ytagttatag tctgcgcgta      120
tcttgggggg gaggatgatt atttagagaa tcatgatttt ttctacacct tttwgttata     180
ttctttccat acacctactt t                                                201
```

<210> SEQ ID NO 136
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32319745

<400> SEQUENCE: 136

```
gatttataag cctctgtctg gactatttgt gaagggtcta atattggtat aatcccagca      60
tttagaggaa ttrcttacta attttcttac aggggtgata maaataggtt ttataattta      120
cttagactta tcatattayt aaaatatgtt tgtgtgtgtt aatttgatta aatttataga     180
aatagatcgt gatccctctg a                                                201
```

<210> SEQ ID NO 137
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32270866

<400> SEQUENCE: 137

```
ccgcttcatg atgaccatca acacmttctt cgactaaact tgcatcactt ggtgaggtct    60
tgtgtatacc cctttgatta aactcagtca ttgacaaaat ytgatgatca cayttctgga   120
aggatcccat tgtaagaggc aaaccatcat gaattgagga gtgcactaaa gacctttggc   180
aatgatgaat atgttgttgg t                                             201
```

<210> SEQ ID NO 138
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32307865

<400> SEQUENCE: 138

```
tataatttcc tccagaaaac caacagatca taattctctc ttgcattggc attatcttgt    60
cttgtcctta gttaagatta ttcttatcag caaaattata wtgagtagtt attttctgac   120
aacattttat gctctgttcc tgcttttatt tmattcctca ggatttamtc tcggattaaa   180
tgggtcactt maaagtyctr a                                             201
```

<210> SEQ ID NO 139
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32341072

<400> SEQUENCE: 139

```
tgactagaat atagaaattg taattatcca ggtatccacc aktagctctt gccactatcc    60
ataagagcaa gactctttga gtaagatatt acagattcaa ractcaaatt ggtgtgcttt   120
tgcatagttt ggctgaattc aatcaaatga ttctgactat gtagtattac katcttagta   180
ttttagctaa agtcaatttt g                                             201
```

<210> SEQ ID NO 140
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32204594

<400> SEQUENCE: 140

```
aaaaaaaaaa cattagaaaa ttattttgt ttgacaacca ggttgtataa aaatatagta    60
tgtgattcgc aacttacata tgtcctttga aagtagttat maacctaatt gtttgacttg   120
tttggggtaa ccaagaagag ttcatcagga tccataaatc gccaagtctt ataaccttaa   180
ataaaagcca atgaatgctt a                                             201
```

<210> SEQ ID NO 141
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32288768

<400> SEQUENCE: 141

```
gaatcataca tcaaatgatt accatatacc tcaagtaacc cactgatggc gtggatatac    60
gtgtgtttay actctatagt ctatatgaat aatacacta mctttctctg ccttaaatta   120
ggtaaatats aatacagctc aagcacttaa ataaaactgg tgtgatgata aaaawaccat   180
ggataactaa ttaaggatac t                                             201
```

<210> SEQ ID NO 142
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32454218

<400> SEQUENCE: 142

```
caaaactcgc ttaagcccca actgtgcatg gcttaagctc ttagccaaca ccacttatgc    60
tacataaaaa catgttagtt tgctcatttg ttcttttctt rcaggaaatc tctccaagtt   120
tggrytcaca ttcgtgattt ggytcctttc cgcagacrtt tcacttcttt ayagcgcatt   180
actgactctt taattaggrg c                                             201
```

<210> SEQ ID NO 143
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32321898

<400> SEQUENCE: 143

```
tcccattcaa cgtcggttgt gaatctaagt gttttgactt tgatcttttt tgttctgtgt    60
tttgtgtcct tgtgattgct tttaaacctc aatatgtgtt wgttatagta tggagatatt   120
taaagaagaa aaaaaaacaa ttgtattttg tgatggtttt gataatgtta aatctacatg   180
cagggtcaaa atgaattwta                                               200
```

<210> SEQ ID NO 144
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32554984

<400> SEQUENCE: 144

```
aaagattgtg gttgaaaaaa attcagcaac taattttaga cgagtctgaa ttgagagcaa    60
ttcttgatga atgcaaaaaa ttgwtttgtt taaatacaaa mtttaaactt aaagttcatt   120
aagagtcaag tcaatgtata gctagttgct cagtctttag aagggcatct gcatatttat   180
tatttagcta gctscatgtt c                                             201
```

<210> SEQ ID NO 145
<211> LENGTH: 200
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32350129

```
<400> SEQUENCE: 145
ctctaattct ggattggaag cacaaccttt gaaatttatg ttttatagct ttttggatga      60
atgaaagtar catttctttt gaagataaga atgaaagtaa yacataaaar atgttgaaag     120
actagttgat aatactgtag taattagctt ttggaattaa atagcaataa ttttggaaag     180
cacttctcag tacgcctygg                                                 200

<210> SEQ ID NO 146
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32243083

<400> SEQUENCE: 146
cgstgatgta gcaaaaaaac tgtaccaaaa aaaaaaagat ttatgcagga catgtgtttt      60
taggcagagc catttatgaa cggaagttaa tagtgaccaw tcctgttgga tttgtaacct     120
accgttataa atggcatcaa aatttcgatg gcagtcgctg cgttctctat ccaaggagaa     180
ttattggatt gccaacccta                                                 200

<210> SEQ ID NO 147
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32291418

<400> SEQUENCE: 147
cgagatataa gattagtcta atgacgaaaa gagaasaaaa gaaaaaggat taataatact      60
aacaattaat atttgtcgat aaaaaacaca caaagtaggg rtagcgtacc ttgctgacag     120
cggaacaaac gaacttgcaa ccgagaacaa tgtgactgag caagatggtg aaatcgccgc     180
gtgactcggg gtgcttggat t                                               201

<210> SEQ ID NO 148
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32213522

<400> SEQUENCE: 148
aacatttttk aataccgcgt cctatgtaat attctaccaa tctcatcatg ygtatgcaat      60
tgtagtaact agtaaggcag ttaatttacc aaacttaaac rgtactctta aaaactaaat     120
aataaagatt tkcatattta ttactctact atcattattt tataaatttt actatcatat     180
ttttaaattt tgttcacaaa t                                               201

<210> SEQ ID NO 149
<211> LENGTH: 200
<212> TYPE: DNA
<213> ORGANISM: Glycine max
<220> FEATURE:
<221> NAME/KEY: variation
<222> LOCATION: (100)..(100)
<223> OTHER INFORMATION: SNP Gm16:32217755
```

<400> SEQUENCE: 149
ccacgaaacc ctcctgcatc atcaatccac caytgcctta catcatycac aaatktatta    60
tgaattgaat aatccgtaay atatttatat tacawatkgy ttaattcgta ataaacaaaa   120
tgatttatra ctttctyact cttcatttta agttgtcttt cattycattt taaattccta   180
caaaataarc catcaaataa                                                200

<210> SEQ ID NO 150
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32541584

<400> SEQUENCE: 150
cataacataa ttaactttat ttcaagacag ctatttaaaa tcagagttcc ttcgacattg    60
aaggctgagg caattattca atgattagca tgtttgcttg ytcattttt cacatattta   120 cccaaatttt cacrtcaagg atggcrcaga cgcaaaacca aacacatggg atattggttg   180
tgtttatttt ttcgttaaac t                                              201

<210> SEQ ID NO 151
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32554335

<400> SEQUENCE: 151
ttcatcatta ttgtaaaagt acatctaata mtagttgtgt tcagaaagcc gttctatacg    60
ttcaacggac ctcttacact ttctatgttt tgttttccc yatatttaag agagaagtgc   120
cttgtctcar aaaagaaaa gagagaatgg tgccttagag agagggkggg agaattttgt   180
tacacgatac ttgtcttctt a                                              201

<210> SEQ ID NO 152
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32509795

<400> SEQUENCE: 152
cggttgataa tttttctagc tgttcattaa trcgcttaga ttttattttt taactttta    60 tattggtgaa tagtatggag ttaagtagtg aataatgtgt wgacaatcaa caatcatttc   120
gttaataaaa taatatacat ttttttaact cattacgttc ccccgtttta ctaatatcga   180
tataatgttt aaggaggaaa a                                              201

<210> SEQ ID NO 153
<211> LENGTH: 201
<212> TYPE: DNA
<213> ORGANISM: Glycine max
<220> FEATURE:
<221> NAME/KEY: variation
<222> LOCATION: (101)..(101)

<223> OTHER INFORMATION: SNP Gm16:32239092

<400> SEQUENCE: 153

```
ctccaacact tgagctagta ataatttgaa tagaacgatg atatataaat gcatacatga      60
tatttttaga cattgtctga tatataagat gcttaggata ygttggattg cctattacta    120
agtccaattt gagaggccta attattttga aatattatta gaatatgttt ggatayaagr    180
ctaaaatttc tttagacast t                                              201
```

<210> SEQ ID NO 154
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32491511

<400> SEQUENCE: 154

```
cagaaaagat gtggttagta tatctctaaa aataatgtag cattaagaaa agatcgtgac     60
tatgctgcaa aagttgtata ttgaagtctt gagtctagat rtgattaatt aattcattga   120
aatgccaagt ctcaaaatcc cgaattayac ttatgcaaaa tcacctacta ccttttagag   180
tcaattaaac cattattaac a                                             201
```

<210> SEQ ID NO 155
<211> LENGTH: 201
<212> TYPE: DNA
<213> ORGANISM: Glycine max
<220> FEATURE:
<221> NAME/KEY: variation
<222> LOCATION: (101)..(101)
<223> OTHER INFORMATION: SNP Gm16:32270738

<400> SEQUENCE: 155

```
ttttcttctt ttgctactgt tgtcaraagt tgcatcctca cctatgtaag acatgaccat     60
tatyagaagt tttaccatct tatcagtcca tttcacctgc kgccaaggag tactttttt    120
ccctttaccc gcttcatgat gaccatcaac acmttcttcg actaaacttg catcacttgg   180
tgaggtcttg tgtataccc t                                             201
```

<210> SEQ ID NO 156
<211> LENGTH: 22
<212> TYPE: DNA
<213> ORGANISM: Artificial Sequence
<220> FEATURE:
<223> OTHER INFORMATION: Oligonucleotide Primer/probe

<400> SEQUENCE: 156

```
caaaatgttt cccatttggt tc                                             22
```

<210> SEQ ID NO 157
<211> LENGTH: 25
<212> TYPE: DNA
<213> ORGANISM: Artificial Sequence
<220> FEATURE:
<223> OTHER INFORMATION: Oligonucleotide Primer/probe

<400> SEQUENCE: 157

```
ctgcatcact tcaaaatgag ataaa                                          25
```

<210> SEQ ID NO 158
<211> LENGTH: 14

```
<212> TYPE: DNA
<213> ORGANISM: Artificial Sequence
<220> FEATURE:
<223> OTHER INFORMATION: Oligonucleotide Primer/probe

<400> SEQUENCE: 158
ttgcacaaca aatg                                                       14

<210> SEQ ID NO 159
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 159
ttgcacacca aatg                                                       14

<210> SEQ ID NO 160
<211> LENGTH: 24
<212> TYPE: DNA
<213> ORGANISM: Artificial Sequence
<220> FEATURE:
<223> OTHER INFORMATION: Oligonucleotide Primer/probe

<400> SEQUENCE: 160
atcagctttg ttgatttcca catt                                            24

<210> SEQ ID NO 161
<211> LENGTH: 22
<212> TYPE: DNA
<213> ORGANISM: Artificial Sequence
<220> FEATURE:
<223> OTHER INFORMATION: Oligonucleotide Primer/probe

<400> SEQUENCE: 161
aagcacaaac aacaacagtt cc                                              22

<210> SEQ ID NO 162
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 162
aatggctgcg cttg                                                       14

<210> SEQ ID NO 163
<211> LENGTH: 14
<212> TYPE: DNA
<213> ORGANISM: Artificial Sequence
<220> FEATURE:
<223> OTHER INFORMATION: Oligonucleotide Primer/probe

<400> SEQUENCE: 163
atggctgcac ttgt                                                       14

<210> SEQ ID NO 164
<211> LENGTH: 26
<212> TYPE: DNA
<213> ORGANISM: Artificial Sequence
<220> FEATURE:
<223> OTHER INFORMATION: Oligonucleotide Primer/probe

<400> SEQUENCE: 164
```

```
aaattgggag atttctaatg ttaagc                                        26

<210> SEQ ID NO 165
<211> LENGTH: 22
<212> TYPE: DNA
<213> ORGANISM: Artificial Sequence
<220> FEATURE:
<223> OTHER INFORMATION: Oligonucleotide Primer/probe

<400> SEQUENCE: 165
gaggtcaaga aatggacaca aa                                            22

<210> SEQ ID NO 166
<211> LENGTH: 17
<212> TYPE: DNA
<213> ORGANISM: Artificial Sequence
<220> FEATURE:
<223> OTHER INFORMATION: Oligonucleotide Primer/probe

<400> SEQUENCE: 166
tagctcactc taaagtc                                                  17

<210> SEQ ID NO 167
<211> LENGTH: 17
<212> TYPE: DNA
<213> ORGANISM: Artificial Sequence
<220> FEATURE:
<223> OTHER INFORMATION: Oligonucleotide Primer/probe

<400> SEQUENCE: 167
tagctcactc tgaagtc                                                  17

<210> SEQ ID NO 168
<211> LENGTH: 23
<212> TYPE: DNA
<213> ORGANISM: Artificial Sequence
<220> FEATURE:
<223> OTHER INFORMATION: Oligonucleotide Primer/probe

<400> SEQUENCE: 168
cacccttaga agcaaagatt gaa                                           23

<210> SEQ ID NO 169
<211> LENGTH: 20
<212> TYPE: DNA
<213> ORGANISM: Artificial Sequence
<220> FEATURE:
<223> OTHER INFORMATION: Oligonucleotide Primer/probe

<400> SEQUENCE: 169
ccttggtgac tgaggatgtg                                               20

<210> SEQ ID NO 170
<211> LENGTH: 15
<212> TYPE: DNA
<213> ORGANISM: Artificial Sequence
<220> FEATURE:
<223> OTHER INFORMATION: Oligonucleotide Primer/probe

<400> SEQUENCE: 170
agggttctca acttg                                                    15

<210> SEQ ID NO 171
<211> LENGTH: 15
<212> TYPE: DNA
<213> ORGANISM: Artificial Sequence
```

```
<220> FEATURE:
<223> OTHER INFORMATION: Oligonucleotide Primer/probe

<400> SEQUENCE: 171
agggttctca gcttg                                                          15

<210> SEQ ID NO 172
<211> LENGTH: 109
<212> TYPE: DNA
<213> ORGANISM: Glycine max
<220> FEATURE:
<221> NAME/KEY: variation
<222> LOCATION: (33)..(33)
<223> OTHER INFORMATION: SNP Gm16:32544169

<400> SEQUENCE: 172
caaaatgttt cccatttggt tctatttgca camcaaatgc tgccmaaaag tcttctttct          60
ctatttcata caatcatca ccattttatc tcattttgaa gtgatgcag                       109

<210> SEQ ID NO 173
<211> LENGTH: 110
<212> TYPE: DNA
<213> ORGANISM: Glycine max
<220> FEATURE:
<221> NAME/KEY: variation
<222> LOCATION: (74)..(74)
<223> OTHER INFORMATION: SNP Gm16:32234335

<400> SEQUENCE: 173
atcagctttg ttgatttcca cattactcac cactatttgt tgttgttgtt gtagttgtgg          60
gaccaatggc tgcrcttgtg gggcctcagg aactgttgtt gtttgtgctt                     110

<210> SEQ ID NO 174
<211> LENGTH: 79
<212> TYPE: DNA
<213> ORGANISM: Glycine max
<220> FEATURE:
<221> NAME/KEY: variation
<222> LOCATION: (37)..(37)
<223> OTHER INFORMATION: SNP Gm16:32296634

<400> SEQUENCE: 174
aaattgggag atttctaatg ttaagcttgt tgacttyaga gtgagctaaa tcttgaattt          60
gtgtccattt cttgacctc                                                      79

<210> SEQ ID NO 175
<211> LENGTH: 100
<212> TYPE: DNA
<213> ORGANISM: Glycine max
<220> FEATURE:
<221> NAME/KEY: variation
<222> LOCATION: (43)..(43)
<223> OTHER INFORMATION: SNP Gm16:32271574

<400> SEQUENCE: 175
cacccttaga agcaaagatt gaaactttkt ctcaaaatca agytgagaac cctgaaacaa          60
agacaaacaa ctaaaaagaa cacatcctca gtcaccaagg                                100
```